United States Patent
Dodd et al.

(10) Patent No.: US 11,174,226 B2
(45) Date of Patent: Nov. 16, 2021

(54) AZETIDINIMINES AS CARBAPENEMASES INHIBITORS

(71) Applicant: Centre National de la Recherche Scientifique (CNRS), Paris (FR)

(72) Inventors: Robert Dodd, Paris (FR); Kevin Cariou, Paris (FR); Corinne Minard, Aulnay sous Bois (FR); Bogdan-Iuliu Iorga, Antony (FR); Thierry Naas, Clamart (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 15/759,084

(22) PCT Filed: Sep. 7, 2016

(86) PCT No.: PCT/EP2016/071115
§ 371 (c)(1),
(2) Date: Mar. 9, 2018

(87) PCT Pub. No.: WO2017/042233
PCT Pub. Date: Mar. 16, 2017

(65) Prior Publication Data
US 2019/0055194 A1 Feb. 21, 2019

(30) Foreign Application Priority Data

Sep. 9, 2015 (EP) .................................. 15306378

(51) Int. Cl.
| | | |
|---|---|---|
| C07D 205/06 | (2006.01) | |
| C07D 205/085 | (2006.01) | |
| C07D 401/04 | (2006.01) | |
| A61K 31/397 | (2006.01) | |
| A61K 45/06 | (2006.01) | |

(52) U.S. Cl.
CPC .......... *C07D 205/06* (2013.01); *A61K 31/397* (2013.01); *A61K 45/06* (2013.01); *C07D 205/085* (2013.01); *C07D 401/04* (2013.01)

(58) Field of Classification Search
CPC ... C07D 205/06; C07D 401/04; A61K 31/397
See application file for complete search history.

(56) References Cited

PUBLICATIONS

STN Registry entry for CAS RN 55268-38-7, Entered STN Nov. 16, 1984, Accessed Mar. 26, 2019.*
Ito et al. in Cancer Science 94(1), 3-8 (2003).*
STN Registry database entry for CAS RN 123134-51-0, Entered STN Oct. 13, 1989, Accessed Jul. 22, 2019.*
Gospodova, Tz. et al., Stereocontrolled intramolecular cyclization of anti-beta-aminonitriles. Convenient access to trans-azetidin-2-imines, Bulgarian Chemical Communications, 2008, vol. 40, No. 4, pp. 568-571.
Whiting, M. et al., Copper-Catalyzed Reaction Cascade: Direct Conversion of Alkynes into N-Sulfonylazetidin-2-imines, Angew. Chem. Int. Ed., 2006, vol. 45, pp. 3157-3161.
Perst, H., Product Class 17: Ketenimines, Science of Synthesis: Houben-Weyl Methods of Molecular Transformation, 2006, pp. 781-839.
Barbaro, G. et al., Periselectivity in Cycloadditions to Vinylmethylketene and Structurally Related Vinylketene Imines, J. Org. Chem., 1987, vol. 52, pp. 3289-3296.
Mostowicz, D. et al., A New Approach to the Synthesis of Chiral Beta-Lactam Derivatives, Polish Journal of Chemistry, 1983, vol. 57, pp. 297-299.
Odanaka, M. et al, Nippon Kagaku Kaishi: Journal of the Chemical Society of Japan, 1975, No. 9, pp. 1524-1529.
DeKorver, K. et al., Introducing a New Class of N-Phosphoryl Ynamides via Cu(I)-Catalyzed Amidations of Alkynyl Bromides, Organic Letters, 2011, vol. 13, No. 18, pp. 4862-4865.
Wang, Xiao-Na et al., Synthesis of Cyclopentenimines from N-Allyl Ynamides via a Tandem Aza-Claisen Rearrangement-Carbocyclization Sequence, J Org. Chem, 2013, vol. 78, pp. 6233-6244.
Kazuhiro et al. "Synthesis of 1-haloethenamides from ynamide through halotrimethylsilane-mediated hydrohalogenation". Tetrahedrom Letters 55 (2014) 632-635.
Pizzetti et al. "Microwave-Assited Animocarbonylation of Ynamides by Using Catalytic [Fe3(CO)12] at Low Pressures of Carbon Monoxide" Chem. Eur. J. 2011, 17, 4523-4528.
Sato et al. "Radical Additions of Arenethiols to Ynamides for the Selective Synthesis of N-[(Z)-2-(Arylsulfanyl)-1-alkenyl]amides" Bull. Korean Chem. Soc. 2010; vol. 31; No. 3; pp. 570-576.
Gati et al. "Intramolecular Carbocupration of N-Aryl-ynamides: A Modular Indole Synthesis" Organic Letters; Jun. 2013; 15(12): 3122-3125.
Kim et al. "Highly efficient synthesis of a-amino amidines from ynamides by the Cu-catalyzed three-component coupling reactions" Tetrahedron Letters; 49 (2008) 1745-1749.

(Continued)

*Primary Examiner* — Alicia L Otton
(74) *Attorney, Agent, or Firm* — Banner & Witcoff, Ltd.

(57) ABSTRACT

The present application relates to novel azetidinimine of formula (I). Wherein $R_1$-$R_6$ are as defined in claim 1. The azetidinimine of the invention are useful as antibiotics and as inhibitors of a carbapenemases. The present invention thus further relates to their use in antibiotic therapies and their methods of synthesis.

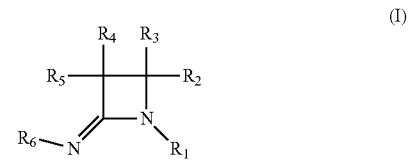

(I)

33 Claims, No Drawings

(56) References Cited

PUBLICATIONS

Schwan et al. "The synthesis and unimolecular decomposition of four novel $D^1$-1,2,4-triazolines$^1$". Department of Chemistry, McMaster University, Hamilton, Ont., Canada L85 4M1. Can. J. Chem, 66, 2285 (1988).

Crandall et al. "Reaction of N-Isopropylallenimine with organic azides". J. Org. Chem. vol. 40, No. 14, 1975 2045-2047.

Tlili "Synthesis and Reactivity of Diaza-1,2 Spiropentanes" Journal of the Chemical Society of Tunisia, vol. III—n° 8—Dec. 1988.

* cited by examiner

AZETIDINIMINES AS CARBAPENEMASES INHIBITORS

RELATED APPLICATION DATA

This application is a National Stage Application under 35 U.S.C. 371 of co-pending PCT application number PCT/EP2016/071115 designating the United States and filed Sep. 7, 2016; which claims the benefit of EP application number 15306378.9 and filed Sep. 9, 2015.

The subject matter of the present application concerns novel products (azetidinimine) for their use in antibiotic therapies and their methods of synthesis.

INTRODUCTION

Antibiotics are commonly used in order to kill and/or block the growth of micro-organisms responsible of pathologies.

Although there are several families of antibiotics with different structures, the way these antibiotics act, however remains similar ones in comparison with each others. Among these antibiotics, there are β-lactams characterized by a β-lactam nucleus responsible for their biological activity. Most famous β-lactams are mostly derived from penicillins, cephalosporins, and carbapenems monobactams. However, one major problem is the resistance that bacteria develop to counter the action of these antibiotics by enzymes called β-lactamase which cuts the C(O)—N bond in the following manner:

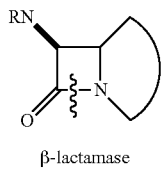

β-lactamase

To counter this phenomenon, it is useful to develop inhibitors of β-lactamases, more specifically carbapenemases inhibitors.

In this perspective, the antibiotic resistances of bacteria, in particular *K. pneumoniae, E. coli* and *E. cloacae*, are of great concern today. Studies have shown that the essential cause of these particular resistances are due to several types of enzymes and more specifically carbapenemases metallo-enzyme NDM-1 (12%), type oxacillinases OXA-48 (67%) and class A KPC-2 (14%).

Monobactam fonctions have been targeted in the art directly to induce antibiotic activities or have been used as β-lactamase inhibitors.

Examples of such antibiotics are e.g.:

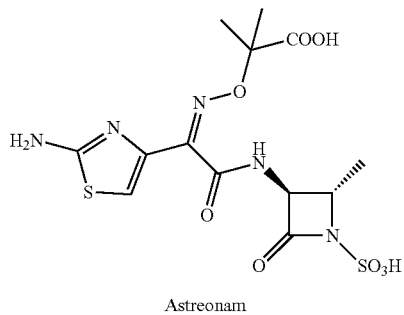

Astreonam

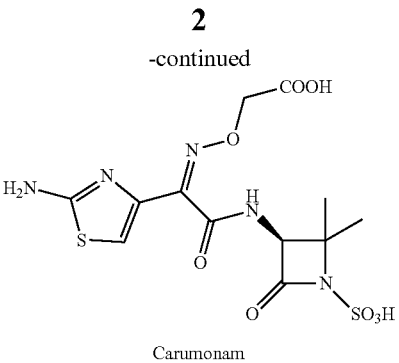

Carumonam

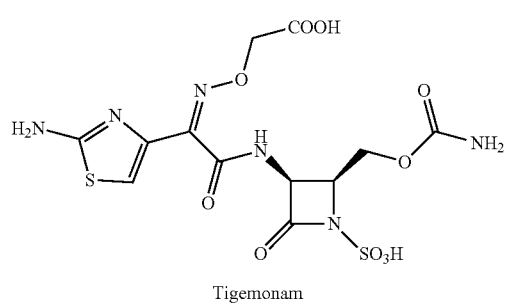

Tigemonam

Examples of such inhibitors are e.g.:

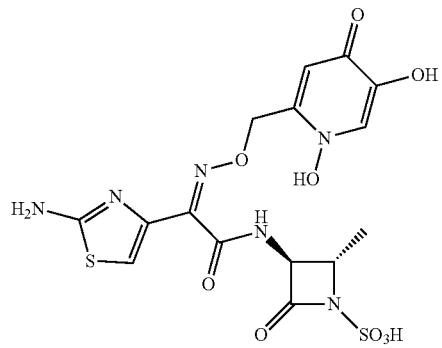

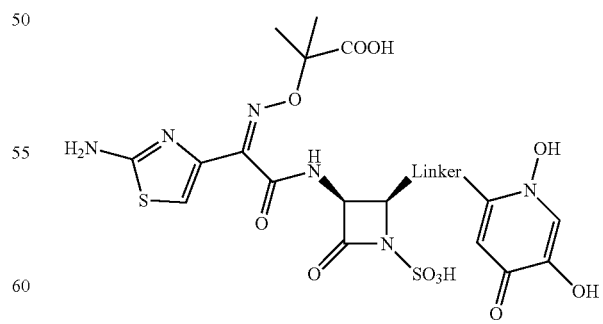

The antibiotic activity of the β-lactam feature is essentially due to the instability of the amide bond which can be cleaved in the presence of enzymes according to the following mechanism:

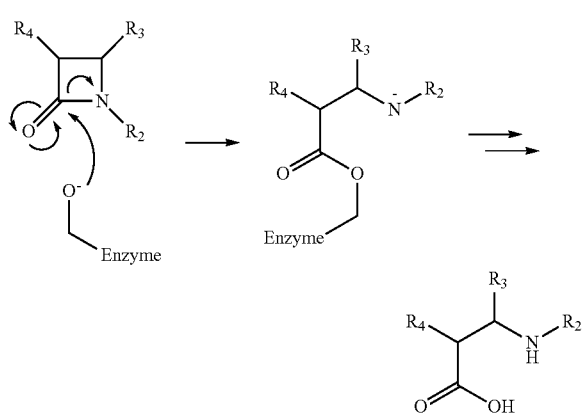

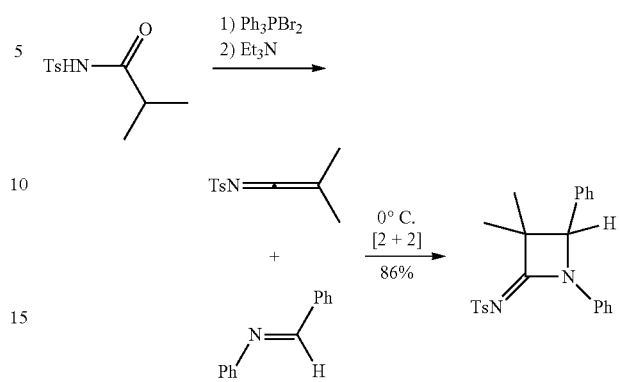

The amide bond is weakened by the delocalization of the non-binding electrons of the nitrogen adjacent to the carbonyl. Thus, in order to generate inhibitory molecules of β-lactamases, as "suicide molecules" capable of opening themselves faster than the antibiotic substance, it has been envisaged in the context of the present invention the preparation of structures in which the carbonyl group is replaced with unsaturated electrophilic groups. Indeed, few studies in this area have been reported in the literature.

The main issue raised by the process of Ghosez et al. is the necessity to generate a sufficiently electrophile cetenimine, which is for this purpose tosylated ("Ts"), in order to obtain the four membered ring azetidinimine. The nature of the azetidinimine is thus limited through this method.

Other ways to synthesize azetidinimine were reported later-on, such as the first cycloaddition [2+2] involving an intramolecular iminocetene and imine reported by the

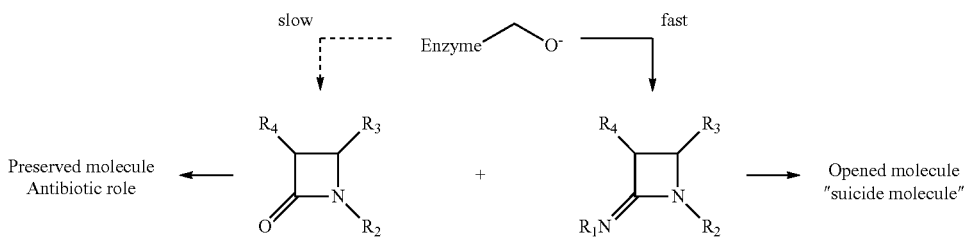

In this context, it has been chosen to direct efforts towards the synthesis of azetidinimines. The first aspect of the present invention concerns the identification of azetidinimines which present antibiotic properties, or at least are inhibitors of β-lactamases, more specifically inhibitors of carbapenemases.

research team of Alajardin (Alajardin, M., Molina, P., Vidal, A. *Tetrahedron Lett*. 1996, 37, 8945-8948.). It is reported that the driving force of this reaction is probably the formation of a ring system involving two closely hindered reactants.

Multicomponent azetidinimides synthesis was also studied by several teams such as the team of Folkin and more recently Shanmugam or Lu. It was showed that it was possible to access the desired compounds by reacting an alkyne, an azide substituted with an electron-withdrawing group and an imine in the presence of a complex copper (I) and a base (triethylamine or pyridine):

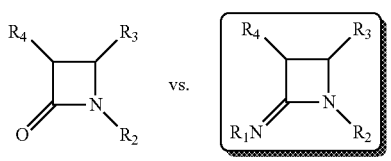

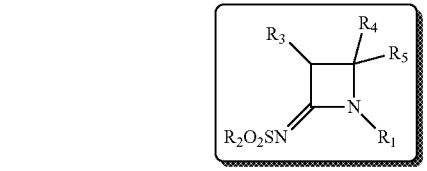

Folkin 2006
Shanmugam 2013
Lu 2013

However to obtain a broad array of such compounds, it was necessary to develop complementary synthesis methods to those of the prior art, which indeed do not enable to obtain all the desired compounds. The synthesis of these moieties has already been the subject matter of several study reports developed in particular by the team of Ghosez in the 1980 is (Van Camp, A., Goossens, D., Moya-Portuguez, M., Marchand-Brynaert, J., Ghosez, L. *Tetrahedron Lett*. 1980, 21, 3081-3084). Although it was then advanced that such structures could be treated as β-lactams, this had never been actually verified or even effectively witnessed. Moreover, using these molecules as "suicide molecules" is not disclosed or even suggested in this document.

Although applicable for the purposes of the present invention, the preparation of azetidinimines is scarce in the literature. Also, following the examples known in the literature as explained above, in view of work done at the laboratory, another original way of access was considered.

Indeed, it was observed the formation of an amidine by performing an addition on the indole α position of a ynamide in the presence of sodium tert-butoxide (Hentz, A., Retailleau, P., Gandon, V.; Cariou, K., Dodd, R. H *Angew. Chem. Int. Ed.*, 2014, 53, 8333-8337):

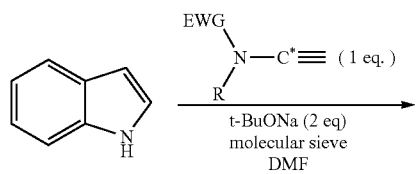

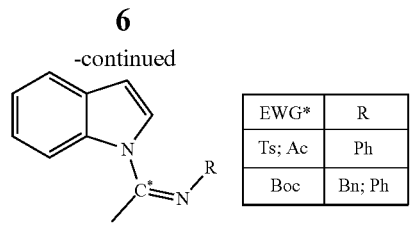

*EWG: Electron-Withdrawing Group
"C*": tagged carbon for the purpose of the comprehension of the above scheme.

A mechanism of the reaction was then advanced. A yet unproved hypothesis was that the base at the same time deprotonates the indole whilst unprotecting the ynamide, which then leads to its tautomeric form before being trapped by the indolate just formed. It was then supposed that a second tautomerization could then lead to the final product:

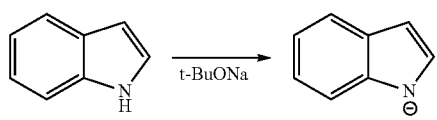

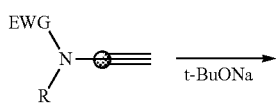

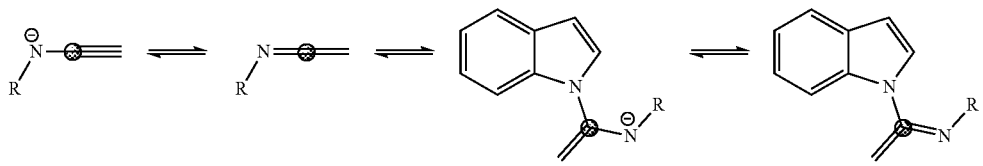

Such hypothesis allows the formation of a nitrogen unprotected iminocetene intermediate. Considering the prior art for the preparation of the intramolecular azetidinimines mentioned above, it seems reasonable to test this theory by adding a nucleophilic species to such intermediaries in order to obtain four-membered ring azetidimines wherein the exterior nitrogen would be unprotected:

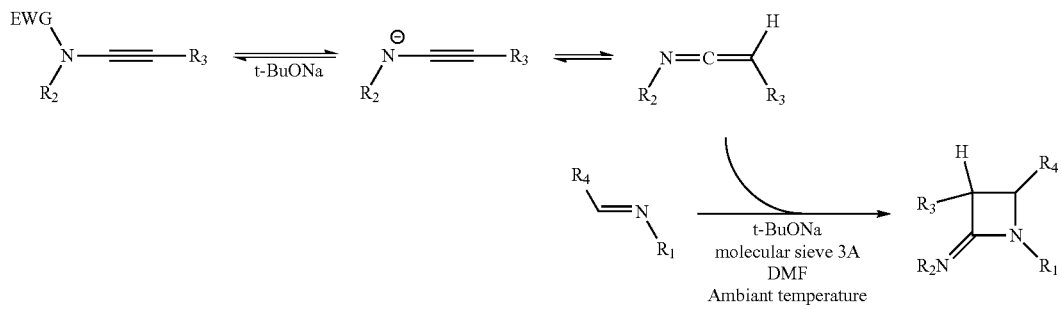

Although not all experimental conditions enabled to obtain such products, the advanced initial theory, which was unobvious by means, seems to have been proved, in particular experimental conditions thus enabling to provide new ways to obtain the sought compounds according to the present invention. These specific conditions comprise at least a base, an ynamide and an imine.

SUMMARY OF THE INVENTION

The subject matter of the present invention thus concerns a compound of formula (I):

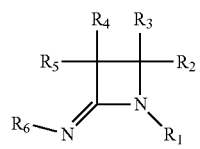

characterized in that:

$R_1$ represents a chemical moiety chosen in the group consisting of hydrogen, cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_3$-$C_{10}$ trialkylsilyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, $C_1$-$C_6$ alkyl, $C_3$-$C_7$ cycloalkyl, amino-$C_1$-$C_{10}$ alkoxy, (carboxylic acid)-$C_1$-$C_{10}$ alkoxy, (1,2 diol)-$C_2$-$C_{10}$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or nitro fragments, $R_2$, $R_3$, $R_4$ and $R_5$, independently one from each other, represent a chemical moiety chosen in the group consisting of hydrogen, halogen, nitro, cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_3$-$C_{10}$ trialkylsilyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or nitro fragments;

$R_6$ represents a chemical moiety chosen in the group consisting of hydrogen, halogen, nitro, cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_3$-$C_{10}$ trialkylsilyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or nitro fragments;

to the condition that:

$R_6$ is not a substituted or unsubstituted —$SO_2$-phenyl group such as a tosyl group;

when $R_6$ is a hydrogen atom:

$R_5$ and $R_4$ cannot be methyls, $R_3$ and $R_1$ cannot be phenyls and, $R_2$ cannot be a hydrogen atom;

$R_5$ and $R_2$ cannot be hydrogen atoms and $R_4$, $R_3$ and $R_1$ cannot be phenyls;

$R_5$, $R_3$, $R_1$ cannot be phenyls and, $R_4$ and $R_2$ cannot be hydrogen atoms;

when $R_6$ is a methyl:

$R_5$ and $R_4$ cannot be methyls, $R_3$ and $R_1$ cannot be phenyls and, $R_2$ cannot be a hydrogen atom;

$R_5$ and $R_2$ cannot be hydrogen atoms and $R_4$, $R_3$ and $R_1$ cannot be phenyls;

when $R_6$ is —$SO_2$-Me:

$R_5$, $R_3$ and $R_1$ cannot be phenyls, $R_4$ and $R_2$ cannot be hydrogen atoms; and when $R_6$ is a cyano:

the couple ($R_5$ and $R_4$) cannot be a methyl and a hydrogen atom, the couple ($R_2$ and $R_3$) cannot be phenyl and a hydrogen atom, and $R_1$ cannot be phenyl.

The subject matter of the present invention further concerns a compound of formula (I) above characterized in that:

$R_1$ represents a chemical moiety chosen in the group consisting of hydrogen, cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_3$-$C_{10}$ trialkylsilyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, hydroxyl (OH), nitro, cyano, formyl, $C_1$-$C_6$ alkyl, $C_3$-$C_7$ cycloalkyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio, and/or a $C_1$-$C_6$ alkoxy optionally substituted by a mono or polycyclic $C_5$-$C_{12}$ aryl group, and/or a bridging group of formula —O—$CH_2$—O— or —O—$CH_2CH_2$—O—;

$R_2$, $R_3$, $R_4$ and $R_5$, independently one from each other, represent a chemical moiety chosen in the group consisting of hydrogen, halogen, nitro, cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_3$-$C_{10}$ trialkylsilyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, COOH, —COO($C_1$-$C_6$ alkyl), $C_1$-$C_6$ alkyl, $C_3$-$C_7$ cycloalkyl, $C_1$-$C_6$ $N_3$-substituted alkyl, $C_1$-$C_6$ $NH_2$-substituted alkyl, $C_1$-$C_6$ alcohol, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio, a monocyclic $C_5$-$C_6$ aryl group optionally substituted by a $C_1$-$C_6$ alkyloxy group, and/or a COO($C_1$-$C_6$ alkyl) group wherein the alkyl is substituted by $NH_2$ or NHCOO($C_1$-$C_6$)alkyl or NHCOO($C_1$-$C_6$)alkyl(mono or polycyclic $C_5$-$C_{12}$)aryl;

$R_6$ represents a mono or polycyclic $C_5$-$C_{12}$ aryl fragment, wherein the aryl fragment is optionally substituted by one or several halogen atoms, cyano, nitro formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio fragments and/or a monocyclic $C_5$-$C_6$ aryl group optionally substituted by a $C_1$-$C_6$ alkyloxy group;

provided that at least two of $R_3$, $R_4$ and $R_5$ represent a hydrogen atom and $R_6$ is not a substituted or unsubstituted —$SO_2$-phenyl group such as a tosyl group. The subject matter of the present invention further concerns a compound of formula (I) above characterized in that:

$R_1$ represents a chemical moiety chosen in the group consisting of a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, hydroxyl (OH), nitro, cyano, formyl, $C_1$-$C_6$ alkyl, $O_3$-$C_7$ cycloalkyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, and/or a bridging group of formula —O—$CH_2$—O— or —O—$CH_2CH_2$—O—;

$R_2$, $R_3$, $R_4$ and $R_5$, independently one from each other, represent a chemical moiety chosen in the group consisting of a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, COOH, —COO($C_1$-$C_6$ alkyl), $C_1$-$C_6$ alkyl, $C_3$-$C_7$ cycloalkyl, $C_1$-$C_6$ $N_3$-substituted alkyl, $C_1$-$C_6$ $NH_2$-substituted alkyl, $C_1$-$C_6$ alcohol, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio, a monocyclic $C_5$-$C_6$ aryl group optionally substituted by a $C_1$-$C_6$ alkyloxy group and/or a COO($C_1$-$C_6$ alkyl) group wherein the alkyl is substituted by $NH_2$ or NHCOO($C_1$-$C_6$)alkyl or NHCOO($C_1$-$C_6$)alkyl(mono or polycyclic $C_5$-$C_{12}$)aryl;

$R_6$ represents a mono or polycyclic $C_5$-$C_{12}$ aryl or heteroaryl fragment, wherein the aryl or heteroaryl fragment is optionally substituted by one or several halogen atoms, cyano, nitro, formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio fragments and/or a monocyclic $C_5$-$C_6$ aryl group optionally substituted by a $C_1$-$C_6$ alkyloxy group;

provided that at least two of $R_3$, $R_4$ and $R_5$ represent a hydrogen atom and $R_6$ is not a substituted or unsubstituted —$SO_2$-phenyl group such as a tosyl group.

The subject matter of the present invention also concerns a method to prepare a compound of formula (I) above, however including the explicitly excluded compounds above, characterized in the following steps:

a. to a compound of formula (II):

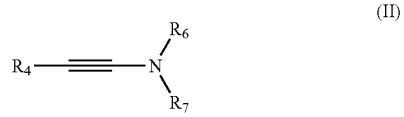

(II)

wherein $R_4$ and $R_6$ are as defined presently, including the excluded definitions above, and $R_7$ represents a leaving group such as amides, sulfonyles, or oxy-carbonyls, optionally, $R_6$—N—$R_7$ may form at least one ring wherein $R_6$ and $R_7$ directly linked one to each other and wherein said ring comprises from 3 to 12 atoms chosen from C, N, O, S, B and P (preferably chosen from C, N, O, S and B, even more preferably from C, N, O and S), substituted by at least one hydrogen, oxygen, nitrogen, hydroxyl, thiol, amine, cyano, $C_1$-$C_6$ alkyl, $C_3$-$C_6$ cycloalkyl, $C_1$-$C_6$ alkoxy, $C_1$-$C_6$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ haloalkylsulfinyl, $C_1$-$C_6$ haloalkylsulfonyl, $C_3$-$C_6$ trialkylsilyl, $C_1$-$C_6$ alkylsulfonyl, $C_5$-$C_{12}$ arylsulfonyl, formyl, $C_2$-$C_6$ alkylcarbonyl, $C_2$-$C_6$ alkenyl, $C_2$-$C_6$ alkynyl, $C_2$-$C_6$ alkenyloxy, $C_2$-$C_6$ alkynyloxy, $C_2$-$C_6$ alkenylthio, $C_2$-$C_6$ alkynylthio, $C_1$-$C_6$ haloalkyl, $C_2$-$C_6$ haloalkenyl, $C_2$-$C_6$ haloalkynyl, $C_2$-$C_6$ haloalkylcarbonyl, $C_1$-$C_6$ haloalkylthio, $C_2$-$C_6$ haloalkenyloxy, $C_2$-$C_6$ haloalkynyloxy, $C_2$-$C_6$ haloalkenylthio, $C_2$-$C_6$ haloalkynylthio, ($C_5$-$C_{12}$)-aryl-($C_1$-$C_6$)-alkyl or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or nitro fragments;

is added a compound of formula (III):

(III)

wherein $R_1$, $R_2$ and $R_3$ are as defined presently in the presence of a base B1, preferably $R_1$ is an electro-donating group and/or $R_2$ and/or $R_3$ are electron-withdrawing groups, preferably under microwaves;

b. an optional addition step of $R_5$, and/or $R_4$, as defined above for compound of formula (I) presently through a nucleophilic addition to the compound obtained in step (a), preferably with $R_5$—X, and/or $R_4$—X, wherein X is a halogen atom in the presence of a base B2;

c. retrieving the compound of formula (I) as defined presently.

The subject matter of the present invention also concerns a compound of formula (II) above as such, preferably as a synthesis intermediate or its equivalent carbene.

The subject matter of the present invention moreover concerns a compound of formula (I) as defined presently, including the explicitly excluded compounds above, as a drug.

The subject matter of the present invention furthermore concerns a use of a compound of formula (I) as defined presently including the explicitly excluded compounds above, as an inhibitor of a carbapenemase enzyme, preferably of a NDM-1 type, OXA-48 type or a KPC-type enzymes. The present invention further concerns a compound of formula (I) as defined presently including the explicitly excluded compounds above, fir use as an inhibitor of a carbapenemase enzyme, preferably of a NDM-1 type, OXA-48 type or a KPC-type enzymes.

Accordingly, the subject matter of the present invention concerns a compound of formula (I) as defined presently including the explicitly excluded compounds above, for its use as an antibiotic.

The subject matter of the present invention concerns a compound of formula (I) as defined presently including the explicitly excluded compounds above for its use in combination with an antibiotic.

Definitions

Generally speaking in the context of the present invention, unless specified differently, the expression "a compound of formula (I)" means any one of all variants of formula (I), including the excluded compounds above.

As customary in the art, in the present invention, "Me" stands for methyl (—$CH_3$), Bn stands for benzyl (—$CH_2$—$C_6H_5$) and Ph stands for phenyl (—$C_6H_5$).

The expressions "$C_1$-$C_{10}$ alkyl"/"alkyl" (i.e. the number of carbons in "alkyl" are not explicitly given) in the present invention mean a cyclic, linear or branched saturated aliphatic group with 1 to 10 carbon atoms if not otherwise specified. An alkyl group covered by the scope of the present invention is for example a group chosen from methyl, ethyl, propyl, butyl, tert-butyl, isopropyl, cyclopropyl, etc.

The expressions "$C_3$-$C_{10}$ cycloalkyl"/"cycloalkyl" (i.e. the number of carbons in "cycloalkyl" are not explicitly given) in the present invention mean a cyclic alkyl group with 3 to 10 carbon atoms if not otherwise specified. A cycloalkyl group covered by the scope of the present invention is for example a group chosen from cyclopropyl, cyclobutyl, cyclopentyl, cyclohexyl, methylcyclohexyl, etc.

The expression "$C_1$-$C_{10}$ thioalkyl" in the present invention means a $C_1$-$C_{10}$ alkyl moiety as presently defined, substituted by a thiol group, i.e. SH or a salt thereof.

The expression "$C_1$-$C_6$ alkylthio" in the present invention represents a "($C_1$-$C_6$ alkyl)-S—" group, i.e. an alkyl moiety with 1 to 6 carbon atoms, if not otherwise specified, as defined above linked to the rest of the molecule by a sulfur atom.

The expression "($C_1$-$C_6$)-alkylthio-($C_1$-$C_6$)-alkyl" in the present invention represents a "($C_1$-$C_6$)-alkylthio" as presently defined linked by its sulfur atom to any carbon atom of a "$C_1$-$C_6$ alkyl" as defined presently.

The expressions "$C_1$-$C_{10}$ alkoxy"/"$C_1$-$C_{10}$ alkyloxy" represent a "($C_1$-$C_6$ alkyl)-O—" group, i.e. an alkyl moiety with 1 to 10 carbon atoms, if not otherwise specified, as defined above, linked to the rest of the molecule by an oxygen atom. Examples of alkoxy groups covered by the scope of the present invention are methoxy, ethoxy groups etc.

The expression "(1,2 diol)-$C_2$-$C_{10}$ alkoxy" in the present invention represents an alkoxy group as defined above, wherein two adjacent carbon atoms are each linked to a hydroxyl group. The "1,2" does not limit the position to the first and second carbon atom attached to the rest of the molecule. Indeed, it is meant in the general context of the present invention that the hydroxyl groups are linked to two adjacent carbon, such as in position 2,3; 3,4; 4,5 . . . i.e. "n, n+1" wherein n is the position on the alkyl moiety, and thus n+1 cannot be superior to the total number of carbon atoms.

The expression "(carboxylic acid)-$C_1$-$C_{10}$ alkoxy" in the present invention represents an alkoxy group as defined above, wherein at least one carbon atom is linked to a fragment "COOH", "COO$^-$" or a salt thereof. Preferably, the "COOH" or "COO—" group or salt thereof is linked to the last carbon of the main linear chain of said $C_1$-$C_{10}$ alkoxy group.

The expression "(carboxylic ($C_1$-$C_6$)alkyl ester)-$C_1$-$C_{10}$ alkoxy" in the present invention represents an alkoxy group as defined above, wherein at least one carbon atom is linked to a carboxylic ester group of formula —COO—($C_1$-$C_6$) alkyl, through the carboxylic group. Preferably, the carboxylic ester group is linked to the last carbon of the main linear chain of said $C_1$-$C_{10}$ alkoxy group.

The expression "$C_1$-$C_6$ $N_3$-substituted alkyl" in the present invention represents an alkyl group as defined above, wherein at least one carbon atom is substituted by a $N_3$ group. Preferably, the $N_3$ group is linked to the last carbon of the main linear chain of said $C_1$-$C_6$ alkyl group.

The expression "$C_1$-$C_6$ $NH_2$-substituted alkyl" in the present invention represents an alkyl group as defined above, wherein at least one carbon atom is substituted by an amino ($NH_2$) group. Preferably, the $N_3$ group is linked to the last carbon of the main linear chain of said $C_1$-$C_6$ alkyl group.

The expression "$C_1$-$C_{10}$ alkylsulfinyl" in the present invention represents a "($C_1$-$C_{10}$ alkyl)-S(=O)—", i.e. an alkyl moiety of 1 to 10 carbon atoms, if not otherwise specified, as defined above, linked to the rest of the molecule by a sulphur atom which is mono oxidised.

The expression "$C_1$-$C_{10}$ alkylsulfonyl" in the present invention represents a "($C_1$-$C_{10}$ alkyl)-S(=O)$_2$—", i.e. an alkyl moiety of 1 to 10 carbon atoms, if not otherwise specified, as defined above, linked to the rest of the molecule by a sulphur atom which is oxidised twice.

The expression "($C_1$-$C_6$)-alkoxy-($C_1$-$C_6$)-alkyl" in the present invention represents a "($C_1$-$C_6$)-alkoxy" as defined above linked by its oxygen atom to any carbon atom of a "$C_1$-$C_6$ alkyl" group as defined above, the latter alkyl moiety being linked to the rest of the molecule.

The term "formyl" in the present invention represents a H—C(=O)— group.

The expression "$C_2$-$C_{10}$ alkylcarbonyl" in the present invention means an alkyl group as presently defined linked to a carbonyl, the carbonyl being itself linked to the rest of the molecule (e.g. of formula (I)).

The expression "$C_3$-$C_{10}$ trialkylsilyl" in the present invention means that three alkyl groups as defined above linked to one Si atom, the total number of carbon atoms amounting to 3 up to 10, said alkyl groups being itself being linked to the rest of the molecule.

The expressions "$C_5$-$C_{12}$ aryl"/"aryl" (i.e. the number of carbons in "aryl" are not explicitly given) in the present invention mean a cyclic (mono- or polycyclic) aromatic group comprising between 5 and 12 carbon atoms if not otherwise specified. Examples of aryl groups covered by the scope of the present invention are phenyl, naphthyl, etc.

The expression "monocyclic $C_5$-$C_{12}$ aryl" in the present invention represents an aryl fragment as defined here-above with only one hydrocarbon ring such as a phenyl fragment.

The expression "polycyclic $C_5$-$C_{12}$ aryl" in the present invention represents an aryl fragment as defined above with more than one hydrocarbon ring such as a naphtalene, anthracene, or a phenanthrene fragment.

The expression "heteroaryl" in the present invention means a cyclic (mono- or polycyclic) aromatic group comprising between 5 and 12 atoms which can be carbon atoms and/or heteroatoms such as nitrogen, oxygen or sulphur (e.g. the heteroaryl can comprise between 3 to 9 carbon atoms and between 1 and 5 heteroatoms). Examples of heteroaryl groups covered by the scope of the present invention are pyridine, thiophene, thiazole, imidazole, pyrazole, pyrrole, quinoline, indole, pyridazine, quinoxaline, dihydrobenzofuran etc.

The expression "monocyclic $C_5$-$C_{12}$ heteroaryl" in the present invention represents a heteroaryl fragment as defined here-above with only one multi-atom ring such as a pyridyl, thiazole, imidazole, etc. fragment.

The expression "polycyclic $C_5$-$C_{12}$ heteroaryl" in the present invention represents a heteroaryl fragment as defined above with more than one multi-atom ring such as a quinoline, indole, quinoxaline, etc. fragment.

As used herein, an "aryl or heteroaryl substituted by a bridging group" is understood as an aryl or heteroaryl group wherein the bridging group substitutes two carbons of the aryl or heteroaryl, and forms together with said aryl or heteroaryl a fused polycyclic group. For instance, if the aryl or heteroaryl is monocyclic, then said monocyclic aryl or heteroaryl substituted by a bridging group is a fused bicyclic group. In general, the bridging group substitutes two adjacent atom on the aryl (or heteroaryl) group. Examples of such aryl or heteroaryl substituted by a bridging group include 1,3-benzodioxole and 1,4-benzodioxane.

The expression "($C_5$-$C_{12}$)-aryl-($C_1$-$C_6$)-alkyl" in the present invention represents a "($C_5$-$C_{12}$)-aryl" as defined above linked to any carbon atom of a "$C_1$-$C_6$ alkyl" group as defined above, the alkyl moiety being linked to the rest of the molecule.

The expression "$C_5$-$C_{12}$ arylsulfonyl" in the present invention represents a "($C_5$-$C_{12}$ aryl)-S(=O)$_2$—", i.e. an aryl moiety of 5 to 12 carbon atoms as defined above linked to a sulphur atom which is oxidised twice.

The expressions "$C_2$-$C_{10}$ alkenyl"/"alkenyl" (i.e. the number of carbons in "alkenyl" are not explicitly given) in the present invention mean a cyclic, linear or branched aliphatic group with 2 to 10 carbon atoms, if not otherwise specified, comprising at least one unsaturation, i.e. at least one double bond. An alkenyl group covered by the scope of the present invention is for example a group chosen from ethylene, propyl-1-ene, propyl-2-ene, butyl-1-ene, butyl-2-ene, etc.

The expression "$C_2$-$C_{10}$ alkenylthio" in the present invention represents a "($C_2$-$C_{10}$ alkenyl)-S—", i.e. an alkenyl moiety of 2 to 10 carbon atoms, if not otherwise specified, as defined above linked to the rest of the molecule by a sulfur atom.

The expression "$C_2$-$C_{10}$ alkenyloxy", in the present invention represents a "($C_1$-$C_6$ alkenyl)-O—" group, i.e. an alkenyl moiety with 2 to 10 carbon atoms, if not otherwise specified, as defined above, linked to the rest of the molecule by an oxygen atom. Examples of alkenyloxy groups covered by the scope of the present invention are ethylenoxy, propyl-1-enoxy groups etc.

The expressions "$C_2$-$C_{10}$ alkynyl"/"alkynyl" (i.e. the number of carbons in "alkynyl" are not explicitly given) in the present invention mean a cyclic, linear or branched aliphatic group with 2 to 10 carbon atoms, if not otherwise specified, comprising at least one double in saturation, i.e. at least one triple bond. Examples of alkenyl groups covered by the scope of the present invention are acetylene, propyl-1-yne, propyl-2-yne, butyl-1-yne, butyl-2-yne, etc.

The expression "$C_2$-$C_{10}$ alkynyloxy", in the present invention means an alkynyl group defined above bound to an oxygen atom. Examples of alkynyloxy groups covered by the scope of the present invention are acetylenoxy, propyn-1-yloxy groups etc.

The expression "$C_2$-$C_{10}$ alkynylthio" in the present invention represents a "($C_2$-$C_{610}$ alkynyl)-S—", i.e. an alkynyl moiety of 2 to 10 carbon atoms, if not otherwise specified, as defined above linked to the rest of the molecule by a sulfur atom.

The expression "halogen atom" (equivalent to "halo" when used) in the present invention means at least one atom of fluorine, chlorine, bromine or iodine. For example a $C_1$-$C_{10}$ haloalkyl is an alkyl as presently defined substituted by at least one halogen atom. Examples of $C_1$-$C_{10}$ haloalkyl are —CH$_2$F$_1$, —CHF$_2$—, —CF$_3$, —CH$_2$Cl$_1$, —CHCl$_2$—, —CCl$_3$, —CH$_2$Br$_1$, —CHBr$_2$—, —CBr$_3$, —CH$_2$I$_1$, —CHI$_2$—, —CI$_3$, —CH$_2$—CH$_2$F$_1$, —CH$_2$—CHF$_2$—, —CH$_2$—CF$_3$, —CFH—CH$_3$—CF$_2$—CH$_3$, etc.

The expression "nitro" in the present invention means a NO$_2$ group.

Examples of "COO($C_1$-$C_6$ alkyl) group wherein the alkyl is substituted by NH$_2$ or NHCOO($C_1$-$C_6$)alkyl or NHCOO ($C_1$-$C_6$)alkyl(mono or polycyclic $C_5$-$C_{12}$)aryl" in the present invention are COOCH$_2$CH$_2$NHCOO$^t$Bu, COOCH$_2$CH$_2$NHCOO$^t$Bu and COOCH$_2$CH$_2$NH$_2$. Of course, in case of a NH$_2$ substituent, the amine may also be salified, for instance it may be a NH3$^+$ X$^-$ group, wherein X$^-$ represents an organic or inorganic anion with a single charge, such as for instance a halogenide (Cl$^-$, Br$^-$ or I$^-$ in particular) or a ($C_1$-$C_6$)alkyl-COO— or ($C_1$-$C_6$)haloalkyl-COO—, in particular CH$_3$COO$^-$ or CF$_3$COO$^-$.

The expression "leaving group" in the context of the present invention represents a molecular fragment or an atom departing from the molecule it initially belonged to, with typically a pair of electrons being torn off said molecule. Such "leaving groups" according to the present invention, can be chosen in the group consisting of amides (e.g. acetamide), sulfonyles (e.g. tosylate, mesylates), oxy-carbonyls (i.e. carboxylates), carbamates (e.g. Boc), dinitrogen (N$_2$$^+$), perfluoroalkylsulfonates (triflate), halogens (i.e. F, Cl, Br, I), amines, thiolates, phosphates, phenoxides. Preferably the "leaving groups" of the present invention are chosen in the group consisting of amides (e.g. acetamide), sulfonyles (e.g. tosylate, mesylates), oxy-carbonyls (i.e. carboxylates), carbamates (e.g. Boc). In a particular embodiment of the present invention, the leaving group is comprised in at least one molecular ring formed by R$_6$—N—R$_7$ of formula (II). In this latter case, the ring formed can comprise e.g. lactames, oxazolidinone, or even sultames.

An "electron-withdrawing group" ("EWG") means in the context of the present invention that the fragments is an electron attracting fragment, such as para-halogenophenyl, a CF$_3$, a phenyl, a fragment comprising a carbonyl, a cyano, a 3-pyridyl, a 4-methoxy phenyl, an amide, a sulphonamide, a carbamate, a 3,4,5-trimethoxyphenyl, a 4-methylthio-phenyl, a 4-ethoxy-phenyl, a 4-iodo-phenyl, a 4-nitro phenyl or a 4-[(2,3 diol)-propoxy]-phenyl fragment, preferably an inductive attracting fragment such as a para-halogenophenyl, a CF$_3$, a phenyl, a 3-pyridyl, a 4-methoxy phenyl, a 3,4,5-trimethoxyphenyl, a 4-methylthio-phenyl, a 4-ethoxy-phenyl, a 4-iodo-phenyl, a 4-nitro phenyl or a 4-[(2,3 diol)-propoxy]-phenyl fragment.

An "electro-donating group" ("EDG") means in the context of the present invention that the fragments is an electron enriching fragment, such as a 4-methoxy phenyl, a 3,4,5-trimethoxyphenyl, a 4-methylthio-phenyl, a 4-ethoxy-phenyl, a 4-iodo-phenyl, a 4-nitro phenyl or a 4-[(2,3 diol) propoxy]-phenyl fragment.

The term "microwaves" ("MW") according to the present invention comprises any electromagnetic radiation with wavelengths ranging from as long as a meter to as short to a millimeter, with frequencies between 300 MHz and 300 GHz. On a practical point of view, the frequency and other characteristics of the microwaves are adapted to the solvent used. For example, in the case of polar solvents like water, a frequency of 2.46 GHz will be used. Thus in the context of the present invention, the frequency of the MW used is preferably comprised between 1 and 10 GHz, more specifically from 2 to 3 GHz, such as 2.46 Ghz.

The expression "ambient temperature" ("AT") in the context of the present invention means a temperature comprised between 20 and 25° C.

The expression "nucleophilic addition", represents an addition reaction where a chemical compound with an electron-deficient or electrophilic double or triple bond, a π bond, reacts with electron-rich reactant, termed a nucleophile, with disappearance of the double bond and creation of two new single, i.e. σ, bonds.

The expression "synthesis intermediate", generally speaking, is a molecular entity that is formed from the reactants (or proceeding intermediates) and reacts further to give the directly observed products of a chemical reaction. The chemical reactions being stepwise, they take more than one elementary step to complete. Indeed, one of the aspects of the present invention concerns a process wherein e.g. the compound of formula (II) is used as a synthesis intermediate to produce the compound of formula (I). Moreover, in formula (I) when $R_4$ and/or $R_5$ is a hydrogen atom, this formula can be considered as a synthesis intermediate for the compound of formula (I) wherein $R_4$ and/or $R_5$ (which is/are different to a hydrogen) has been introduced through a nucleophilic addition (see step (b) of the process above).

The expression "carbapenemase enzyme" concerns enzymes of the β-lactamase type which have the capacity to hydrolyze cephalosporins, monobactams, carbapenems and penicillins. These β-lactamases, in particular carbapenemase, produced in bacteria are often responsible of the ineffectiveness of many β-lactams. Carbapenemase can be subdivised in A, B and D β-lactamases. Carbapenemase of class A include members of the SME, IMI, NMC, GES, and KPC families. The *Klebsiella pneumoniae* Carbapenemases (KPC) are the most prevalent, found mostly on plasmids (of *Klebsiella pneumoniae*). Carbapenemase of class D consist of OXA-type β-lactamases frequently detected in *Acinetobacter baumannii*. Class B carbapenemases, which are metallo-β-lactamases that contain zinc in the active site, belong to the IMP, VIM, SPM, GIM, and SIM families and have been primarily detected in *Pseudomonas aeruginosa* and have been incresingly reported in Enterobacteriaceae. Carbapenemases of NMD-1 type, OXA-48 and KPC are particularly aimed at by the subject matter of the present invention.

An "antibiotic activity" according to the present invention is the generic definition as understood by the skilled person, that is to say an effect of an "antibiotic agent". Such an "antibiotic agent" is a substance that kills, blocks or slows the growth of one or more bacteria.

By "growth" is included in the scope of the present invention any cell operation leading to a volumetric increase of the cell (i.e. of the bacterium), a cell division (of the bacteria) or a cell reproduction (of the bacteria).

The expression "pharmaceutical composition" in the present invention means any composition comprising an effective dose of a compound of the invention and at least one pharmaceutically acceptable excipient. Said excipients are selected, depending on the pharmaceutical form and the desired method of administration, from the usual excipients known by a person skilled in the art.

The expression "pharmaceutically acceptable addition salts" in the present invention means all the pharmaceutically acceptable salts of the compounds according to the invention are included within the scope of the invention, in particular the salts of weak acids and of weak bases, for example the hydrochloride salt, hydrobromide salt, trifluoacetate salt etc.

The terms "drug" or "medicament" are equivalent in the context of the present invention.

The expression "treatment" is intended to be directed towards all types of animals, preferably mammals, more preferably humans. In the case of a treatment of an animal which is not human kind, it will be referred to a veterinary treatment.

DETAILED DESCRIPTION

The subject matter of the present invention concerns a compound as presently defined characterized in that $R_6$ represents a chemical moiety chosen in the group consisting of $C_2$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_1$-$C_6$ thioalkyl, $C_1$-$C_6$ alkylthio, ($C_1$-$C_6$)-alkylthio-($C_1$-$C_6$)-alkyl, $C_1$-$C_6$ alkylsulfinyl, $C_1$-$C_6$ haloalkyl, $C_1$-$C_6$ haloalkoxy, ($C_1$-$C_6$)-haloalkoxy-($C_1$-$C_6$)-alkyl, $C_1$-$C_6$ haloalkylsulfinyl, $C_3$-$C_6$ trialkylsilyl, $C_2$-$C_6$ alkenyl, $C_2$-$C_6$ alkynyl, $C_2$-$C_6$ alkylcarbonyl, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenyl, $C_2$-$C_6$ haloalkynyl, $C_2$-$C_6$ haloalkylcarbonyl, $C_1$-$C_6$ haloalkylthio, $C_2$-$C_6$ haloalkenyloxy, $C_2$-$C_6$ haloalkynyloxy, $C_2$-$C_6$ haloalkenylthio, $C_2$-$C_6$ haloalkynylthio, ($C_5$-$C_{12}$)-aryl-($C_1$-$C_6$)-alkyl, mono or polycyclic $C_5$-$C_{12}$ aryl or mono or polycyclic $C_3$-$C_{12}$ heteroaryl fragment optionally substituted by one or several halogen atoms, nitro, cyano, formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$alkylsulfinyl, $C_1$-$C_6$ alkylsulfonyl, ($C_5$-$C_{12}$)-arylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or nitro fragments, or a monocyclic $C_5$-$C_6$ aryl group optionally substituted by a $C_1$-$C_6$ alkyloxy group preferably $R_6$ represents a mono or polycyclic $C_5$-$C_{12}$ aryl or heteroaryl fragment (preferably a phenyl fragment), wherein the aryl (phenyl) fragment is optionally substituted by one or several (notably 1 to 3) halogen atoms, cyano, formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or nitro fragments, or a monocyclic $C_5$-$C_6$ aryl group optionally substituted by a $C_1$-$C_6$ alkyloxy group, such as a phenyl group optionally substituted by a $C_1$-$C_6$ alkyloxy group, in particular a (4-)methoxyphenyl group. Even more preferably, $R_6$ represents a mono or polycyclic $C_5$-$C_{12}$ aryl fragment (such as a phenyl group), optionally substituted by one or several (notably 1 to 3) halogen atoms, $C_1$-$C_6$ haloalkyl or $C_1$-$C_6$ alkoxy. More preferably, $R_6$ is a monocyclic aryl fragment such as a phenyl group, optionally substituted by one or several (notably 1 to 3) halogen atoms, $C_1$-$C_6$ haloalkyl or $C_1$-$C_6$ alkoxy such as Cl, I, F, Br, $CF_3$ or OMe, especially for the method of preparation of the compound of formula (I) according to the present invention.

The subject matter of the present invention concerns a compound as presently defined, characterized in that $R_1$ represents an aryl or heteroaryl fragment, wherein the aryl or heteroaryl fragments are optionally substituted by
- one or several halogen atoms, hydroxyl (OH), nitro, cyano, formyl, $C_1$-$C_6$ alkyl, $C_3$-$C_7$ cycloalkyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, and/or
- a bridging group of formula —O—$CH_2$—O— or —O—$CH_2CH_2$—O—.

In a particular embodiment, $R_1$ represents an aryl or heteroaryl fragment optionally substituted by one or several (notably 1 to 3) $C_1$-$C_6$ alkoxy, $C_1$-$C_6$ thioalkyl, halogen, amino-$C_1$-$C_{10}$ alkoxy, (carboxylic acid)-$C_1$-$C_{10}$ alkoxy, (1,2 diol)-$C_2$-$C_{10}$ alkoxy, ($C_5$-$C_{12}$)-aryl-($C_1$-$C_6$)-alkyl ester and/or nitro fragments, especially for the method of preparation of the compound of formula (I) according to the present invention. Preferably, $R_1$ is an electro-donating group, especially for the method of preparation of the compound of formula (I) according to the present invention.

Preferably, the compounds of the present invention are characterized in that $R_1$ represents a monocyclic aryl fragment optionally substituted by
- one or several (notably 1 to 3) OH, $C_1$-$C_6$ alkyl, $C_2$-$C_6$ alkenyl, $C_1$-$C_6$ thioalkyl, halogen, amino-($C_1$-$C_{10}$ alkoxy), (carboxylic acid)-($C_1$-$C_{10}$ alkoxy), (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_5$-$C_{12}$)-aryl-($C_1$-$C_6$)-alkyl ester, nitro and/or a $C_1$-$C_6$ alkoxy group optionally substituted by a mono or polycyclic C5-C12 aryl group, and/or
- a bridging group of formula —O—$CH_2$—O— or —O—$CH_2CH_2$—O—, especially for the method of preparation of the compound of formula (I) according to the present invention.

More preferably, the compounds of the present invention are characterized in that $R_1$ represents a monocyclic aryl fragment optionally substituted by one or several (notably 1 to 3):
- OH,
- $C_1$-$C_6$ thioalkyl, in particular $SCH_3$,
- $C_2$-$C_6$ alkenyl, such as —CH=$CH_2$ (vinyl group),
- halogen, such as iodine,
- (carboxylic acid)-($C_1$-$C_{10}$ alkoxy), such as $OCH_2COOH$,
- (carboxylic ($C_1$-$C_6$)alkyl ester)-$C_1$-$C_{10}$ alkoxy, such as $OCH_2COOCH_3$, $OCH_2COOCH_2CH_3$ or $OCH_2COOC(CH_3)_3$, in particular $OCH_2COOC(CH_3)_3$,
- (1,2 diol)-$C_2$-$C_{10}$ alkoxy, such as $OCH_2CHOHCH_2OH$, —O—($C_1$-$C_6$)alkyl-O—($C_1$-$C_6$)alkyl-OH, such as $OCH_2CH_2OCH_2CH_2OH$, and/or
- $C_1$-$C_6$ alkoxy group optionally substituted by a mono or polycyclic $C_5$-$C_{12}$ aryl group, such as $OCH_3$, $OCH_2CH_3$, $OCH_2Ph$, and/or
- a bridging group of formula —O—$CH_2$—O— or —O—$CH_2CH_2$—O—, even more preferably, $R_1$ represents a monocyclic aryl fragment optionally substituted by
- one or several (notably 1 to 3) OH, $C_1$-$C_6$ alkyl, $C_1$-$C_6$ thioalkyl, halogen, amino-($C_1$-$C_{10}$ alkoxy), (carboxylic acid)-($C_1$-$C_{10}$ alkoxy), (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_5$-$C_{12}$)-aryl-($C_1$-$C_6$)-alkyl ester, nitro and/or a $C_1$-$C_6$ alkoxy group optionally substituted by a mono or polycyclic $C_5$-$C_{12}$ aryl group, and/or
- a bridging group of formula —O—$CH_2$—O— or —O—$CH_2CH_2$—O—, especially for the method of preparation of the compound of formula (I) according to the present invention.

More preferably, the compounds of the present invention are characterized in that $R_1$ represents a monocyclic aryl fragment optionally substituted by one or several (notably 1 to 3):
- OH,
- $C_1$-$C_6$ thioalkyl, in particular $SCH_3$
- halogen, such as iodine,
- (carboxylic ($C_1$-$C_6$)alkyl ester)-$C_1$-$C_{10}$ alkoxy, such as $OCH_2COOCH_3$, $OCH_2COOCH_2CH_3$ or $OCH_2COOC(CH_3)_3$, in particular $OCH_2COOC(CH_3)_3$,
- (1,2 diol)-$C_2$-$C_{10}$ alkoxy, such as $OCH_2CHOHCH_2OH$, —O—($C_1$-$C_6$)alkyl-O—($C_1$-$C_6$)alkyl-OH, such as $OCH_2CH_2OCH_2CH_2OH$, and/or
- $C_1$-$C_6$ alkoxy group optionally substituted by a mono or polycyclic $C_5$-$C_{12}$ aryl group, such as $OCH_3$, $OCH_2CH_3$, $OCH_2Ph$, and/or a bridging group of formula —O—$CH_2$—O— or —O—$CH_2CH_2$—O—,
especially for the method of preparation of the compound of formula (I) according to the present invention.

For instance, the compounds of the present invention are characterized in that $R_1$ represents a monocyclic aryl fragment optionally substituted by one or several $C_1$-$C_6$ alkoxy, $C_1$-$C_6$ thioalkyl, halogen, amino-($C_1$-$C_{10}$ alkoxy), (carboxylic acid)-($C_1$-$C_{10}$ alkoxy), (1,2 diol)-$C_2$-$C_{10}$ alkoxy, ($C_5$-$C_{12}$)-aryl-($C_1$-$C_6$)-alkyl ester and/or nitro fragments, especially for the method of preparation of the compound of formula (I) according to the present invention.

In a particular embodiment, the compounds of the present invention are characterized in that $R_1$ represents a phenyl fragment optionally substituted by one or several $C_1$-$C_6$ alkoxy, $C_1$-$C_6$ thioalkyl, halogen, amino-$C_1$-$C_{10}$ alkoxy, (carboxylic acid)-$C_1$-$C_{10}$ alkoxy, (2,3 diol)-propoxy, ($C_5$-$C_{12}$)-aryl-($C_1$-$C_6$)-alkyl ester and/or nitro fragments, especially for the method of preparation of formula (I) according to the present invention.

In a particular embodiment, the compounds of the present invention are characterized in that $R_1$ represents an aryl fragment substituted by one or several iodine atoms, methoxy, methylthio, ethyloxy, amino-$C_1$-$C_{10}$ alkoxy, (carboxylic acid)-$C_1$-$C_{10}$ alkoxy, (2,3 diol)-propoxy, ($C_5$-$C_{12}$)-aryl-($C_1$-$C_6$)-alkyl ester and/or nitro fragments, especially for the method of preparation of the compound of formula (I) according to the present invention.

Yet in a particular embodiment, the compounds of the present invention are characterized in that $R_1$ represents an aryl fragment substituted by one or three methoxy groups, one methylthio group, one ethoxy group, one iodine atom, one (2,3 diol)-propoxy group and/or nitro fragments, especially for the method of preparation of the compound of formula (I) according to the present invention.

In a preferred embodiment, the compounds of the present invention are characterized in that $R_1$ represents a phenyl fragment substituted by one or three methoxy groups, one methylthio group, one ethoxy group, one iodine atom, one (2,3 diol)-propoxy group and/or nitro fragments, especially for the method of preparation of the compound of formula (I) according to the present invention.

In a particular embodiment, the compounds of the present invention are characterized in that $R_1$ represents a phenyl fragment, a 4-methoxy phenyl, a 3,4,5-trimethoxyphenyl, a 4-methylthio-phenyl, a 4-ethoxy-phenyl, a 4-iodo-phenyl, a 4-nitro phenyl or a 4-[(2,3 diol)-propoxy]-phenyl fragments, especially for the method of preparation of the compound of formula (I) according to the present invention.

In another embodiment, the compounds of the present invention are characterized in that $R_1$ represents a monocyclic aryl fragment optionally substituted by one or several halogen atoms, $C_1$-$C_6$ alkoxy and/or $C_1$-$C_6$ thioalkyl fragments, especially for the method of preparation of the compound of formula (I) according to the present invention.

Preferably, the compounds of the present invention are characterized in that $R_1$ represents a phenyl fragment optionally substituted by one or several halogen atoms, $C_1$-$C_6$ alkoxy and/or $C_1$-$C_6$ thioalkyl fragments, especially for the method of preparation of the compound of formula (I) according to the present invention.

In a particular embodiment of the present invention are characterized, the compounds of the present invention are characterized in that $R_1$ represents an aryl fragment substituted by one or several iodine atoms, methoxy, methylthio and/or ethyloxy fragments, especially for the method of preparation of the compound of formula (I) according to the present invention.

In a particular embodiment of the present invention are characterized, the compounds of the present invention are characterized in that $R_1$ represents an aryl fragment substituted by one iodine atom, one or three methoxy groups, one methylthio group and/or one ethoxy group, especially for the method of preparation of the compound of formula (I) according to the present invention.

In a preferred embodiment, the compounds of the present invention are characterized in that $R_1$ represents a phenyl fragment substituted by one iodine atom, one or three methoxy groups, one ethoxy group, one benzyloxy group, one $OCH_2COOH$ group, one $OCH_2COOC(CH_3)_3$ group, one $OCH_2CH_2OCH_2CH_2OH$ group, one OH group, one $OCH_2CH_2OCH_2CH_2OH$ group, one methylthio group and/or one bridging group of formula —O—$CH_2$—O— or —O—$CH_2CH_2$—O—, even more preferably, by one iodine atom, one or three methoxy groups, one ethoxy group, one benzyloxy group, one $OCH_2COOC(CH_3)_3$ group, one $OCH_2CH_2OCH_2CH_2OH$ group, one OH group, one $OCH_2CH_2OCH_2CH_2OH$ group, one methylthio group and/or one bridging group of formula —O—$CH_2$—O— or —O—$CH_2CH_2$—O—, especially for the method of preparation of the compound of formula (I) according to the present invention.

In a preferred embodiment, the compounds of the present invention are characterized in that $R_1$ represents a phenyl fragment substituted by one iodine atom, one or three methoxy groups, one methylthio group and/or one ethoxy group, especially for the method of preparation of the compound of formula (I) according to the present invention.

In a particularly preferred embodiment, the compounds of the present invention are characterized in that $R_1$ represents a phenyl fragment, a 4-hydroxyphenyl, a 4-methoxyphenyl, a 2-methoxyphenyl, a 3-methoxyphenyl, a 3,4-dimethoxyphenyl, a 3,4,5-trimethoxyphenyl, a 4-methylthio-phenyl, a 4-ethoxy-phenyl, a 4-benzyloxy-phenyl, a 1,3-benzodioxole, a 1,4-benzodioxane, a 4-[(2,3 diol)-propoxy]-phenyl, a 4-phenoxyacetic acid, a tert-butyl 4-(phenoxy)acetate, a 4-(bis(2-hydroxyethyl)ether)phenyl or a 4-iodo-phenyl, even more preferably, $R_1$ represents a phenyl fragment, a 4-hydroxyphenyl, a 4-methoxy phenyl, a 2-methoxy phenyl, a 3-methoxy phenyl, a 3,4-dimethoxyphenyl, a 3,4,5-trimethoxyphenyl, a 4-methylthio-phenyl, a 4-ethoxy-phenyl, a 4-benzyloxy-phenyl, a 1,3-benzodioxole, a 1,4-benzodioxane, a 4-[(2,3 diol)-propoxy]-phenyl, a tert-butyl 4-(phenoxy)acetate, a 4-(bis(2-hydroxyethyl)ether)phenyl or a 4-iodo-phenyl, especially for the method of preparation of the compound of formula (I) according to the present invention.

In another particularly preferred embodiment, the compounds of the present invention are characterized in that $R_1$ represents a phenyl fragment, a 4-methoxy phenyl, a 3,4,5-trimethoxyphenyl, a 4-methylthio-phenyl, a 4-ethoxy-phenyl or a 4-iodo-phenyl, especially for the method of preparation of the compound of formula (I) according to the present invention.

The subject matter of the present invention also concerns a compound as defined presently, characterized in that $R_2$ and/or $R_3$ represent a $C_1$-$C_6$ haloalkyl, a $C_1$-$C_6$ alkoxy, a $C_1$-$C_6$ thioalkyl, a $C_1$-$C_6$ acyl, nitro and/or a cyano fragments, a mono or polycyclic aryl or heteroaryl fragment optionally substituted by one or several halogen atoms, nitro, cyano, formyl, COOH, —COO($C_1$-$C_6$ alkyl), $C_1$-$C_6$ alkyl, $C_3$-$C_7$ cycloalkyl, $C_1$-$C_6$ $N_3$-substituted alkyl, $C_1$-$C_6$ $NH_2$-substituted alkyl, $C_1$-$C_6$ alcohol, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio, a monocyclic $C_5$-$C_6$ aryl group optionally substituted by a $C_1$-$C_6$ alkyloxy group and/or a COO($C_1$-$C_6$ alkyl) group wherein the alkyl is substituted by $NH_2$ or NHCOO($C_1$-$C_6$)alkyl or NHCOO($C_1$-$C_6$)alkyl(mono or polycyclic $C_5$-$C_{12}$)aryl (preferably the alkyl in the COO($C_1$-$C_6$ alkyl) group is substituted by NHCOO($C_1$-$C_6$)alkyl or NHCOO($C_1$-$C_6$)alkyl(mono or polycyclic $C_5$-$C_{12}$)aryl), especially for the method of preparation of the compound of formula (I) according to the present invention.

In particular, $R_2$ and/or $R_3$ represent a $C_1$-$C_6$ haloalkyl, a $C_1$-$C_6$ alkoxy, a $C_1$-$C_6$ thioalkyl, a $C_1$-$C_6$ acyl, nitro and/or a cyano fragments, a mono or polycyclic aryl or heteroaryl fragment optionally substituted by one or several halogen atoms, especially for the method of preparation of the compound of formula (I) according to the present invention.

Preferably $R_2$ (and/or $R_3$) is an electron-enricher group, i.e. an electron donating group, especially for the method of preparation of the compound of formula (I) according to the present invention. Specifically, in one embodiment of the present invention, the compounds of the present invention are characterized in that $R_2$ and/or $R_3$ represent at least one electron-withdrawing group chosen in the list consisting of a para-halogenophenyl, a $CF_3$, a phenyl, a fragment comprising a carbonyl such as an acyl, a cyano, a 3-pyridyl, a 4-methoxy phenyl, a 3,4,5-trimethoxyphenyl, a 4-methylthio-phenyl, a 4-ethoxy-phenyl, a 4-iodo-phenyl, a 4-nitro phenyl or a 4-[(2,3 diol)-propoxy]-phenyl fragment.

Preferably, the compound of the present invention is characterized in that $R_2$ and/or $R_3$ represent a monocyclic aryl, monocyclic heteroaryl or polycyclic aryl fragment optionally substituted by one or several (notably 1 to 3) halogen atoms, $C_1$-$C_6$ $NH_2$-substituted alkyl, COOH, —COO($C_1$-$C_6$ alkyl), $C_1$-$C_6$ $N_3$-substituted alkyl, $C_1$-$C_6$ haloalkyl, $C_1$-$C_6$ alcohol, $C_1$-$C_6$ alkoxy, $C_1$-$C_6$ thioalkyl, $C_1$-$C_6$ acyl, $C_2$-$C_6$ alkenyl, nitro, cyano, a monocyclic $C_5$-$C_6$ aryl group optionally substituted by a $C_1$-$C_6$ alkyloxy group (such as a phenyl group substituted by a $C_1$-$C_6$ alkyloxy group, preferably a methoxy group) and/or a COO($C_1$-$C_6$ alkyl) group wherein the alkyl is substituted by $NH_2$ or NHCOO($C_1$-$C_6$)alkyl or NHCOO($C_1$-$C_6$)alkyl(mono or polycyclic $C_5$-$C_{12}$)aryl, fragments (preferably the alkyl in the COO($C_1$-$C_6$ alkyl) group is substituted by NHCOO($C_1$-$C_6$)alkyl or NHCOO($C_1$-$C_6$)alkyl(mono or polycyclic $C_5$-$C_{12}$)aryl), especially for the method of preparation of the compound of formula (I) according to the present invention.

Preferably, the compound of the present invention is characterized in that $R_2$ and/or $R_3$ represent a monocyclic aryl, monocyclic heteroaryl or polycyclic aryl fragment optionally substituted by one or several halogen atoms, $C_1$-$C_6$ alkoxy, $C_1$-$C_6$ thioalkyl, $C_1$-$C_6$ acyl, nitro and/or cyano fragments, especially for the method of preparation of the compound of formula (I) according to the present invention.

For example, the compound of the present invention is characterized in that $R_2$ and/or $R_3$ represent a phenyl fragment, a pyridyl fragment, or a naphthalene fragment, optionally substituted by one or several (notably 1 to 3) halogen atoms, COOH, —COO($C_1$-$C_6$ alkyl), $C_1$-$C_6$ $N_3$-substituted alkyl, $C_1$-$C_6$ $NH_2$-substituted alkyl, $C_1$-$C_6$ haloalkyl, $C_1$-$C_6$ alcohol, $C_1$-$C_6$ alkoxy, $C_1$-$C_6$ thioalkyl, $C_2$-$C_6$ alkenyl, $C_1$-$C_6$ acyl, nitro, cyano, a monocyclic $C_5$-$C_6$ aryl group optionally substituted by a $C_1$-$C_6$ alkyloxy group (such as a phenyl group substituted by a $C_1$-$C_6$ alkyloxy group, preferably a methoxy group) and/or a COO($C_1$-$C_6$ alkyl) group wherein the alkyl is substituted by $NH_2$ or NHCOO($C_1$-$C_6$)alkyl or NHCOO($C_1$-$C_6$)alkyl(mono or polycyclic $C_5$-$C_{12}$) aryl, fragments (preferably the alkyl in the COO($C_1$-$C_6$ alkyl) group is substituted by NHCOO($C_1$-$C_6$)alkyl or NHCOO($C_1$-$C_6$)alkyl(mono or polycyclic $C_5$-$C_{12}$)aryl), especially for the method of preparation of the compound of formula (I) according to the present invention.

In particular, the compound of the present invention is characterized in that $R_2$ and/or $R_3$ represent a phenyl fragment, a pyridyl fragment, or a naphthalene fragment, optionally substituted by one or several halogen atoms, $C_1$-$C_6$ alkoxy, $C_1$-$C_6$ thioalkyl, $C_1$-$C_6$ acyl, nitro and/or cyano fragments, especially for the method of preparation of the compound of formula (I) according to the present invention.

More preferably, the compound of the present invention is characterized in that $R_2$ and/or $R_3$ represent an aryl fragment substituted by one or several chlorine atoms, fluorine atoms, methoxy, COOH, COOCH$_3$, COOC(CH$_3$)$_3$, COOCH$_2$CH$_2$NH$_2$, COOCH$_2$CH$_2$NHCOOC(CH$_3$)$_3$, CH$_2$OH, CH$_2$N$_3$, CH$_2$NH$_2$, CH$_2$Cl, vinyl, nitro, 4-methoxyphenyl, and/or cyano fragments, even more preferably by one or several chlorine atoms, fluorine atoms, methoxy, COOH, COOCH$_3$, COOC(CH$_3$)$_3$, COOCH$_2$CH$_2$NHCOOC(CH$_3$)$_3$, CH$_2$N$_3$, CH$_2$Cl, nitro and/or cyano fragments, especially for the method of preparation of the compound of formula (I) according to the present invention.

Even more preferably, the compound of the present invention is characterized in that $R_2$ and/or $R_3$ represent an aryl fragment substituted by one or several chlorine atoms, fluorine atoms, methoxy fragments, nitro and/or cyano fragments, especially for the method of preparation of the compound of formula (I) according to the present invention.

Yet more preferably, the compound of the present invention is characterized in that $R_2$ and/or $R_3$ represent an aryl fragment optionally substituted by one, two or three methoxy groups, one methylthio group, one ethoxy group, one iodine atom, one fluorine atom, one or two chlorine atom, one (2,3 diol)-propoxy group, one COOH group, one vinyl group, one COOCH$_3$ group, one COOC(CH$_3$)$_3$ group, one COOCH$_2$CH$_2$NH$_2$ group, one COOCH$_2$CH$_2$NHCOOC(CH$_3$)$_3$ group, one CH$_2$OH group, one CH$_2$N$_3$ group, one CH$_2$NH$_2$ group, one CH$_2$Cl group, one 4-methoxyphenyl, and/or nitro fragments, even more preferably by one, two or three methoxy groups, one methylthio group, one ethoxy group, one iodine atom, one fluorine atom, one or two chlorine atom, one (2,3 diol)-propoxy group, one COOH group, one COOCH$_3$ group, one COOC(CH$_3$)$_3$ group, one COOCH$_2$CH$_2$NHCOOC(CH$_3$)$_3$ group, one CH$_2$N$_3$ group, one CH$_2$Cl group, and/or nitro fragments, especially for the method of preparation of the compound of formula (I) according to the present invention.

Yet more preferably, the compound of the present invention is characterized in that $R_2$ and/or $R_3$ represent an aryl fragment substituted by one or three methoxy groups, one methylthio group, one ethoxy group, one iodine atom, one (2,3 diol)-propoxy group and/or nitro fragments, especially for the method of preparation of the compound of formula (I) according to the present invention.

Yet more preferably, the compound of the present invention is characterized in that $R_2$ and/or $R_3$ represent:

a phenyl fragment optionally substituted by one methoxy group, one fluorine atom, one or two chlorine atoms, one vinyl group, one COOH group, one COOCH$_3$ group, one COOC(CH$_3$)$_3$ group, one COOCH$_2$CH$_2$NH$_2$ group, one COOCH$_2$CH$_2$NHCOOC(CH$_3$)$_3$ group, one CH$_2$OH group, one CH$_2$N$_3$ group, one CH$_2$NH$_2$ group, one CH$_2$Cl group and/or one 4-methoxyphenyl, preferably a phenyl fragment optionally substituted by one methoxy group, one fluorine atom, one or two chlorine atoms, one COOH group, one COOCH$_3$ group, one COOC(CH$_3$)$_3$ group, one COOCH$_2$CH$_2$NHCOOC(CH$_3$)$_3$ group, one CH$_2$N$_3$ group, and/or one CH$_2$Cl group, a naphthalene fragment, or a pyridine fragment, especially for the method of preparation of the compound of formula (I) according to the present invention.

In a more preferred embodiment, the compound of the present invention is characterized in that $R_2$ and/or $R_3$ represent an phenyl fragment substituted by one or three methoxy groups, one methylthio group, one ethoxy group, one iodine atom, one (2,3 diol)-propoxy group and/or nitro fragments, especially for the method of preparation of the compound of formula (I) according to the present invention.

In a preferred embodiment, the compound of the present invention is characterized in that $R_2$ and/or $R_3$ represent a phenyl fragment, a 2-naphthalenyl fragment, a 3-pyridyl fragment, a 4-methoxy phenyl, a 3,4,5-trimethoxyphenyl, a 4-(hydroxymethyl)-phenyl, a 4-methylthio-phenyl, a 4-ethoxy-phenyl, a 4-iodo-phenyl, a 4-fluoro-phenyl, a 4-chloro-phenyl, a 3,5-dichloro-phenyl, a 4-nitro phenyl a 4-[(2,3 diol)-propoxy]-phenyl, a 4-(chloromethyl)-phenyl, a 4-(azidomethyl)-phenyl, a 4-(aminomethyl)-phenyl, a 4-carboxylic acid-phenyl (i.e a

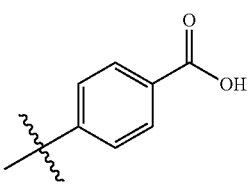 [SMILES: *c1ccc(C(=O)O)cc1]

group), a methyl 4-carboxylate-phenyl (i.e a

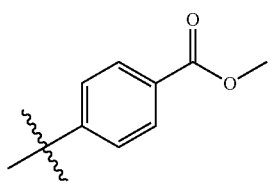 [SMILES: *c1ccc(C(=O)OC)cc1]

group), a tert-butyl 4-carboxylate-phenyl (i.e a

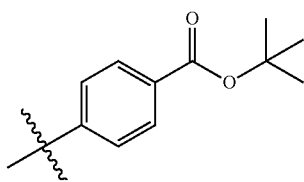 [SMILES: *c1ccc(C(=O)OC(C)(C)C)cc1]

group), a

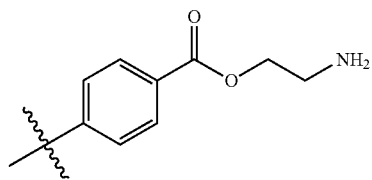 [SMILES: *c1ccc(C(=O)OCCN)cc1]

group (especially as the ammonium salt, such as the corresponding trifluoroacetate ammonium salt) or a

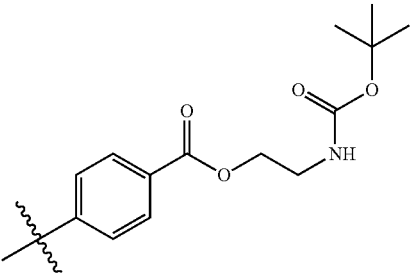 [SMILES: *c1ccc(C(=O)OCCNC(=O)OC(C)(C)C)cc1]

group, a 4-vinylphenyl group

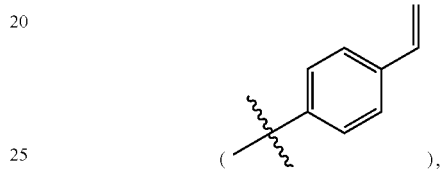

or a 4-(4-methoxyphenyl)-phenyl group,

preferably a phenyl fragment, a 2-naphthalenyl fragment, a 3-pyridyl fragment, a 4-methoxy phenyl, a 3,4,5-trimethoxyphenyl, a 4-methylthio-phenyl, a 4-ethoxy-phenyl, a 4-iodo-phenyl, a 4-fluoro-phenyl, a 4-chloro-phenyl, a 3,5-dichloro-phenyl, a 4-nitro phenyl a a 4-[(2,3 diol)-propoxy]-phenyl, a 4-(chloromethyl)-phenyl, a 4-(azidomethyl)-phenyl, a 4-carboxylic acid-phenyl (i.e a

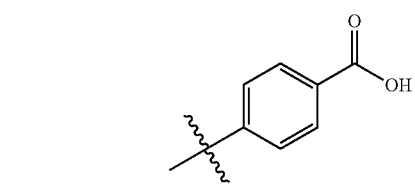 [SMILES: *c1ccc(C(=O)O)cc1]

group), a methyl 4-carboxylate-phenyl (i.e a

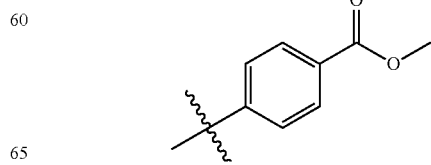

group), a tert-butyl 4-carboxylate-phenyl (i.e a

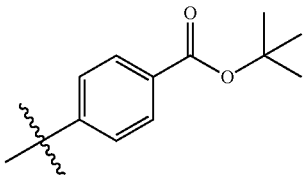 [SMILES: *c1ccc(C(=O)OC(C)(C)C)cc1]

group), or a

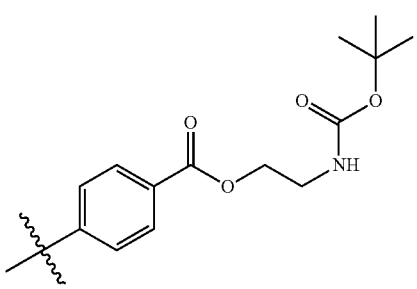 [SMILES: *c1ccc(C(=O)OCCNC(=O)OC(C)(C)C)cc1]

group, especially for the method of preparation of the compound of formula (I) according to the present invention.

In a preferred embodiment, the compound of the present invention is characterized in that $R_2$ and/or $R_3$ represent a phenyl fragment, a 3-pyridyl fragment, a 4-methoxy phenyl, a 3,4,5-trimethoxyphenyl, a 4-methylthio-phenyl, a 4-ethoxy-phenyl, a 4-iodo-phenyl, a 4-nitro phenyl or a 4-[(2,3 diol)-propoxy]-phenyl, especially for the method of preparation of the compound of formula (I) according to the present invention.

In another preferred embodiment, the compound of the present invention is characterized in that $R_2$ and/or $R_3$ represent a phenyl fragment, a 2-naphthalenyl fragment, a 3-pyridyl fragment, a 4-methoxy phenyl, a 3,4,5-trimethoxyphenyl, a 4-(hydroxymethyl)-phenyl, a 4-methylthio-phenyl, a 4-ethoxy-phenyl, a 4-iodo-phenyl, a 4-fluoro-phenyl, a 4-chloro-phenyl, a 3,5-dichloro-phenyl, a 4-(chloromethyl)-phenyl, a 4-(azidomethyl)-phenyl, a 4-(aminomethyl)-phenyl, a 4-vinylphenyl group, a 4-(4-methoxyphenyl)-phenyl group, a 4-carboxylic acid-phenyl, a methyl 4-carboxylate-phenyl, a tert-butyl 4-carboxylate-phenyl a

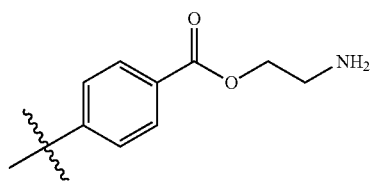 [SMILES: *c1ccc(C(=O)OCCN)cc1]

group (especially as the ammonium salt, such as the corresponding trifluoroacetate ammonium salt) or a

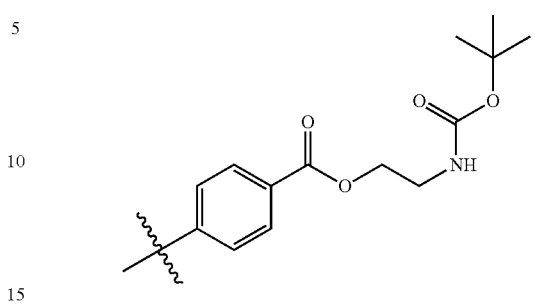

fragment, preferably a phenyl fragment, a 2-naphthalenyl fragment, a 3-pyridyl fragment, a 4-methoxy phenyl, a 3,4,5-trimethoxyphenyl, a 4-methylthio-phenyl, a 4-ethoxy-phenyl, a 4-iodo-phenyl, a 4-fluoro-phenyl, a 4-chloro-phenyl, a 3,5-dichloro-phenyl, a 4-(chloromethyl)-phenyl, a 4-(azidomethyl)-phenyl, a 4-carboxylic acid-phenyl, a methyl 4-carboxylate-phenyl, a tert-butyl 4-carboxylate-phenyl or a

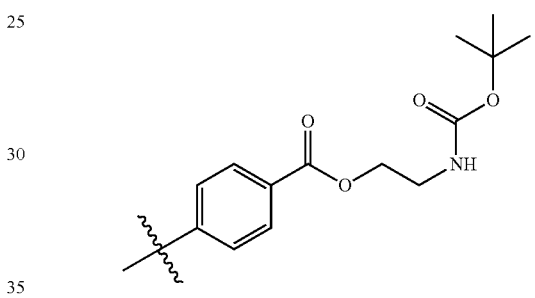

fragment, especially for the method of preparation of the compound of formula (I) according to the present invention.

Preferably, $R_2$ (and/or $R_3$) is an electron-withdrawing group and $R_1$ is an electro-donating group, especially for the method of preparation of the compound of formula (I) according to the present invention.

In another embodiment, the compound of the present invention is characterized in that $R_2$ and/or $R_3$ represent monocyclic aryl, monocyclic heteroaryl or polycyclic aryl fragments optionally substituted by one or several halogen atoms and/or $C_1$-$C_6$ alkoxy fragments, especially for the method of preparation of the compound of formula (I) according to the present invention.

More preferably, the compound of the present invention is characterized in that $R_2$ and/or $R_3$ represent a phenyl fragment optionally substituted by one or several halogen atoms and/or $C_1$-$C_6$ alkoxy fragments, especially for the method of preparation of the compound of formula (I) according to the present invention.

Even more preferably, the compound of the present invention is characterized in that $R_2$ and/or $R_3$ represent a monocyclic aryl, monocyclic heteroaryl or polycyclic aryl substituted by one or several chlorine atoms, fluorine atoms and/or methoxy fragments, especially for the method of preparation of the compound of formula (I) according to the present invention.

Yet more preferably, the compound of the present invention is characterized in that $R_2$ and/or $R_3$ represent a phenyl or pyridyl fragment optionally substituted by one or several chlorine atoms, fluorine atoms and/or methoxy fragments, especially for the method of preparation of the compound of formula (I) according to the present invention.

In a more preferred embodiment, the compound of the present invention is characterized in that $R_2$ and/or $R_3$ represent a phenyl, a 3-pyridyl, a 4-methoxy phenyl, a 4-fluoro-phenyl, a 4-chloro phenyl, or a 3,5 dichlorophenyl, especially for the method of preparation of the compound of formula (I) according to the present invention.

Preferably, $R_1$ is an electro-donating group and $R_2$ (and/or $R_3$) is an electron-withdrawing group, especially for the method of preparation of the compound of formula (I) according to the present invention.

The subject matter of the present invention also concerns a compound as presently defined, characterized in that at least one of $R_3$, $R_4$ and $R_5$ represents a hydrogen atom, especially for the method of preparation of the compound of formula (I) according to the present invention.

Preferably, the compound of the present invention is characterized in that at least two of $R_3$, $R_4$ and $R_5$ represent a hydrogen atom, especially for the method of preparation of the compound of formula (I) according to the present invention.

Preferably, the compound of the present invention is characterized in that $R_3$, $R_4$ and $R_5$ represent hydrogen atoms, especially for the method of preparation of the compound of formula (I) according to the present invention. In this embodiment, $R_2$ preferably represents a monocyclic aryl, monocyclic heteroaryl or polycyclic aryl fragment optionally substituted by one or several (notably 1 to 3) halogen atoms, COOH, —COO($C_1$-$C_6$ alkyl), $C_1$-$C_6$ $N_3$-substituted alkyl, $C_1$-$C_6$ haloalkyl, $C_1$-$C_6$ alcohol, $C_1$-$C_6$ alkoxy, $C_1$-$C_6$ thioalkyl, $C_1$-$C_6$ acyl, nitro, cyano and/or a COO($C_1$-$C_6$ alkyl) group wherein the alkyl is substituted by $NH_2$ or NHCOO($C_1$-$C_6$)alkyl or NHCOO($C_1$-$C_6$)alkyl (mono or polycyclic $C_5$-$C_{12}$)aryl, fragments, especially for the method of preparation of the compound of formula (I) according to the present invention. In particular, $R_2$ represents:
- a phenyl fragment optionally substituted by one methoxy group, one fluorine atom, one or two chlorine atoms, one COOH group, one COOCH$_3$ group, one COOC(CH$_3$)$_3$ group, one COOCH$_2$CH$_2$NH$_2$ group, one COOCH$_2$CH$_2$NHCOOC(CH$_3$)$_3$ group, one CH$_2$OH group, one CH$_2$N$_3$ group, and/or one CH$_2$Cl group, preferably a phenyl fragment optionally substituted by one methoxy group, one fluorine atom, one or two chlorine atoms, one COOH group, one COOCH$_3$ group, one COOC(CH$_3$)$_3$ group, one COOCH$_2$CH$_2$NHCOOC(CH$_3$)$_3$ group, one CH$_2$N$_3$ group, and/or one CH$_2$Cl group,
- a naphthalene fragment, or
- a pyridine fragment.

In this embodiment, $R_6$ represents a mono or polycyclic $C_5$-$C_{12}$ aryl fragment, optionally substituted by one or several (notably 1 to 3) halogen atoms, $C_1$-$C_6$ haloalkyl or $C_1$-$C_6$ alkoxy, more preferably, $R_6$ is a monocyclic aryl fragment such as a phenyl group, optionally substituted by one or several (notably 1 to 3) halogen atoms, $C_1$-$C_6$ haloalkyl or $C_1$-$C_6$ alkoxy such as Cl, I, F, Br, CF$_3$ or OMe. Even more preferably, in this specific embodiment, the compounds of the present invention are preferably characterized in that $R_1$ represents a monocyclic aryl fragment optionally substituted by
- one or several (notably 1 to 3) OH, $C_1$-$C_6$ alkyl, $C_1$-$C_6$ thioalkyl, halogen, amino-($C_1$-$C_{10}$ alkoxy), (carboxylic acid)-($C_1$-$C_{10}$ alkoxy), (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_5$-$C_{12}$)-aryl-($C_1$-$C_6$)-alkyl ester, nitro and/or a $C_1$-$C_6$ alkoxy group optionally substituted by a mono or polycyclic $C_5$-$C_{12}$ aryl group, and/or
- a bridging group of formula —O—CH$_2$—O— or —O—CH$_2$CH$_2$—O—.

The subject matter of the present invention moreover concerns a compound as presently defined, especially for the method of preparation of the compound of formula (I) according to the present invention, characterized in that:
$R_1$ represents a fragment chosen from the group consisting of phenyl, 4-methoxy phenyl, 4-ethoxy-phenyl, 4-nitro phenyl, 3,4,5-trimethoxyphenyl, 4-methylthio-phenyl, 4-iodo-phenyl; and
$R_2$ and/or $R_3$ represent a fragment chosen from the group consisting of phenyl, 4-methoxy phenyl, 4-formylphenyl, 4-nitro phenyl, 4-fluorophenyl, 4-chlorophenyl, 2,4-dichlorophenyl, naphtyl, indolyl, furanyl, pyridyl, thiophenyl.

The subject matter of the present invention preferably concerns a compound as presently defined, especially for the method of preparation of the compound of formula (I) according to the present invention, characterized in that:
$R_1$ represents a fragment chosen from the group consisting of phenyl, 4-methoxy phenyl, a 3,4,5-trimethoxyphenyl, 4-methylthio-phenyl, 4-ethoxy-phenyl or 4-iodo-phenyl
$R_2$ and/or $R_3$ represent a fragment chosen from the group consisting of phenyl, 4-methoxy phenyl, 4-formylphenyl, 4-nitro phenyl, 4-fluorophenyl, 4-chlorophenyl, 2,4-dichlorophenyl, naphtyl, indolyl, furanyl, pyridyl, thiophenyl.

It is understood that the present invention concerns any combination of particular and/or preferred embodiments of $R_1$, $R_2$, $R_3$, $R_4$, $R_5$ and $R_6$.

In a particular embodiment, especially for the method of preparation of the compound of formula (I) according to the present invention, the subject matter of the present invention concerns the molecules of the following structure:

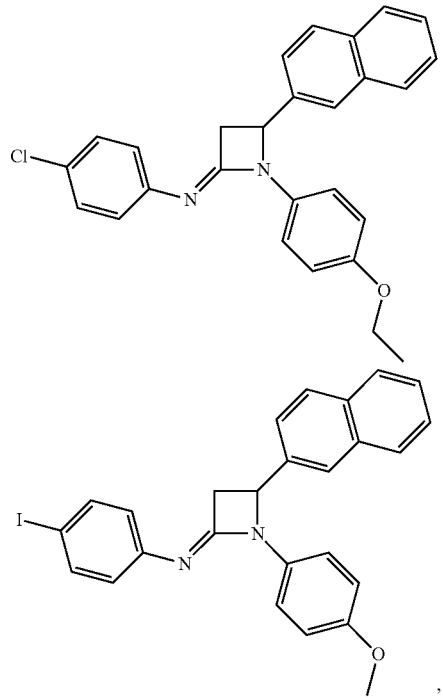

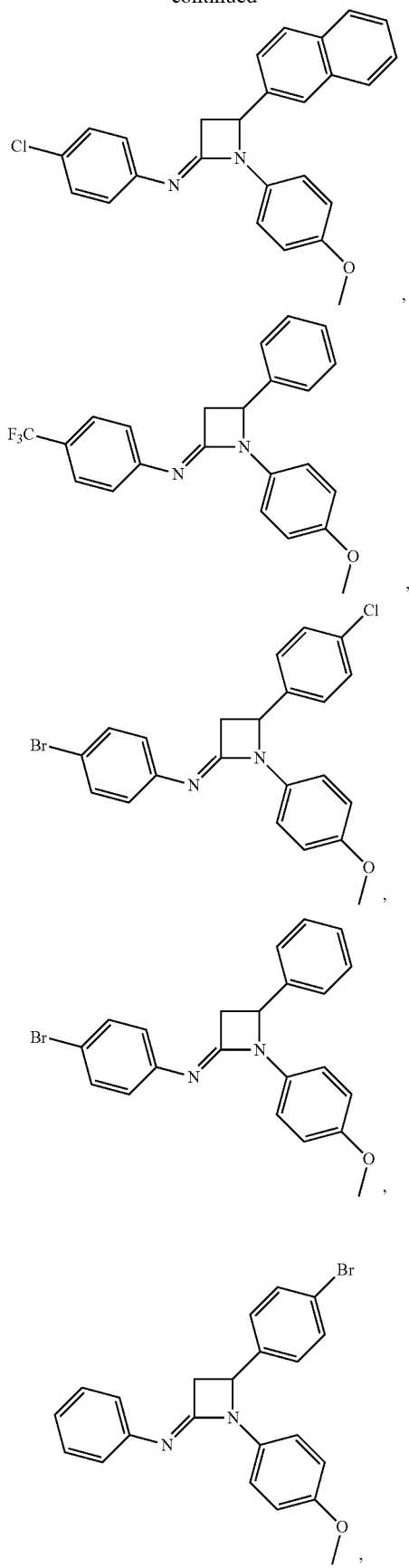
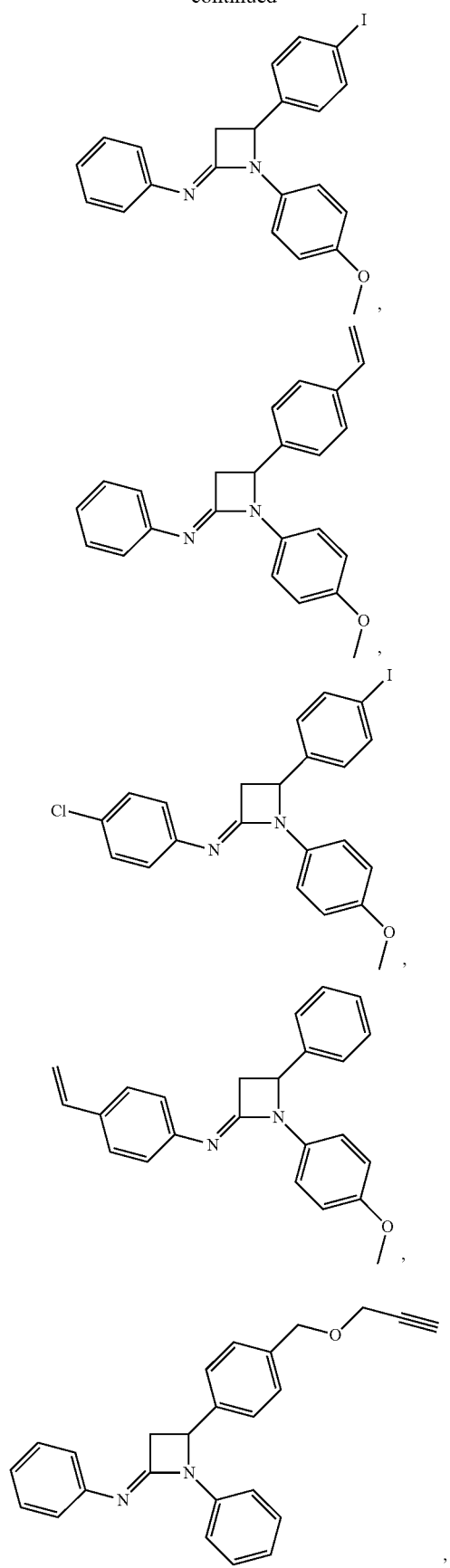

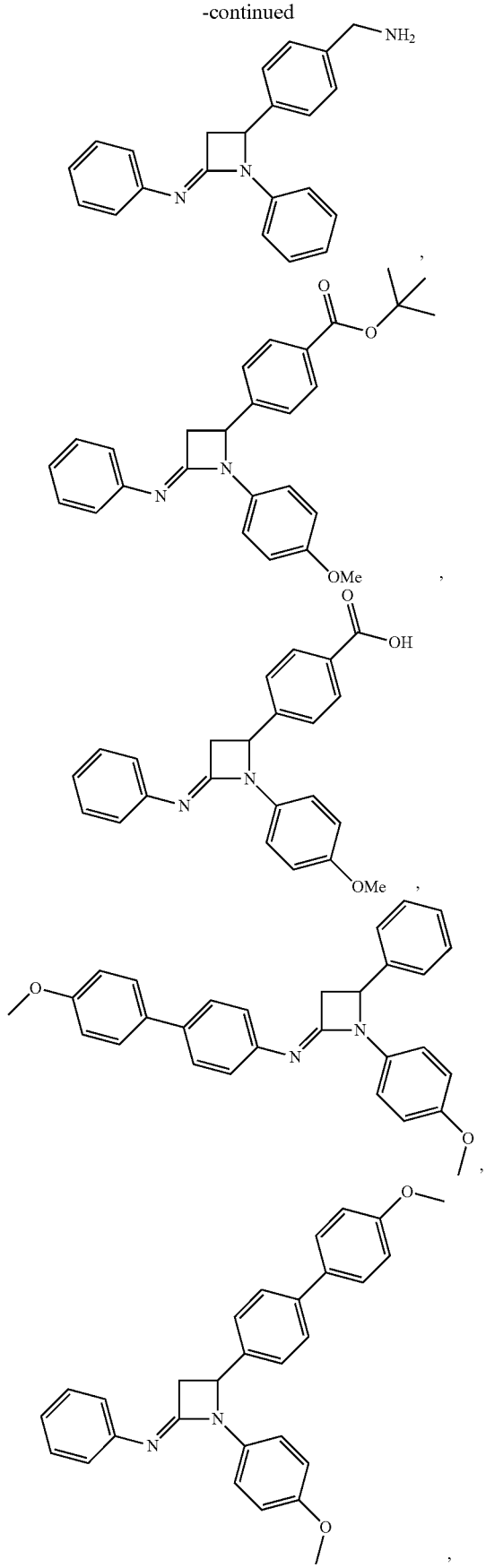
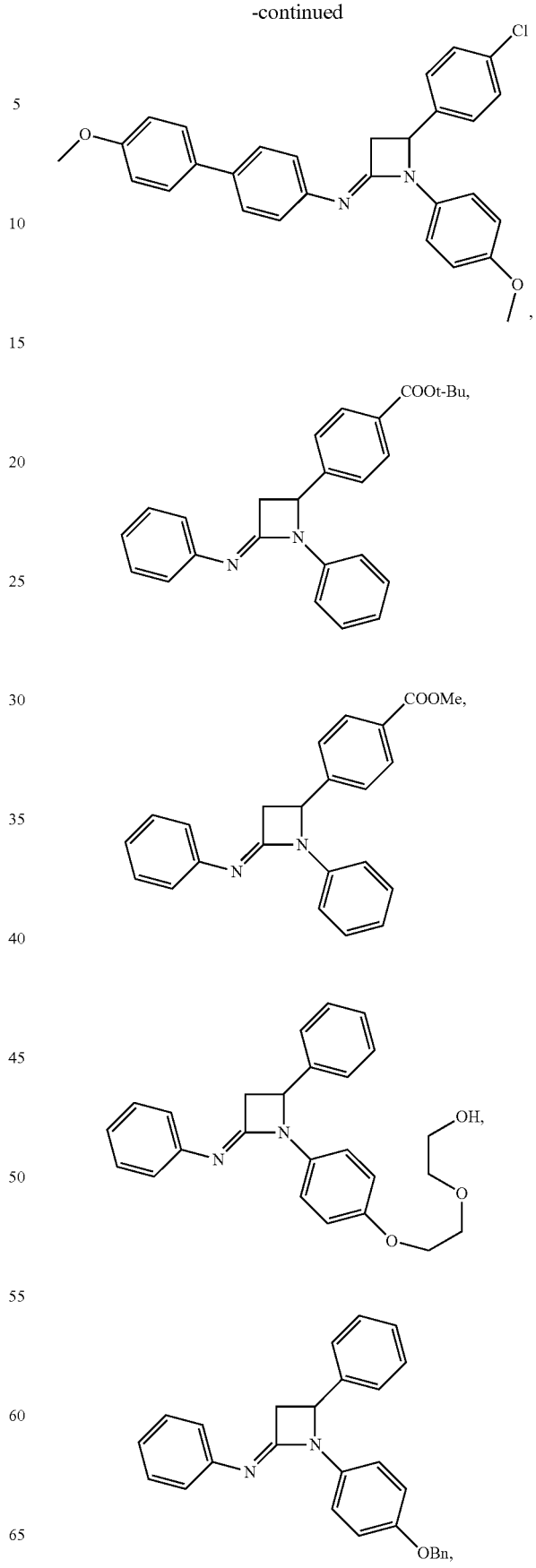

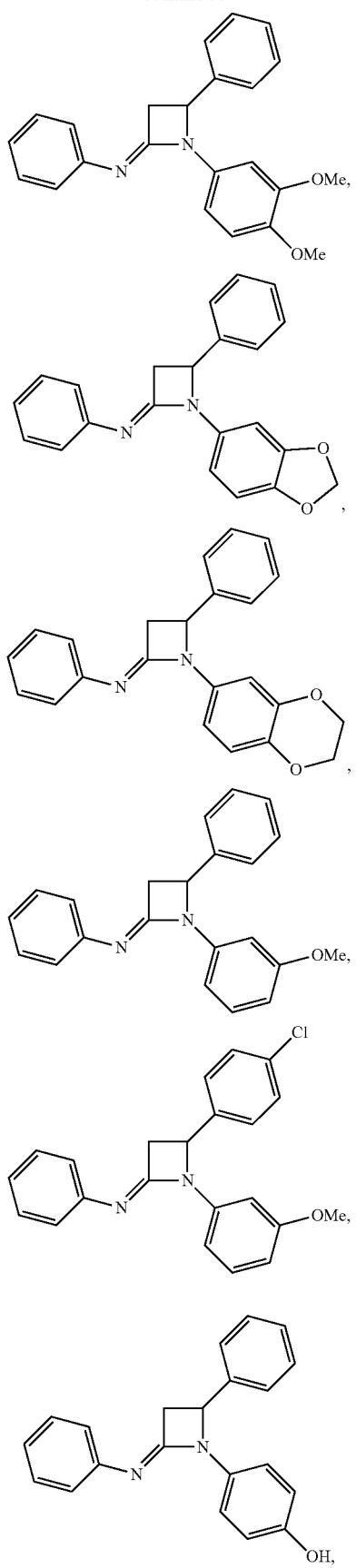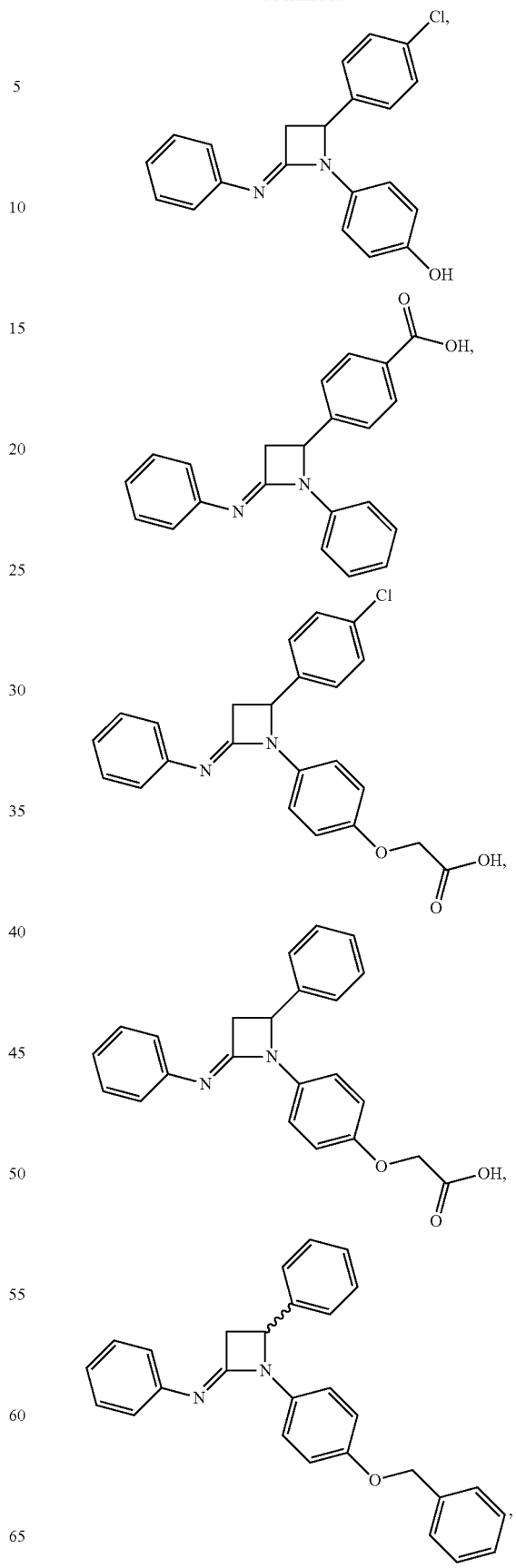

37
-continued
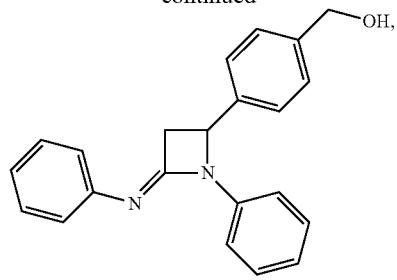
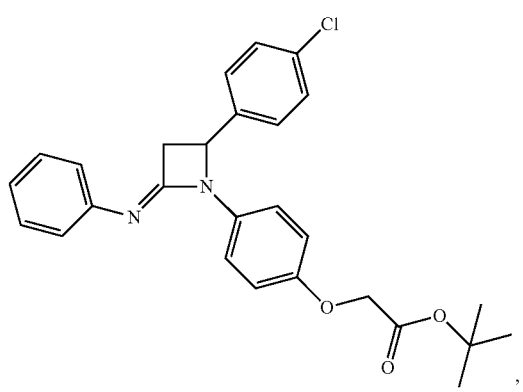
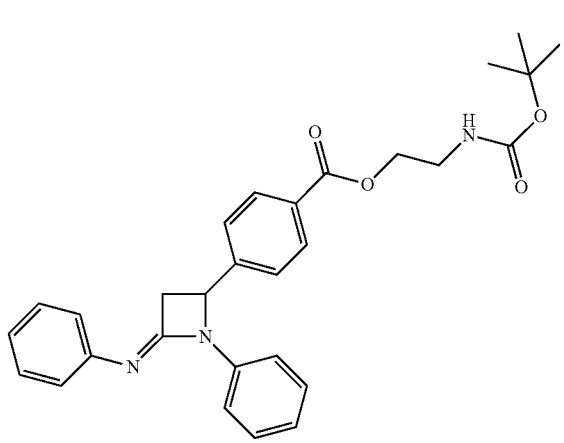
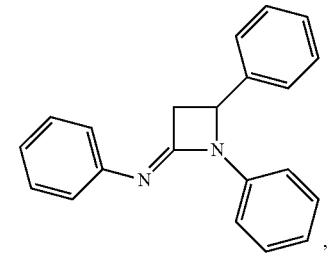
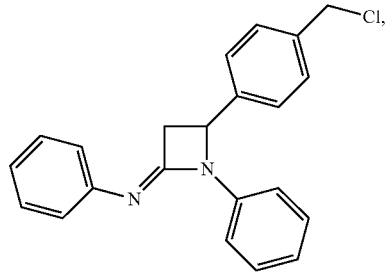
38
-continued
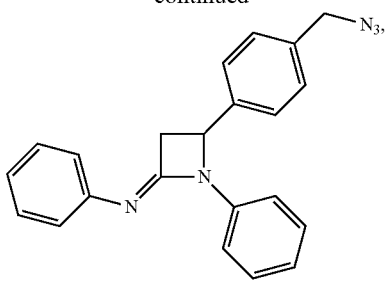
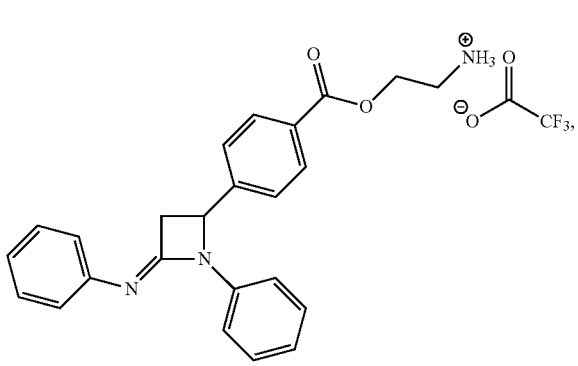
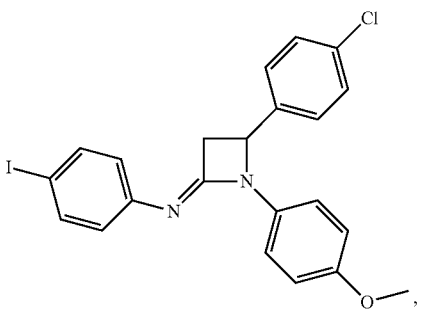
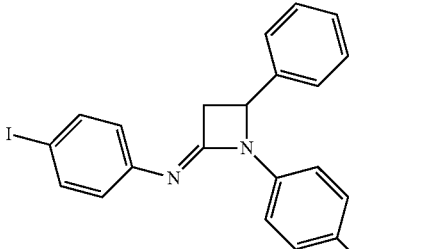
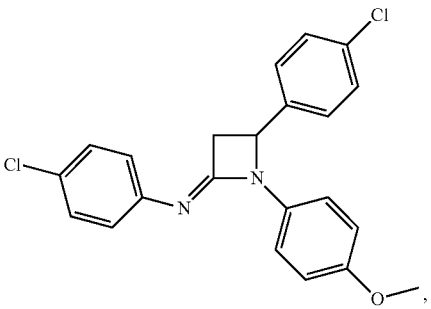

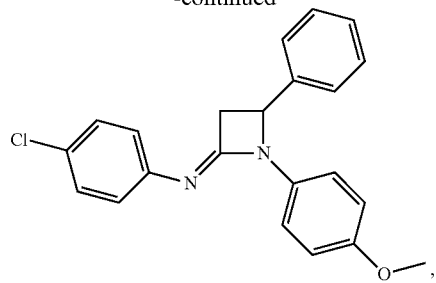
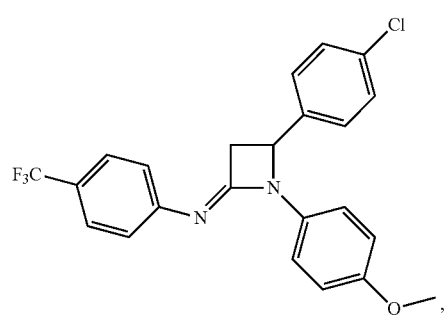
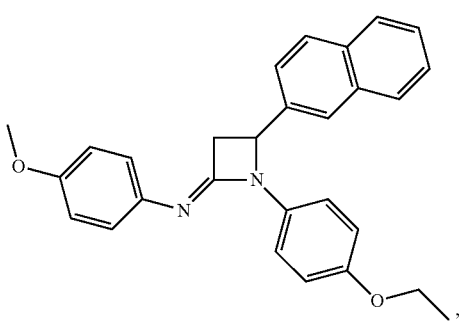
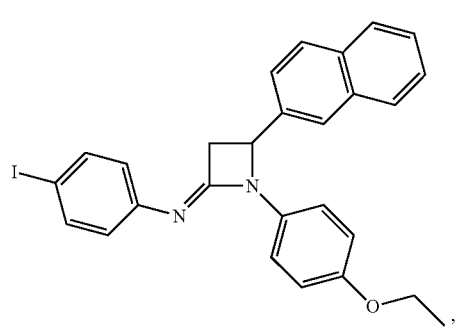
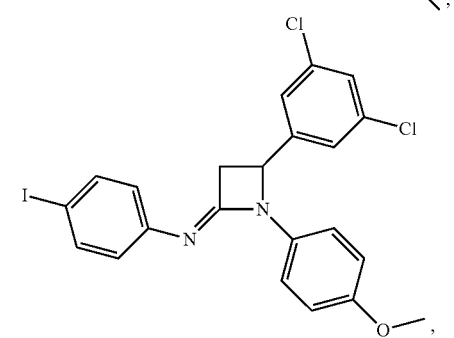
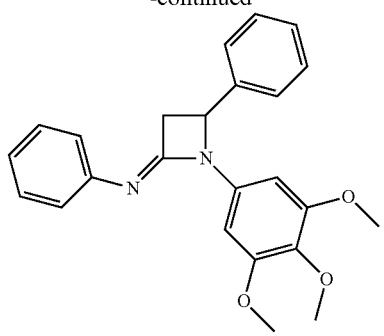
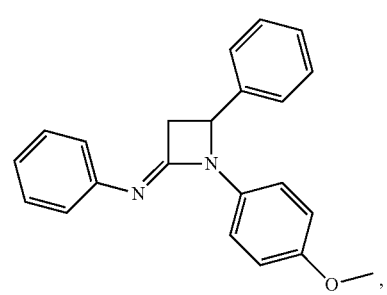
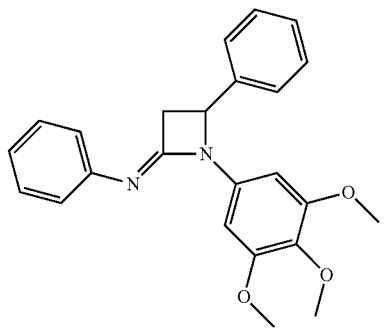
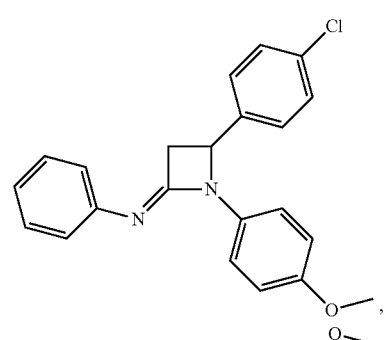
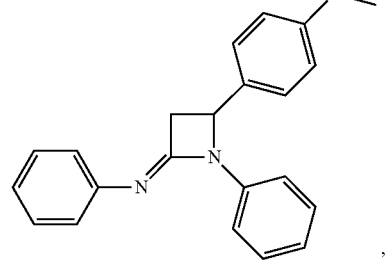

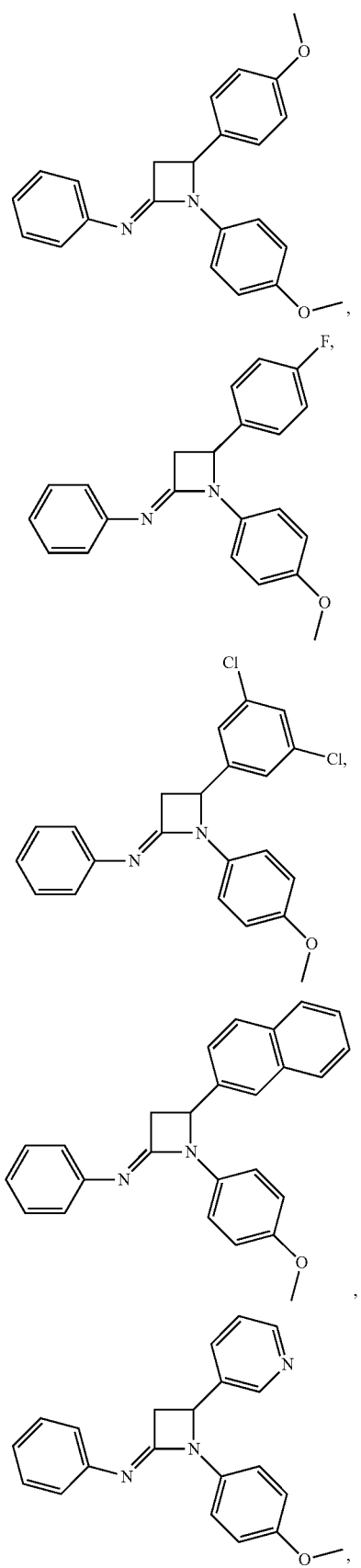
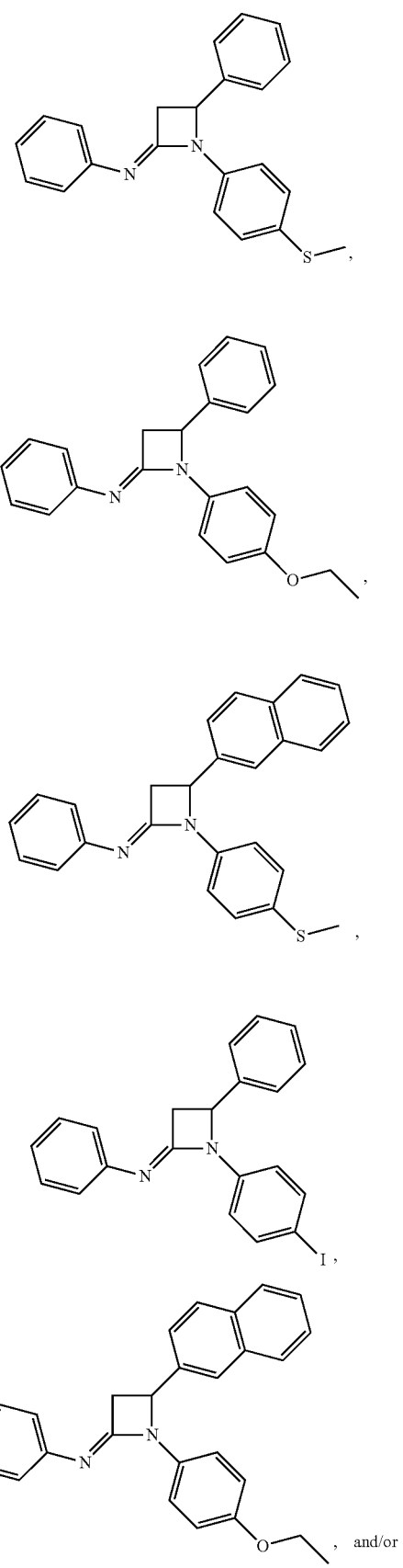

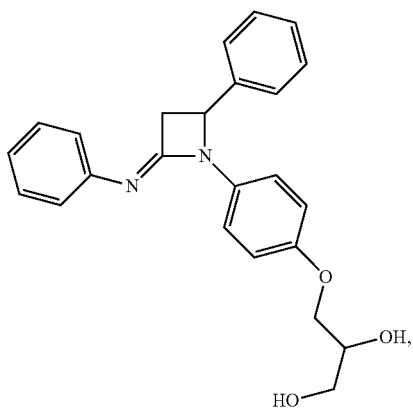
salts or solvates thereof.
More specifically, especially for the method of preparation of the compound of formula (I) according to the present invention, the subject matter of the present invention concerns the molecules of the following structure:
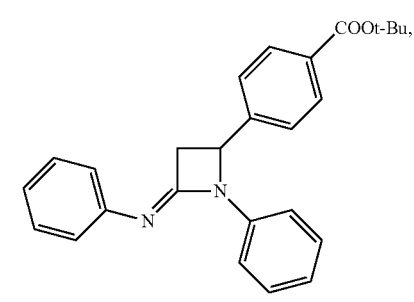
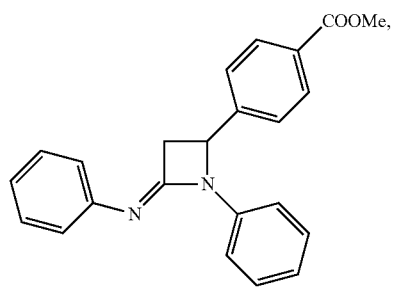
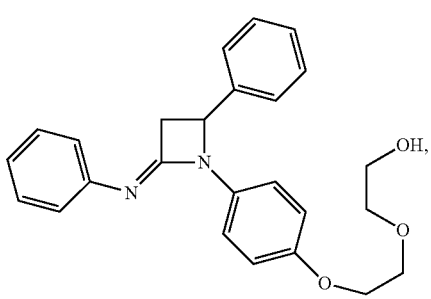
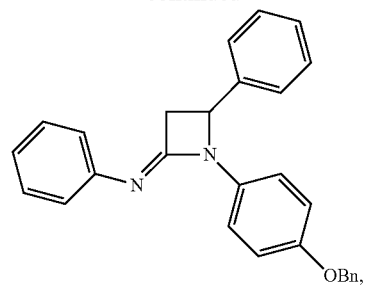
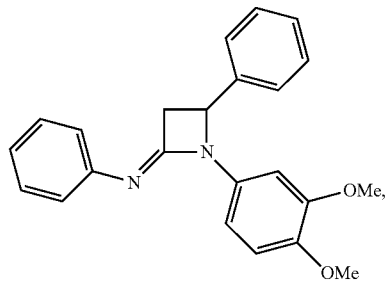
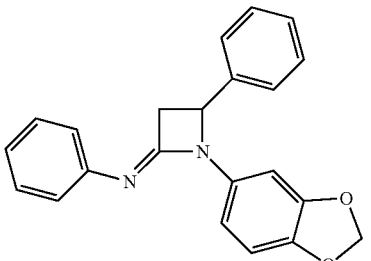
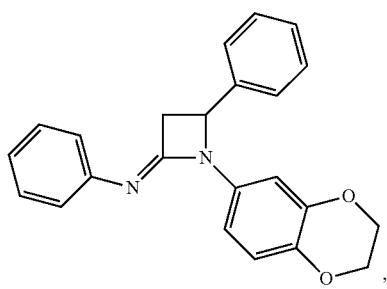
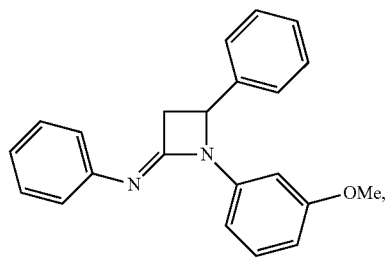

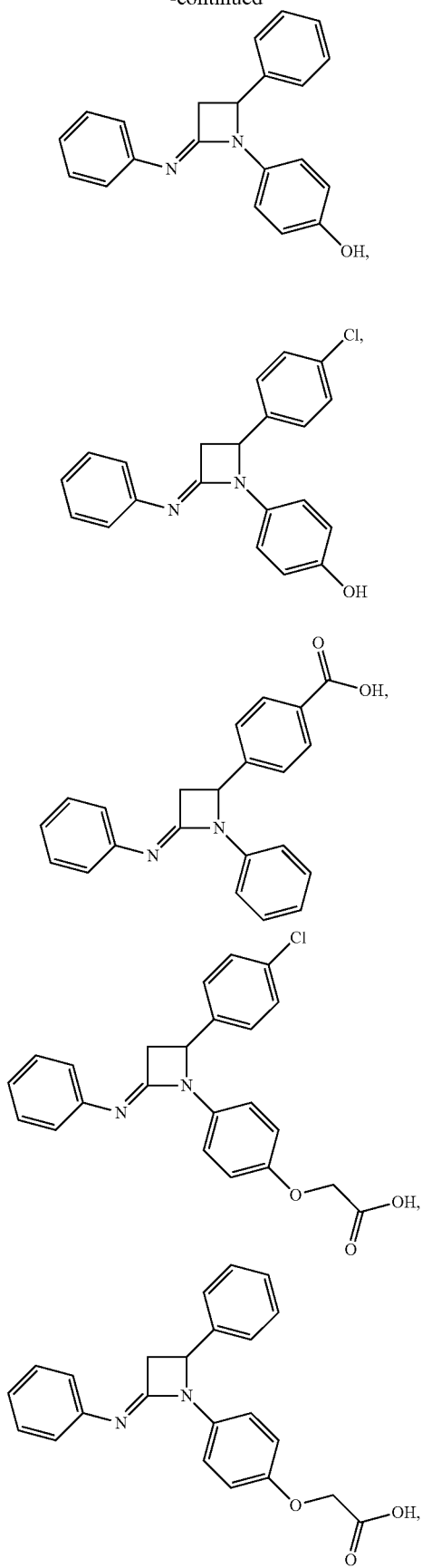
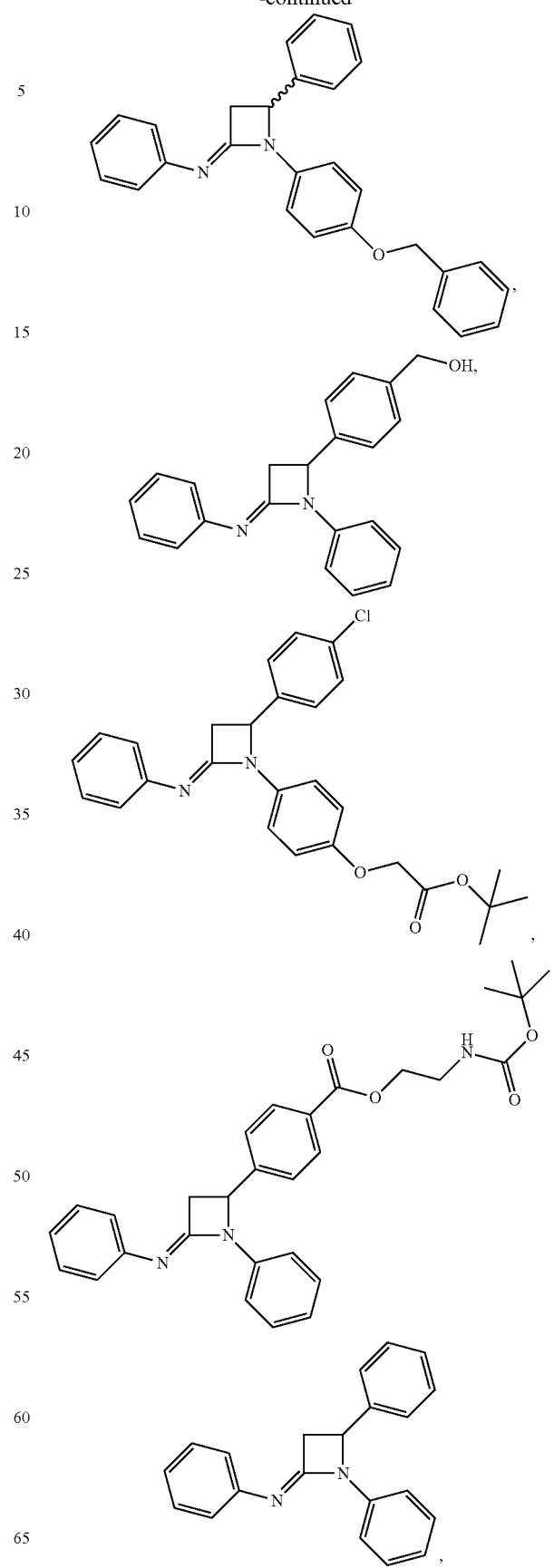

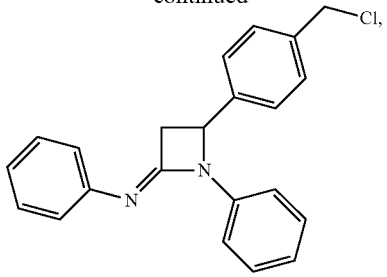
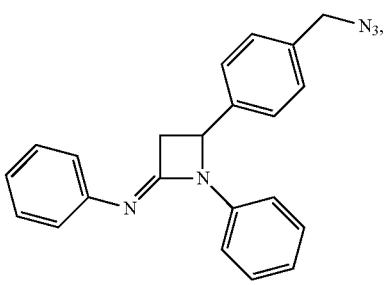
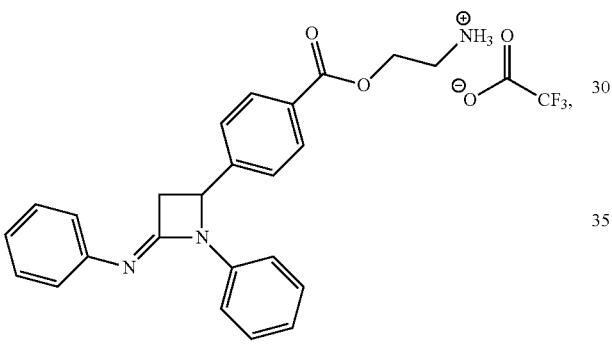
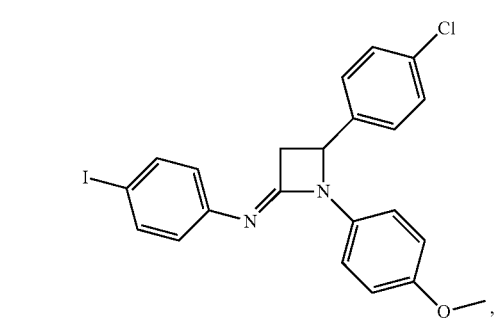
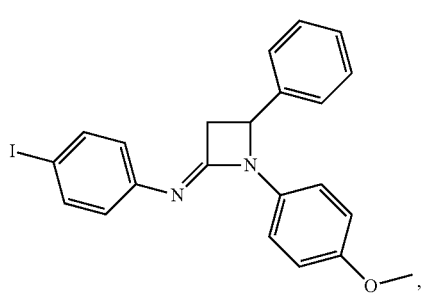
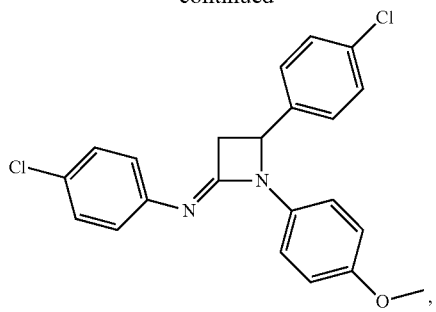
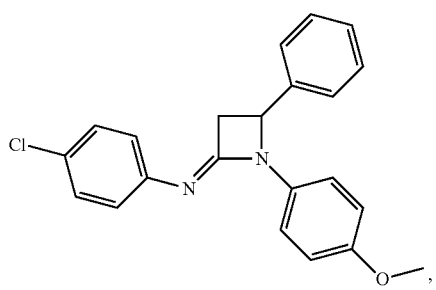
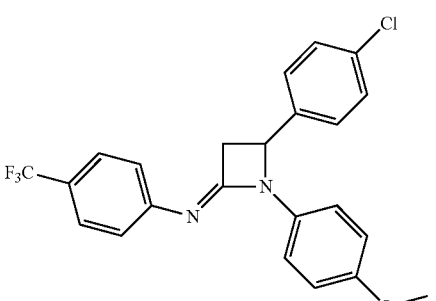
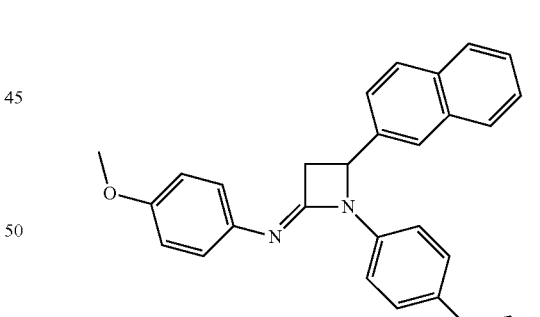
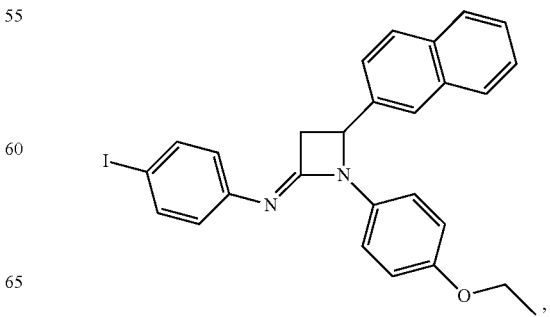

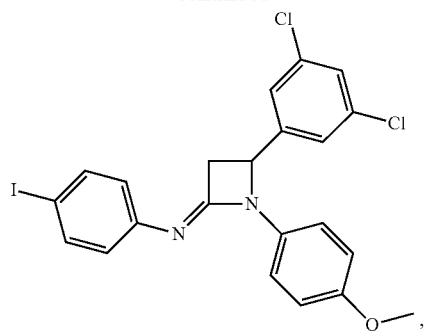
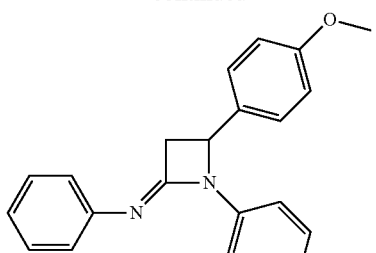
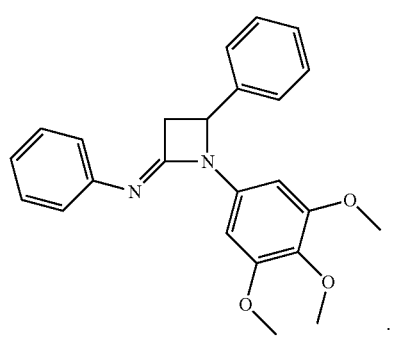
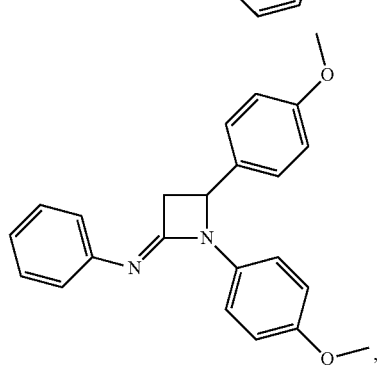
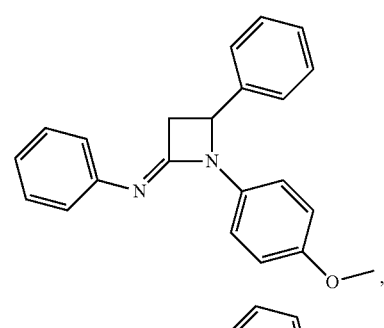
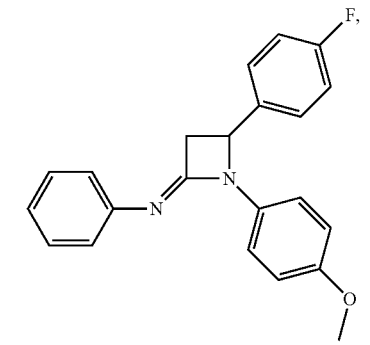
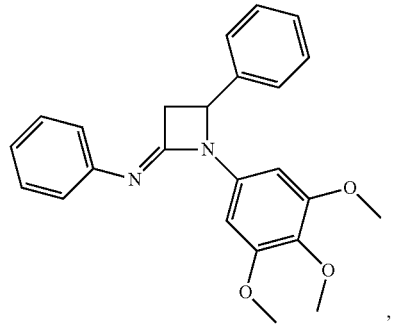
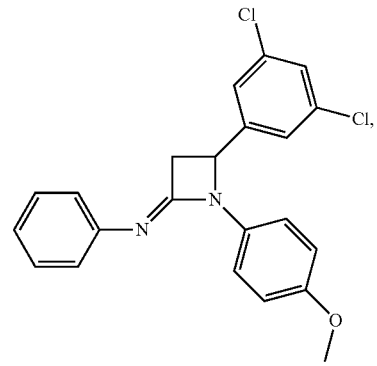
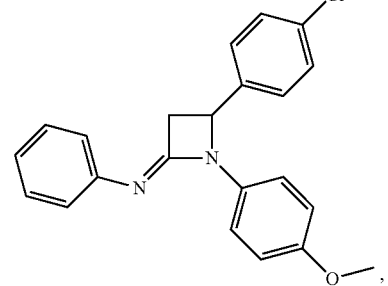
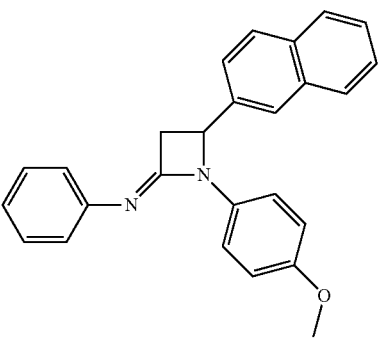

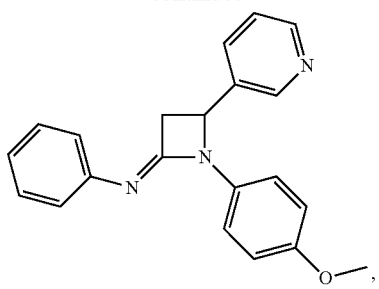
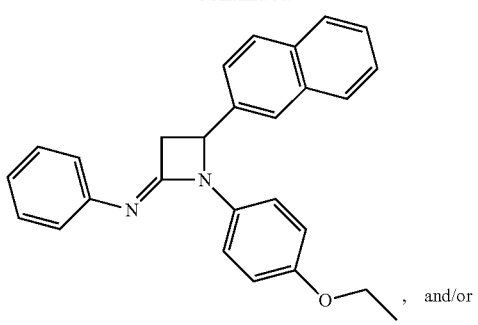, and/or
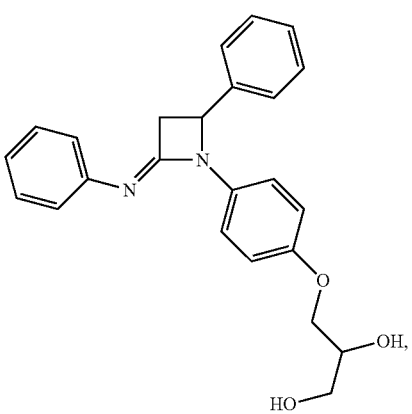
salts or solvates thereof.
In particular, especially for the method of preparation of the compound of formula (I) according to the present invention, the subject matter of the present invention concerns the molecules of the following structure:
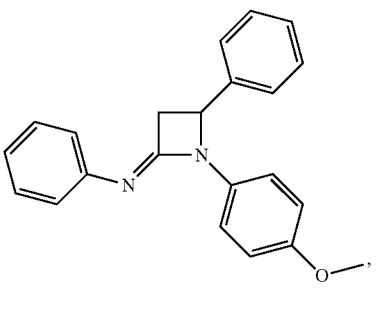
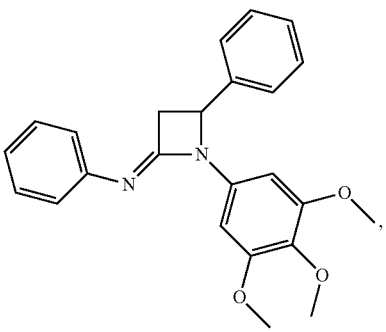

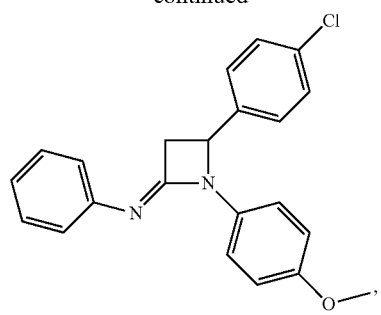
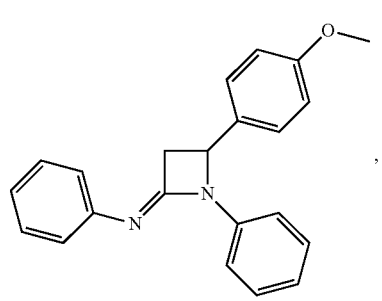
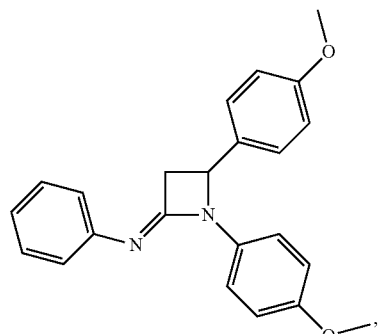
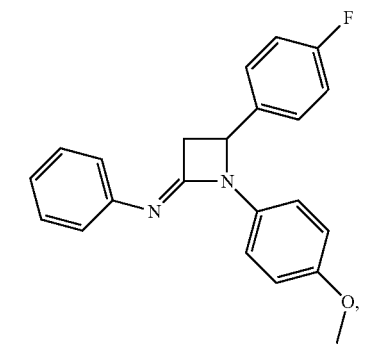
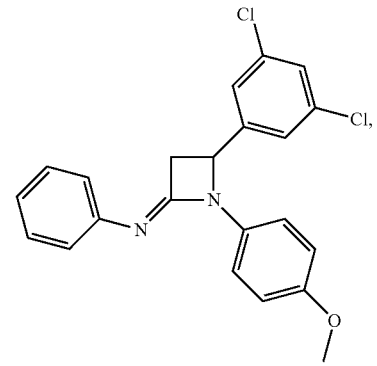
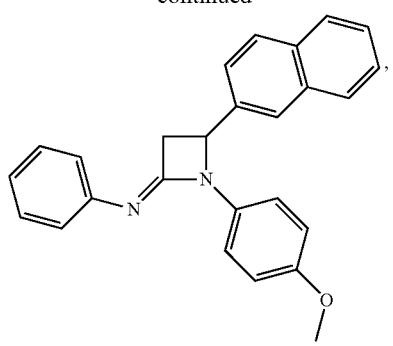
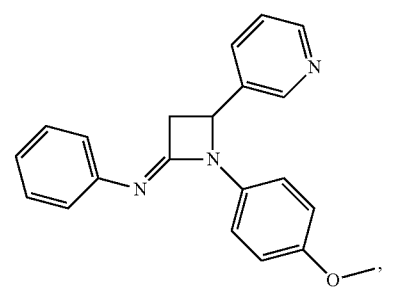
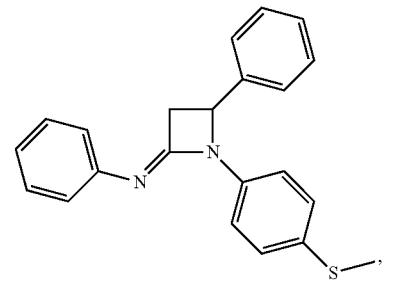
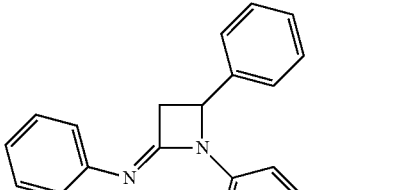
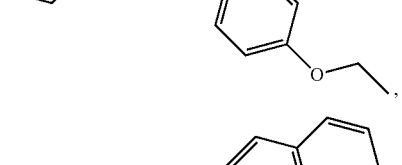
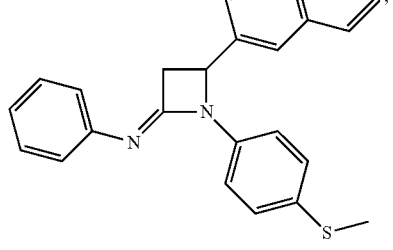

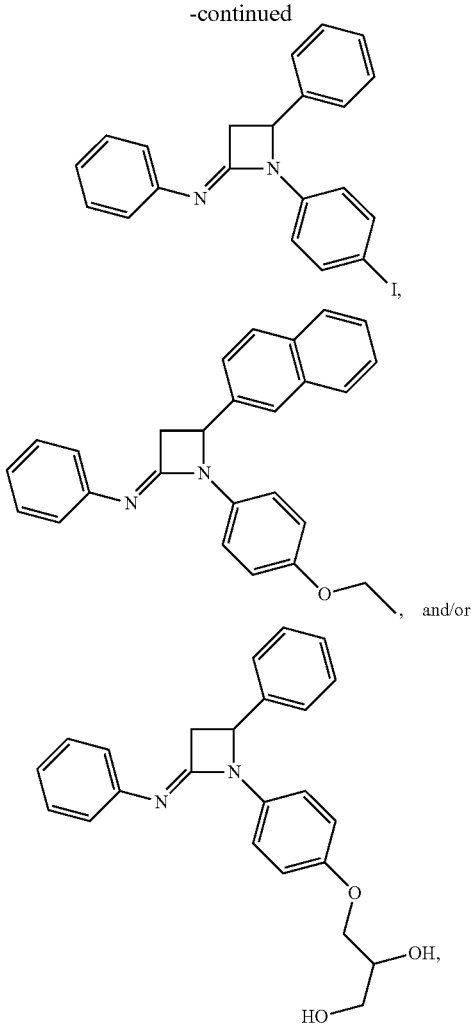

salts or solvates thereof.

The subject matter of the present invention thus also concerns a method to prepare a compound of formula (I) as defined above, including the explicitly excluded compounds above, implicating a compound of formula (II):

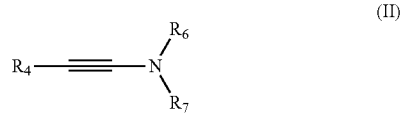

wherein $R_4$, $R_6$ and $R_7$ are as defined above.

Preferably, $R_4$ and $R_6$ have the same definitions in formula (II) as in the case of formula (I) with, if need be, protecting groups on the reacting functions thereof.

$R_7$ preferably is an electron-withdrawing group such as chosen in the group consisting of carbamates, a sulphonamide, amides and sulfonyles.

More preferably, $R_7$ is chosen in the group consisting of Boc (i.e. tert-butyloxycarbonyl), acetamide, mesylate or tosylate.

In a particular embodiment of the present invention, $R_6$—N—$R_7$ forms at least one ring, comprising e.g. lactames, oxazolidinone, or even sultames. More specifically, $R_6$—N—$R_7$ forms 2 or even 3 rings wherein at least one of the rings is a hydrocarbon ring, which can be saturated, unsaturated or aromatic.

The compound(s) of the present invention can be produced, and used in the form of mixtures of enantiomers and/or diasteroisomers.

The expression "mixtures of enantiomers" in the present invention means any mixture of enantiomers. The mixtures can be racemic, i.e. 50/50% of each enantiomer in weight (w/w), or non-racemic, i.e. enriched in one or the other of the enantiomer so that the ratios w/w are between 50/50% and 75/25%, between 75/25% and 90/10% or above 95% of one enantiomer in comparison with the other.

The expression "mixtures of diastereoisomers" in the present invention means any mixture of diastereoisomers in any proportions.

Moreover, the subject matter of the present invention concerns at least one compound of formula (I) for its use as an antibiotic or for its use in combination with an antibiotic characterized in that the antibiotic is effective on bacteria chosen from gram-negative bacteria such as Enterobacteriaceae, *Pseudomonas aeruginosa, Acinetobacter baumannii*, preferably drug resistant forms of gram-negative bacteria to one or several classes of antibiotics comprising β-lactams by production of a β-lactamase.

In a particular embodiment, the present invention concerns a composition of several compounds of formula (I), in particular for its use as a drug (antibiotic), in the form of a mixture of enantiomers and/or diasteroisomers of formula (I).

In another particular embodiment, the present invention concerns a composition of several compounds of formula (I), in particular for its use in combination with at least one known antibiotic as defined hereunder, in the form of a mixture of enantiomers and/or diasteroisomers of formula (I).

The subject matter of the present invention thus also concerns a compound of formula (I) (in its different variants) for its use as a potentiating agent, preferably of an antibiotic.

Indeed, the combination of at least one compound of formula (I) with at least one antibiotic advantageously provides a potentiating effect, i.e. by "potentiating effect/action" it is meant according to the present invention that at least one of the active compounds acts either as a "suicide molecule" as explained above enabling the other active ingredient to be active (i.e. antibiotic), and/or increases the activity of at least one of the other compounds present in term of biological (i.e. antibiotic) activity through e.g. a synergistic effect.

Therefore, said compounds of formula (I) according to the present invention can be used alone, or in combination with each other, or at least one other antibiotic already known. The derivatives thereof, if they have antibiotic activity, can also be used.

Examples of known antibiotics already used as medicaments specific in this field which can be used in combination with at least one compound of the present invention, and whose effect may be potentiated by the compound(s) of formula (I) of the present invention, can belong to at least one of the families consisting of the beta-lactam family (such as an amoxicillin and/or ampicillin), the cephalosporin family (such as cephazolin), the tetracycline family (such as chlortetracycline), the rifamycin family (such as rifampicin), the peptide family (such as a polymyxin), the aminoside family (such as streptomycin), the phenicol family (such as chloramphenicol), the macrolide family (such as erythromycin).

Preferably, the combination comprises at least one known beta-lactam antibiotic. Examples of beta lactams preferentially used according to the present invention comprise carbapenems such as imipenem, meropenem, ertapenem and the compound commonly known as "PZ-601".

In yet another embodiment, the known antibiotic(s) is/are selected from the group consisting of the amoxicillin, ampicillin, carbapenems, cephazolin the cephalosporins, the glycopeptides, the polymyxins, the gramicidins, tyrocidin, the aminosides, the macrolides, the lincosamides, the synergistins, the phenicols, the tetracyclines, fusidic acid, the oxazolidinones, the rifamycins, the quinolones, the fluoroquinolones, the sulfamides, trimethoprim, and the mixtures thereof.

More preferably, the known antibiotic is selected from the group consisting of the penicillins, oxacillin, cloxacillin, ampicillin, meropenem, ertapenem, PZ-601, amoxicillin, bacampicillin, metampicillin, pivampicillin, azlocillin, mezlocillin, piperacillin, ticarcillin, pivmecillinam, sulbactam, tazobactam, imipenem, cephalexin, cephydroxii, cephaclor, cephatrizine, cephalotin, cephapirin, cephazolin, cephoxitin, cephamandole, cephotetan, cephuroxime, cephotaxime, cephsulodin, cefepime, cephoperazone, cephotiam, cephtazidime, cephtriaxone, cephixime, cephpodoxime, cephepime, colistin, latamoxef, aztreonam, vancomycin, vancocin, teicoplanin, polymyxin B, colistin, bacitracin, tyrothricin, streptomycin, kanamycin, tobramycin, amikacin, sisomycin, dibekacin, netilmycin, spectinomycin, spiramycin, ceftazidime, erythromycin, josamycin, roxithromycin, clarithromycin, azithromycin, lincomycin, clindamycin, virginiamycin, pristinamycin, dalfopristine-quinupristine, chloramphenicol, thiamphenicol, tetracycline, doxycycline, minocycline, fusidic acid, linezolide, rifamycin, rifampicin, nalidixic acid, oxolinic acid, pipemidic acid, flumequin, pefloxacin, norfloxacin, ofloxacin, ciprofloxacin, enoxacin, sparfloxacin, levofloxacin, moxifloxacin, nitroxolin, tilboquinol, nitrofurantoin, nifuroxazide, metronidazole, ornidazole, sulfadiazine, sulfamethisol, trimethoprim, isoniazide and the derivatives and mixtures thereof. Said antibiotics, and more particularly amoxicillin, can optionally be used in association with yet at least one another antibiotic activity enhancer such as clavulanic acid.

The present invention thus also relates to a pharmaceutical composition comprising at least one compound of formula (I) as presently disclosed and to the (medical) use(s) of said composition, advantageously as an antibiotic. Preferably the pharmaceutical composition of the present invention comprises only two therapeutically active substances, at least one of which is a compound of formula (I) as presently disclosed.

In particular embodiment of the present invention, the pharmaceutical composition comprises at least two compounds of formula (I) as presently disclosed.

Moreover, the second therapeutically active substance comprised in the pharmaceutical composition of the invention can be an antibiotic which is already known as such and already used as medicament specific in this field and whose activity is potentiated.

Preferably, the pharmaceutical composition of the present invention comprises at least two therapeutically active substances, one of which exerts a potentiating action on the other(s).

Examples of known antibiotics already used as medicaments specific in this field (such as those cited above) can be used in the pharmaceutical composition of the invention, said known antibiotics' effect may be potentiated by the first therapeutically active substance (i.e. compound of formula (I) according to the present invention, including the excluded compound thereof), as explained above.

Of course, the pharmaceutical composition according to the invention is not restricted to the use of only those antibiotics mentioned above. In fact, considering the potentiating effect exerted by the compound defined in the invention of formula (I), other known or future antibiotics can also be successfully used.

These pharmaceutical compositions can be administered orally, rectally, parenterally, intramuscularly or locally by topical application on the skin and the mucosa. In all cases, the pharmaceutical form of the pharmaceutical composition of the invention shall be adapted to its use. For example, it can be used in the form of a solution, suspension, tablet . . . for oral administration. The compositions for parenteral administration are generally pharmaceutically acceptable sterile solutions or suspensions which can optionally be prepared immediately before use. The aqueous solutions may be suitable for intravenous administration in so far as the pH is properly adjusted and they are made isotonic, for example by adding a sufficient amount of sodium chloride or glucose.

The compositions according to the present invention can be solid or liquid and present in pharmaceutical forms in current use in human medicine or veterinary use such as, for example, simple or coated tablets, capsules, granules, suppositories, injectable preparations, ointments, creams, gels; they are prepared according to the usual methods.

The active principle or principles can be incorporated in the excipients usually used in these pharmaceutical compositions, such as cellulose derivatives (HPMC, HPC, microcrystalline cellulose, etc.), talc, gum Arabic, lactose, starch, magnesium stearate, cocoa butter, aqueous or other media, fatty bodies of animal or plant origin, paraffin derivatives, glycols, different wetting, dispersing or emulsifying agents, preservatives. These compositions can notably take the form of a lyophilisate designed to be dissolved as required in an appropriate solvent, for example pyrogen free sterile water.

The compound(s) and/or pharmaceutical composition(s) according to the invention can be formulated so as to be suitable for a simultaneous or sequential administration of said at least one compound of formula (I) according to the invention and known antibiotic agent(s) as defined above.

The pharmaceutical composition of the invention thus enables the treatment of local or systemic infections caused by resistant microorganisms using doses of the compound of formula (I) the present invention, or combinations thereof eventually with known antibiotic agent(s) as defined above.

In the case of such a combination, the active substance are preferably lower than the doses required for treating the same infections due to susceptible microorganisms with one or the other of these same said compound of formula (I) according to the invention and known antibiotic agent as defined above alone.

The result is to offer a treatment which has at least the following advantages:
  effectiveness at very low doses against nonresistant microorganisms,
  effectiveness against microorganisms resistant to at least one therapeutic agent,
  control of recurrence phenomena, and/or
  control of phenomena of resistant microorganisms selection.

Advantageously, there is a notable reduction in the risks of toxicity and/or adverse effects (well known to the person of the art for the known antibiotics), thanks to the potentiation which enables the administration of very low doses.

The pharmaceutical compositions of the invention are a simple and efficient means to combat the problems related to microbial agents in general which comprise mainly resistance to therapeutic agents and toxicity of the latter resulting from the use of high doses.

A method according to the present invention for treating patients having a bacterial infection consists in administering to said patients the dose, determined by the physician, of the pharmaceutical composition of the invention comprising suitable doses of at least one compound of formula (I) according to the invention, combined with suitable doses of at least one said known antibiotic agent(s) as defined above.

In a particular embodiment of the present invention, the compositions thus include at least two active principles, one of which at least is a compound of formula (I) as defined presently, which can be administered simultaneously, separately or spread over time. They can for example be provided in kit form, allowing the administration of a compound of general formula (I) and that of another antibacterial compound separately.

The present invention also proposes a kit characterized in that it comprises at least one first container containing a first therapeutically active compound of formula (I) (including all variants, such as the excluded compounds above) and mixtures thereof, and at least one second container containing a second therapeutically active substance which is an antibiotic, in particular as defined above. The kit of the invention preferably contains instructions for use. Said kit enables health care personnel to prepare on demand either a mixture of suitable doses of the desired first therapeutic substance(s) and of the desired antibiotic(s), for a simultaneous administration, or to sequentially and separately administer the suitable dose of at least one said first therapeutically active substance, followed by the suitable dose of at least one said second therapeutically active substance, that is, the suitable antibiotic, or vice versa. However, a mixture for simultaneous use shall be preferred for ease of administration.

Therefore the present invention in particular concerns a kit comprising:
  at least one first container containing a first therapeutically active compound of formula (I) as defined in any one of claims 1 to 6 or as defined in claim 7 and mixtures thereof, and
  at least one second container containing a second therapeutically active substance which is an antibiotic, as a combination product for simultaneous, sequential and separate use, in particular in antibiotherapy.

The dose administered of the compounds of formula (I) can vary depending on the severity and nature of the condition being treated, the particular subject, the administration route and the other antibacterial product involved. It can be, for example, between 0.1 mg and 1 g per kg per day, by oral route in humans or for veterinary purposes, or between 0.05 mg and 0.5 g per kg per day by intramuscular or intravenous route in humans or for veterinary purposes. The dose of the known antibacterial compound can also vary depending on the condition being treated, the particular subject, the administration route and the product involved, but generally follows the typical doses prescribed by practitioners, for example for human administration as described in the French reference Vidal. This dose can range up to 10 g per day per patient, or even more. Nevertheless, as a result of the potentiation provided by the compounds of general formula (I) to the known antibacterial compound(s), doses of the latter as part of the combination can be reduced compared to standard doses. The inventive combinations can also be used as disinfectants for surgical instruments.

Another subject matter of the present invention concerns the method to prepare a compound of formula (I) of the present invention which comprises in a first step (a) the addition of a compound of formula (II) as defined above with a compound of formula (III),

wherein fragments $R_1$, $R_2$, $R_3$ have the same definitions as in the case of formula (I) with, if need be, protecting groups on the reacting functions thereof.

In a preferred embodiment, at least one of the fragments of $R_2$ or $R_3$ in formula (III) is an electron-withdrawing group.

Preferably "electron-withdrawing group", in the context of the present invention, especially for the method of preparation of the compound of formula (I) according to the present invention, means that none of $R_2$ or $R_3$ in formula (III) is a mesomeric attracting fragment.

In another preferred embodiment, especially for the method of preparation of the compound of formula (I) according to the present invention, the fragment $R_1$ in formula (III) is an electro-donating group (equivalent to "electro-enriching group").

$R_1$ may be for example p-methoxyphenyl. The article "Tetrahedron Lett. 2006 47, 8109" shows how to cut off the p-methoxyphenyl moiety and thus liberate the secondary amine, which in turn can be substituted by another $R_1$. This can of course be applicable to other types of $R_1$.

In a more preferred embodiment, the fragment $R_1$ in formula (II) is an electro-donating group, and at least one of the fragments of $R_2$ or $R_3$ in formula (II) is an electron-withdrawing group, especially for the method of preparation of the compound of formula (I) according to the present invention. Therefore, in yet a more preferred embodiment, at least one of the fragments of $R_2$ or $R_3$ in formula (II) is an inductive attracting fragment such as a para-halogenophenyl, and the fragment $R_1$ in formula (II) is an electro-donating group, whilst none of $R_2$ or $R_3$ in formula (III) is a mesomeric attracting fragment, especially for the method of preparation of the compound of formula (I) according to the present invention.

Preferably compound of formula (II) is added to compound of formula (III) with an excess of compound of formula (II). The excess of compound (II) is preferably superior to 1.5 equivalents (i.e. in moles) of compound (III). More preferably, the excess of compound (II) is comprised between 2 equivalents and 10 equivalents of compound (III).

The addition of step (a) is completed in the presence of a base B1.

Preferably, B1 is a tert-butanolate salt, such as t-BuONa, t-BuOLi, t-BuOK or t-BuONa. Preferably B1 is t-BuOLi.

In yet another embodiment, step (a) comprises an excess of base B1 proportionally to compound (II) in relation to compound (III). The excesses of compound (II) and B1 are preferably superior to 1.5 equivalents (i.e. in moles) of compound (III) (i.e. 1.5 equivalents of compound (II) and 1.5 equivalent of B1 in respect to compound (III)). More preferably, the excesses of compound (II) and B1 are comprised between 2 equivalents and 10 equivalents of compound (III).

The addition of step (a) may also be conducted in the presence of a polar solvent, such as dimethylformamide ("DMF"), preferably with a content of water inferior to 5% molar, more preferably with a content of water inferior to 1% molar (i.e. "dry"), yet in a more preferable embodiment without substantially any water (i.e. "extra dry"). In the most preferred embodiment, step (a) comprises dry or extra dry DMF.

Furthermore the addition of step (a) may be conducted under microwaves, preferably for a period of time comprised between 1 minute and 24 hours, more preferably between 5 minutes and 5 hours, even more preferably between 10 minutes and 1 hour, such as around (±5 minutes) 20 minutes, 30 minutes, 40 minutes or 50 minutes.

In a preferred embodiment, step (a) also comprises silicagel, preferably between 0.5 and 5 equivalents in reference to the imine of formula (III). More preferably, step (a) comprises silicagel between 0.8 and 2 equivalents in referenced to the imine (III). In yet a more preferred embodiment, step (a) comprises around (±0.1 equivalent) 1 equivalent of silicagel.

Moreover, the reaction of step (a) can be made under pressure and/or at a temperature above 50° C.

Preferably the pressure is greater than 1.5 bar, more preferably greater than 2 bars, even more preferably greater than 3 bars.

The temperature of the reaction of step (a) is preferably greater than 60° C., more preferably greater than 75° C., even more preferably greater than 85° C. In a particular preferred embodiment of the present invention, the temperature of step (a) is fixed at around 100° C., i.e. 100° C.±5° C.

Moreover, the method of preparation of the compound of formula (I) as defined above can be characterized in that the reaction of step (a) is made without the presence of a metal compound, such as copper, whether it is in its metallic or one of its oxidized or reduced forms.

In a particular embodiment of the present invention, the method to prepare a compound of formula (I) of the present invention thus comprises in its first step (a), the addition of a compound of formula (II) with a compound of formula (III) as defined above, in the presence of a base B1 which can be a tert-butanolate salt or an equivalent base thereof, such as phenolates, methanolates or hydroxides, wherein said addition of the compounds is made in a polar solvent such as dry or extra dry DMF.

In a preferred embodiment of the present invention, the method to prepare a compound of formula (I) of the present invention comprises in its first step (a) the addition of a compound of formula (II) with a compound of formula (III) as defined above, in the presence of a base B1 which can be a tert-butanolate salt or an equivalent base thereof, said addition of the compounds is made in dry or extra dry DMF wherein the reaction of step (a) is made under pressure and/or at a temperature above 50° C., preferably greater than 75° C., such as 85° C.±5° C. or 100° C.±5° C.

In yet a preferred embodiment of the present invention, the method to prepare a compound of formula (I) of the present invention comprises in a first step (a) the addition of a compound of formula (II) with a compound of formula (III) as defined above, in the presence of a base B1 which is a tert-butanolate salt or an equivalent base thereof, said addition of the compounds is made in dry or extra dry DMF, and wherein the reaction of step (a) is made under microwaves and under pressure and/or at a temperature above 50° C., preferably greater than 75° C., such as 85° C.±5° C. or 100° C.±5° C.

In an even more preferred embodiment of the present invention, the method to prepare a compound of formula (I) of the present invention comprises in its first step (a) the addition of a compound of formula (II), wherein at least one of $R_2$ or $R_3$ is an electron-withdrawing group, with a compound of formula (III) as defined above, in the presence of a base B1 which is a tert-butanolate salt or an equivalent base thereof, said addition of the compounds is made in dry or extra dry DMF, and wherein the reaction of step (a) is made under microwaves and under pressure and/or at a temperature above 50° C., preferably greater than 75° C., such as 85° C.±5° C. or 100° C.±5° C.

In an even more preferred embodiment of the present invention, the method to prepare a compound of formula (I) of the present invention comprises in its first step (a) the addition of a compound of formula (II), wherein $R_1$ is an electro-donating group, with a compound of formula (III) as defined above, in the presence of a base B1 which is a tert-butanolate salt or an equivalent base thereof, said addition of the compounds is made in dry or extra dry DMF, and wherein the reaction of step (a) is made under microwaves and under pressure and/or at a temperature above 50° C., preferably greater than 75° C., such as 85° C.±5° C. or 100° C.±5° C.

In an even more preferred embodiment of the present invention, the method to prepare a compound of formula (I) of the present invention comprises in its first step (a) the addition of a compound of formula (II), wherein $R_1$ is an electro-donating group and at least one of $R_2$ or $R_3$ is an electron-withdrawing group, with a compound of formula (III) as defined above, in the presence of a base B1 which is a tert-butanolate salt or an equivalent base thereof, said addition of the compounds is made in dry or extra dry DMF, and wherein the reaction of step (a) is made under microwaves and under pressure and/or at a temperature above 50° C., preferably greater than 75° C., such as 85° C.±5° C. or 100° C.±5° C.

It is another subject matter of the present invention to propose several imines of formula (III). The obtaining of imines is well documented in the art. Two methods have been used to obtain these compounds. These two methods ("Condition A" and "Condition B") both use the substitution of the oxygen atom of a carbonyl by the nitrogen atom of an amine:

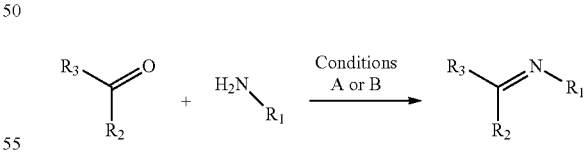

$R_1$, $R_2$, $R_3$ are as defined above, with adequate protecting groups if need-be.

The conditions A comprise silica (1 equivalent) in ethanol as solvent. Preferably ultra sounds are used at ambient temperature (20-25° C.). The time left for the reaction to proceed can for example be comprised between 1 min and 10 hours, preferably around one hour (±20 minutes).

The conditions B comprise toluene as solvent at reflux, for example using a Dean-Stark apparatus. Water appears as a sub product due to the condensation, and thus may be trapped by any convenient means, if need-be. The time left for the reaction to proceed can for example be comprised between 1 hour and 2 days, preferably around one day (±1 hour).

The method of preparation of the compound of formula (I) according to the present invention can furthermore comprise an optional step (b) of addition of $R_5$ as defined above in the case of formula (I), $R_5$ being conveniently protected if need-be, through a nucleophilic addition to the compound obtained in step (a).

Preferably the nucleophilic addition can be conducted with $R_5$—X, wherein X is a halogen atom in the presence of a base B2. Preferably B2 is a non-nucleophilic base, such as N,N-diisopropylethylamine ("DIPEA"), 1,8-diazabicycloundec-7-ene ("DBU"), triethylamine, 2,6-di-tert-butylpyridine, phosphazene bases such as t-Bu-$P_4$, lithium diisopropylamide ("LDA"), silicon based amides such as sodium or potassium bis(trimethylsilyl)amide ("NaHMDS" and "KHMDS"), 1-Lithio-2,2,6,6-tetramethylpiperidine ("LiTMP" also called "harpoon base"), sodium hydride, potassium hydride, or even sodium butoxide, potassium butoxide or lithium butoxide.

The method of preparation of the compound of formula (I) according to the present invention finally comprises a step (c) of retrieving the compound of formula (I) as defined presently.

By "retrieving" it is understood according to the present invention that the products obtained are extracted by techniques common in the art, e.g. by means of a two-phase washing comprising for example an organic solvent and water; alternatively, it is possible to recover the products in suspension (either in the form of crystals or amorphous solids) in the liquid that contains them, by filtration or drainage. Another way to recover the products may simply evaporate or freeze dry the solvent that contains them. This recovery phase may further contain a purification step by washing the obtained solid or to pass the compounds on a chromatography column.

EXAMPLES

The invention shall become clearer in the following examples describing different embodiments, which are given for purposes of illustration and not by way of limitation.

Example 1: Reaction Conditions Establishment

Different operating conditions involving imines, ynamides and at least a base were tested in order to prepare azetidinimine feature (Table 1).

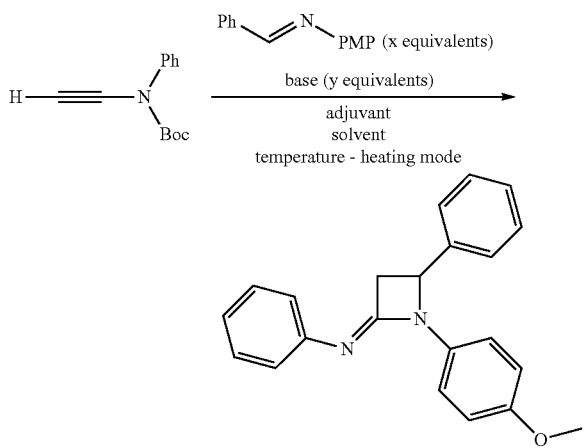

TABLE 1

| Entry # | Base | Solvent | T(° C.) | Heating | Time | Adjuvant | Observations |
|---|---|---|---|---|---|---|---|
| 1 | t-BuONa | DMF | AT | — | 24 h | — | imine + ynamide |
|  |  |  | AT | — | 1 h | DMAP | No evolution |
|  |  |  | 40 | □ | 16 h | — | No evolution |
|  |  |  | AT | — | 72 h | Indole cat. (5 mol %) | No evolution |
| 2 | t-BuONa | DMF | AT | — | 24 h | Indole cat. (5 mol %) | imine + ynamide |
| 3 | NaOH | DMF | AT | — | 24 h | — | imine + ynamide |
|  |  |  | 40 | □ | 24 h | — | imine + ynamide + unknown |
| 4 | MeONa (30% MeOH) | DMF | AT | — | 24 h | — | imine + ynamide |
|  |  |  | 40 | □ | 16 h | — | No evolution |
|  |  |  | 70 | □ | 16 h | — | No evolution |
| 5 | MeONa (solid) | DMF | AT | — | 24 h | — | imine + ynamide |
|  |  |  | 40 | □ | 16 h | — | No evolution |
|  |  |  | 70 | □ | 16 h | — | No evolution |
| 6 | NaOH (dried) | DMF | AT | — | 24 h | — | imine + ynamide + reduced imine |
|  |  |  | 40 | □ | 16 h | — | imine + ynamide, no evolution |
|  |  |  | 70 | □ | 16 h | — | imine + ynamide, no evolution |
| 7 | LiOH (dried) | DMF | AT | — | 24 h | — | imine + ynamide |
|  |  |  | 40 | □ | 16 h | — | No evolution |
|  |  |  | 70 | □ | 16 h | — | No evolution |
| 8 | KOH (dried) | DMF | AT | — | 24 h | — | imine + ynamide |
|  |  |  | 40 | □ | 16 h | — | No evolution |
|  |  |  | 70 | □ | 16 h | — | No evolution |
| 9 | $Cs_2CO_3$ | DMF | AT | — | 24 h | — | imine + ynamide |
|  |  |  | 40 | □ | 16 h | — | No evolution |
|  |  |  | 70 | □ | 16 h | — | No evolution |

TABLE 1-continued

Reaction conditions establishment

| Entry # | Base | Solvent | T(° C.) | Heating | Time | Adjuvant | Observations |
|---|---|---|---|---|---|---|---|
| 10 | NaOH (dried) | dry DMF | AT | — | 24 h | — | imine + ynamide + reduced imine |
|  |  |  | 60 | ☐ | 16 h | — | imine + ynamide, no evolution |
| 11 | t-BuONa | dry DMF | AT | — | 24 h | — | imine + ynamide + azetidinimide |
|  |  |  | 60 | ☐ | 16 h | — | No evolution 55% isolated |
| 12 | TBAF 1M THF | dry DMF | AT | — | 24 h | — | imine + ynamide + reduced imine |
|  | TBAF 1M THF | dry DMF | 60-80 | ☐ | 48 h | — | imine + ynamide, no evolution |
| 13 | t-BuONa | dry DMF | AT | — | 24 h | Yb(OTf)$_3$ | imine + ynamide + reduced imine |
|  |  |  | 60-80 | ☐ | 48 h | — | No evolution |
| 14 | TBAF 1M THF | dry DMF | AT | — | 24 h | Yb(OTf)$_3$ | imine + ynamide + reduced imine |
|  |  |  | 60-80 | ☐ | 48 h | — | No evolution |
| 15 | DBU | dry DMF | AT | — | 24 h | — | imine + ynamide + imine réduite |
|  |  |  | 60-80 | ☐ | 48h | — | No evolution |

Different conditions of reaction were produced using bases, solvents, adjuvants at different reaction temperatures and times. In the conditions set in this first study (i.e. particular chemical structures of imine and ynamide), the type of base "tert-butoxide" seemed required as well as the use of extra dry DMF (sold in a bottle with septum containing a sieve in the DMF) (entry 11). The method of preparing a compound of formula (I) according to the present invention thus is preferably conducted with a step (a) comprising less than 5% mol of water, relative to the solvent, more preferably less than 3% mol, or less than 1% mol of water, relative to the solvent. In the most preferred embodiment of the method of the invention, no water is present in step (a) of said method. The method of preparing a compound of formula (I) according to the present invention thus is preferably conducted with a step (a) comprising a base B1 which is a tert-butoxide.

Example 2: Optimization of the Reaction Conditions

After having verified the possibility to access the desired compound, the previously determined method was optimized by studying the best reaction conditions (Table 2)

TABLE 2 optimization of the method

| Entry # | Base | Solvent | T (° C.) | Heating | Time | Adjuvant | Observations |
|---|---|---|---|---|---|---|---|
| 11 | t-BuONa | dry DMF | AT | — | 24 h | — | imine + ynamide + azetidinimide |
| 1 | t-BuONa | dry DMF | 60 | ☐ | 16 h | — | No evolution |
| 2 | t-BuONa | dry DMF | 25 | MW | 10 min | — | imine + azetidinimide (ratio crude NMR 97/3: imine/azet.) |
|  |  |  | 80 | MW | 30 min | — | imine + azetidinimide (ratio crude NMR 90/10: imine/azet.) |
|  |  |  | 80 | MW | 1 h | — | imine + azetidinimide (ratio crude NMR 80/20: imine/azet.) |
| 3 | t-BuONa | THF (distilled) | 57 | MW | 1 h | — | imine + ynamide |
| 4 | t-BuOK | dry DMF | 80 | MW | 1 h | — | imine + azetidinimide (ratio crude NMR 48/52: imine/azet.) 46% isolated |
| 5 | t-BuOK | dry DMF | 80 | MW | 1 h | No molecular sieve* | imine + azetidinimide (ratio crude NMR 45/55: imine/azet.) |
| 6 | t-BuOLi | dry DMF | 80 | MW | 1 h | — | imine + azetidinimide (ratio crude NMR 50/50: imine/azet.) |
| 7 | t-BuOK | dry DMF | 80 | MW | 1 h | 2 eq. of ynamide | imine + azetidinimide (ratio crude NMR 37/63: imine/azet.) 45% isolated |
| 8 | t-BuOK | Toluene | 100 | MW | 1 h | — | imine - no more ynamide - no azetidinimine |

TABLE 2-continued optimization of the method

| Entry # | Base | Solvent | T (° C.) | Heating | Time | Adjuvant | Observations |
|---|---|---|---|---|---|---|---|
| 9 | t-BuOK | dry DMF | 80 | □ | 1 h | Slow addition of ynamide at 80° C. | MS - no reaction |
| | | | | | 16 h | | MS - no reaction - no evolution |
| 10 | t-BuOK | dry DMF | AT | □ | 1 h-4 d | — | MS - no reaction |
| 11 | t-BuOK | dry DMF | 80 | MW | 1 h | 2 eq. of base | No improvement |
| 12 | t-BuOLi | dry DMF | 80 | MW | 1 h | No molecular sieve - 2 eq. of base | No improvement |
| 13 | t-BuOLi | dry DMF | 80 | MW | 1 h | With molecular sieve - 2 eq. of base | No improvement - seems cleaner |
| 14 | t-BuOLi | dry DMF | 80 | MW | 1 h | With molecular sieve - 10 eq. of base | No improvement - seems more dirty |
| 15 | t-BuOLi | N-methylacetamide | 80 | MW | 1 h | — | MS - no reaction |
| 16 | t-BuOLi | ACN | 65 | MW | 1 h | — | MS - no reaction |
| 17 | t-BuOLi | dry DMF | 80 | □ | 1 h | Round bottom flask + refrigerant | MS - no reaction |
| | | | | | 16 h | | No improvement |
| | | | | | 48 h | | No improvement |
| 18 | t-BuOLi | dry DMF | 80 | □ | 1 h | sealed tube | Traces of azetidinimine |
| | | | | | 16 h | | No improvement |
| | | | | | 48 h | | No improvement |
| 19 | t-BuOLi | dry DMF | 80 | MW | 2 h | — | No improvement |
| | | | | | 1 h | 1 equiv. of ynamide added | No improvement |
| 20 | t-BuOLi | dry DMF | 80 | MW | 1 h | 10 mol % of t-BuOLi | MS - no reaction |
| 21 | t-BuOLi | dry DMF | 80 | MW | 1 h | More concentrated - 0.16M vs. 0.33M | Traces of azetidinimine |
| 22 | t-BuOLi | dry DMF | 80 | MW | 1 h | less concentrated - 0.66M vs. 0.33M | MS - no reaction |
| 23 | t-BuOLi | dry DMF | 80 | MW | 1 h | Smaller tube MW | No improvement |
| | | | 100 | | 1 h | — | conversion improved |
| 24 | t-BuOLi | dry DMF | 120 | MW | 1 h | smaller tube MW | Degradation product |
| | | | 150 | | 1 h | | No more degradation product |
| 25 | t-BuOLi | dry DMF | 100 | MW | 1 h | silicagel added 2.5 eq. | Clear improvement |
| 26 | t-BuOLi | dry DMF | 100 | MW | 1 h | silicagel added 2.5 eq. + 2 eq. of base | Formation of a secondary supplementary product |
| 27 | t-BuOLi | dry DMF | 100 | MW | 1 h | silicagel added 1.0 eq. | Same as entry 4-1.0 eq. seems to be enough |
| 28 | t-BuOLi | dry DMF | 100 | MW | 1 h | silicagel added 10.0 eq. | Formation of a secondary supplementary product |
| 29 | t-BuOLi | dry DMF | 100 | MW | 1 h | Alumina added 1.0 eq. | Same as entry 4 |

TABLE 2-continued optimization of the method

| Entry # | Base | Solvent | T (° C.) | Heating | Time | Adjuvant | Observations |
|---|---|---|---|---|---|---|---|
| 30 | t-BuOLi | dry DMF | 100 | MW | 1 h | Addition of 10 mol % | No improvement |
| 31 | t-BuOLi | dry DMF | 100 | MW | 1 h | 3 eq. of ynamide | Conversion of the imine clearly improved but the reaction is more dirty |
| 32 | t-BuOLi | dry DMF | 100 | MW | 1 h | 3 eq. of ynamide 3 times with 20 min interspace | No improvement, on the contrary |

*3A molecular sieve being present in other cases in order to avoid parasite reactions with water.
(wherein MW = microwave)

This study showed that the use of lithium tert-butoxide was particularly favorable to the reaction conditions previously set. The method of preparing a compound of formula (I) according to the present invention thus is preferably conducted with a step (a) comprising a base B1 which is lithium tert-butoxide. Furthermore, the reaction time could be reduced to 1 hour by use of microwaves to an optimized temperature of 100° C. The method of preparing a compound of formula (I) according to the present invention thus is preferably conducted with a step (a) comprising microwaves for a period of time stretching up e.g. up to 24 hours, preferably around 1 hour (±15 minutes), at a temperature above 80° C., preferably around 100° C. (±10° C.). It was therefore determined that the use of e.g. microwaves makes it possible to obtain in a significant quantity the desired product.

Other parameters were also studied. The most relevant parameter was the addition of silicagel which proved to be particularly favorable to the reaction. Indeed, the use of 1 equivalent of Silicagel was sufficient to significantly increase the conversion of the starting imine. The method of preparing a compound of formula (I) according to the present invention thus is preferably conducted with a step (a) comprising silicagel, preferably in a quantity of around 1 equivalent (±0.1 eq) in respect of the product at the lowest quantity engaged in the reaction, e.g. the imine. Finally it was also found that the conversion of the imine could be improved with the use of an excess of ynamide (2 equiv.) accompanied by a proportional base B1 excess (2 equiv.). The method of preparing a compound of formula (I) according to the present invention thus is preferably conducted with a step (a) comprising an excess of ynamide, e.g. around 2 eq. (±0.1 eq.) in respect of the imine. The method of preparing a compound of formula (I) according to the present invention thus is preferably conducted with a step (a) comprising an excess of base B1, e.g. around 2 eq. (±0.1 eq.) in respect of the imine. More preferably, the method of preparing a compound of formula (I) according to the present invention thus is conducted with a step (a) comprising an excess of ynamide, e.g. around 2 eq. (±0.1 eq.) in respect of the imine, accompanied by a proportional base B1 excess, e.g. around 2 eq. (±0.1 eq.) in respect of the imine.

Multiple optimization tests were summarized in Table 2. The conditions adopted for the rest of the study were as follows: ynamide (2 eq.); imine (1 eq.); t-BuOLi (2 eq.); Silicagel (1 eq.); extra dry DMF; 100° C., 1 h, micro-waves. The method of preparing a compound of formula (I) according to the present invention thus is preferably conducted with a step (a) comprising around 2 equivalents of ynamide, around 1 equivalent of imine, around 2 equivalents of t-BuOLi, around 1 equivalent of silicagel in extra dry DMF at around 100° C., for 1 h, under micro-waves.

Example 3: Variation of the Imine

An aromatic imine family was first prepared using mainly two methods (Table 3).

Method 1:

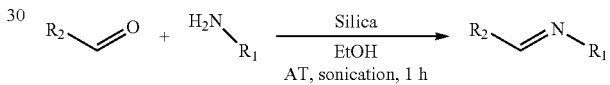

Method 2:

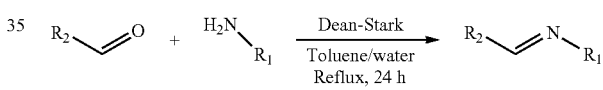

TABLE 3 imine syntheses

| Entry | $R_2$ | $R_1$ | method | R(%) |
|---|---|---|---|---|
| 1 | $C_6H_5$ | 4-(OMe)$C_6H_4$ | 1 | 86 |
| 2 | 4-(OMe)$C_6H_4$ | $C_6H_5$ | 1 | 82 |
| 3 | 4-(NO$_2$)$C_6H_4$ | 4-(OMe)$C_6H_4$ | 1 | 86 |
| 4 | 4-(OMe)$C_6H_4$ | 4-(OMe)$C_6H_4$ | 1 | 88 |
| 5 | 4-(F)$C_6H_4$ | 4-(OMe)$C_6H_4$ | 1 | 94 |
| 6 | 4-(CN)$C_6H_4$ | 4-(OMe)$C_6H_4$ | 1 | 67 |
| 7 | $C_6H_5$ | 3,4,5-(OMe)$_3C_6H_2$ | 1 | 72 |
| 8 | $C_6H_5$ | 4-(NO$_2$)$C_6H_4$ | 2 | 57 |
| 9 | 4-(Cl)$C_6H_4$ | 4-(OMe)$C_6H_4$ | 1 | 80 |
| 10 | 2-(F)$C_6H_4$ | 4-(OMe)$C_6H_4$ | 1 | 10 |
| 11 | 2,4-(Cl)$_2C_6H_3$ | 4-(OMe)$C_6H_4$ | 1 | 89 |
| 12 | 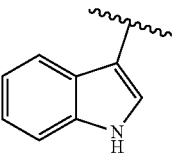 [SMILES: *c1c[nH]c2ccccc12] | 4-(OMe)$C_6H_4$ | 1 | 0 |
| 13 | 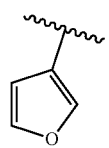 [SMILES: *c1ccoc1] | 4-(OMe)$C_6H_4$ | 1 | 0 |

TABLE 3-continued imine syntheses

| Entry | R₂ | R₁ | method | R(%) |
|---|---|---|---|---|
| 14 | 2-pyridyl | 4-(OMe)C₆H₄ | 1 | 0 |
| 15 | 3-pyridyl | 4-(OMe)C₆H₄ | 1 | 12 |
| 16 | 3-thienyl | 4-(OMe)C₆H₄ | 1 | 0 |
| 17 | 4-(CHO)C₆H₄ | 4-(OMe)C₆H₄<br>2 equivalents | 1 | 98 |

These imines were then engaged in the conditions to produce azetidinimine starting from ynamide as previously established (Table 4).

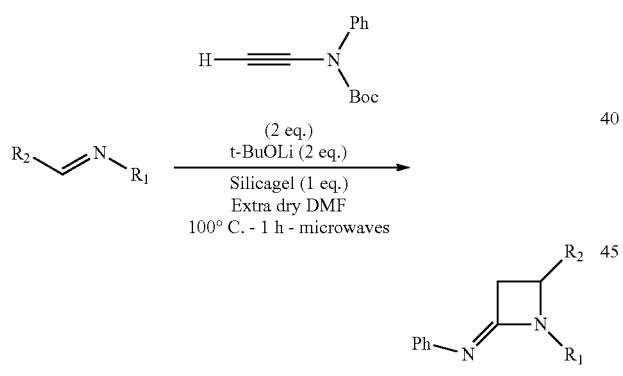

TABLE 4

Preparation of azetidinimines by imine variation

| Entry # | R₂ | R₁ | R(%) |
|---|---|---|---|
| 1 | C₆H₅ | 4-(OMe)C₆H₄ | 55 |
| 2 | 4-(OMe)C₆H₄ | C₆H₅ | 46 |
| 3 | 4-(NO₂)C₆H₄ | 4-(OMe)C₆H₄ | 0 |
| 4 | 4-(OMe)C₆H₄ | 4-(OMe)C₆H₄ | 40 |
| 5 | 4-(F)C₆H₄ | 4-(OMe)C₆H₄ | 83 |
| 6 | 4-(CN)C₆H₄ | 4-(OMe)C₆H₄ | 0 |
| 7 | C₆H₅ | 3,4,5-(OMe)₃C₆H₂ | 54 |
| 8 | C₆H₅ | 4-(NO₂)C₆H₄ | 0 |
| 9 | 4-(Cl)C₆H₄ | 4-(OMe)C₆H₄ | 86 |
| 10 | 2-(F)C₆H₄ | 4-(OMe)C₆H₄ | 0 |
| 11 | 2,4-(Cl)₂C₆H₃ | 4-(OMe)C₆H₄ | 53 |

TABLE 4-continued

Preparation of azetidinimines by imine variation

| Entry # | R₂ | R₁ | R(%) |
|---|---|---|---|
| 12 | 3-indolyl | 4-(OMe)C₆H₄ | — |
| 13 | 3-furyl | 4-(OMe)C₆H₄ | — |
| 14 | 2-pyridyl | 4-(OMe)C₆H₄ | — |
| 15 | 3-pyridyl | 4-(OMe)C₆H₄ | 24 |
| 16 | 3-thienyl | 4-(OMe)C₆H₄ | — |
| 17 | 1,4-phenylene | 4-(OMe)C₆H₄ | — |

The application of the method was verified, i.e. the desired compounds were generally obtained in good yields. As previously mentioned, the study showed that the reaction was promoted when the imine was substituted by an electro donating group $R_1$ and/or an electron-withdrawing group in position R2 (and/or R3 according to formula (I) of the present invention).

Moreover, the p-methoxyphenyl group is a particular good choice for $R_1$, because of its electron donor character and various procedures described in literature (see e.g. Tetrahedron Lett. 2006 47, 8109) show how to cut off the p-methoxyphenyl moiety and thus liberate the secondary amine.

Moreover, the use of para-halophenyl as $R_2$ fragment proved particularly effective with excellent yields of up to 86%. The attractor inductive character of these derivatives could be the cause of such success. However, when electron-withdrawing mesomeric derivatives were used as $R_2$ fragments, it was rarely possible to observe the desired product in significant quantities.

Example 4: Biological Tests

These tests were conducted by comparing UV absorbance slope measurements of impenem alone, and then imipenem with the concerned azetidinimines at given concentrations in the presence of the enzyme. It was thus possible to monitor the hydrolysis of imipenem. Lower the value of the slope, the higher is the percentage of inhibition of the enzyme.

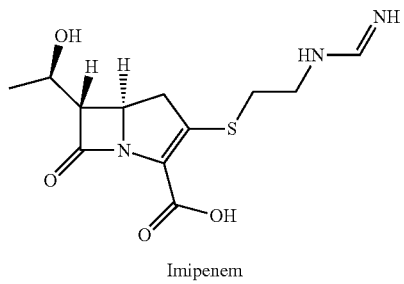 [SMILES: C[C@@H](O)[C@H]1C(=O)N2C(C(=O)O)=C(SCCNC=N)C[C@H]12]

Imipenem

Stability tests of imipenem with increasing concentrations of tested molecules of the present invention (T4#1, i.e. compound #1 of table 4; T4#7 i.e. compound #7 of table 4; T4#9 i.e. compound #9 of table 4; T4#2 i.e. compound #2 of table 4) were also conducted (Table 2).

TABLE 5

| | | Stability tests | | | |
|---|---|---|---|---|---|
| Entry | C (μM) | Slope T4#1 | Slope T4#7 | Slope T4#9 | Slope T4#2 |
| 1 | 100 | 506 | 174 | 390 | 321 |
| 2 | 10 | 50 | 10 | 38 | 30 |
| 3 | 1 | 9 | 0 | 2 | 3 |

Moreover, the different biology test results made on the compounds of the present invention are summarized in the table 6.

TABLE 6

Biology tests results summary

| Structures | NDM-1 Enzyme | | | OXA-48 Enzyme | | | KPC Enzyme | | |
|---|---|---|---|---|---|---|---|---|---|
| | C (μM) | Inhibition % | IC$_{50}$ (μM) | C (μM) | Inhibition % | IC$_{50}$ (μM) | C (μM) | Inhibition % | IC$_{50}$ (μM) |
| $C_{22}H_{20}N_2O$ MW: 318.1576 | 10 | 90 | 2-5 | No reported effect | | | ND | ND | ≈7 |
| Enantiomer 1 $C_{22}H_{20}N_2O$ MW: 318.1576 | 10 | 97 | <5 | ND | ND | ND | 10 | 70 | <10 |
| Enantiomer 2 $C_{22}H_{20}N_2O$ MW: 318.1576 | 10 | 95 | <5 | ND | ND | ND | 10 | 45 | >10 |
| $C_{24}H_{24}N_2O_3$ MW: 388.1787 | 50 | 78 | >50 | No reported effect | | | ND | ND | >50 |

TABLE 6-continued

Biology tests results summary

| Structures | NDM-1 Enzyme | | | OXA-48 Enzyme | | | KPC Enzyme | | |
|---|---|---|---|---|---|---|---|---|---|
| | C (μM) | Inhibition % | IC$_{50}$ (μM) | C (μM) | Inhibition % | IC$_{50}$ (μM) | C (μM) | Inhibition % | IC$_{50}$ (μM) |
| C$_{22}$H$_{19}$ClN$_2$O MW: 362.1186 | 10 | 96 | 2-5 | 50 | 21 | Solubility problems | 50 | 44 | ≈20 |
| C$_{22}$H$_{20}$N$_2$O MW: 318.1576 | 20 | 58 | >10 | No reported effect | | | No reported effect | | |
| C$_{23}$H$_{22}$N$_2$O$_2$ MW: 358.1681 | 10 | 67 | 5-10 | 10 | 3 | ND | 10 | 7 | ND |

TABLE 6-continued

| | Biology tests results summary | | | | | | | | |
|---|---|---|---|---|---|---|---|---|---|
| | NDM-1 Enzyme | | | OXA-48 Enzyme | | | KPC Enzyme | | |
| Structures | C (μM) | Inhibition % | IC$_{50}$ (μM) | C (μM) | Inhibition % | IC$_{50}$ (μM) | C (μM) | Inhibition % | IC$_{50}$ (μM) |
| C$_{22}$H$_{19}$FN$_2$O MW: 346.1481 | 10 | 9 | ND | No reported effect | | | 10 | 10 | ND |
| C$_{22}$H$_{18}$Cl$_2$N$_2$O MW: 397.2971 | 5 | 97 | 2.5-5 | 5 | 15 | ND | 5 | 84 | 2.5-5 |
| C$_{26}$H$_{22}$N$_2$O MW: 378.4657 | 5 | 94 | 2.5-5 | 20 | 94 | 10-20 | 10 | 99 | 5-7 |

TABLE 6-continued

Biology tests results summary

| Structures | NDM-1 Enzyme | | | OXA-48 Enzyme | | | KPC Enzyme | | |
|---|---|---|---|---|---|---|---|---|---|
| | C (μM) | Inhibition % | IC$_{50}$ (μM) | C (μM) | Inhibition % | IC$_{50}$ (μM) | C (μM) | Inhibition % | IC$_{50}$ (μM) |
| [Structure: C$_{21}$H$_{19}$N$_3$O, MW: 329.3951] | 100 | 23 | >100 | No reported effect | | | 100 | 12 | >100 |
| [Structure: C$_{22}$H$_{20}$N$_2$O, MW: 344.4726] | 5 | 98 | <1 | 10 | 15 | ND | 20 | 82 | <10 |
| [Structure: C$_{23}$H$_{22}$N$_2$O, MW: 342.4336] | 5 | 100 | 0.5-5 | 10 | 45 | >10 | 5 | 100 | <5 |
| [Structure: M.W.: 488.7535] | N.D. | N.D. | 0.7 | N.D. | N.D. | 7.5 | N.D. | N.D. | 2.7 |

TABLE 6-continued

Biology tests results summary

| Structures | NDM-1 Enzyme | | | OXA-48 Enzyme | | | KPC Enzyme | | |
|---|---|---|---|---|---|---|---|---|---|
| | C (μM) | Inhibition % | IC$_{50}$ (μM) | C (μM) | Inhibition % | IC$_{50}$ (μM) | C (μM) | Inhibition % | IC$_{50}$ (μM) |
| M.W.: 454.3115 | N.D. | N.D. | 1.1 | N.D. | N.D. | 9.2 | N.D. | N.D. | 3.3 |
| M.W.: 397.2990 | N.D. | N.D. | 0.5 | N.D. | N.D. | >50 | N.D. | N.D. | 2.9 |
| M.W.: 362.8570 | 10 | 100 | N.D. | N.D. | N.D. | >50 | N.D. | N.D. | 2 |
| M.W.: 430.8552 | 10 | 100 | N.D. | N.D. | N.D. | >50 | N.D. | N.D. | 3.6 |

TABLE 6-continued
Biology tests results summary
| Structures | NDM-1 Enzyme | | | OXA-48 Enzyme | | | KPC Enzyme | | |
|---|---|---|---|---|---|---|---|---|---|
| | C (µM) | Inhibition % | IC₅₀ (µM) | C (µM) | Inhibition % | IC₅₀ (µM) | C (µM) | Inhibition % | IC₅₀ (µM) |
| 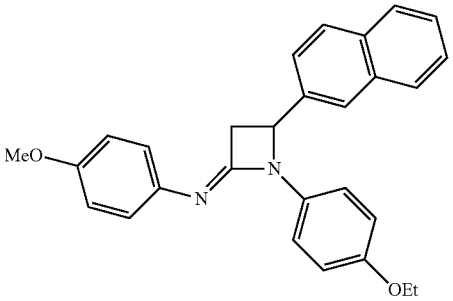 M.W.: 422.5280 | N.D. | N.D. | 0.6 | N.D. | N.D. | 7.4 | N.D. | N.D. | 2.4 |
| 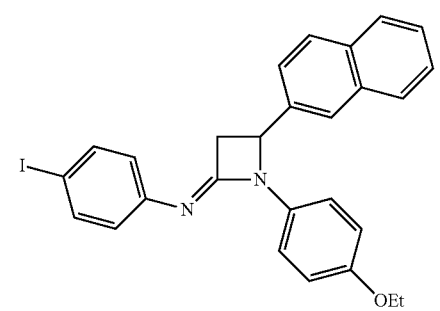 M.W.: 518.3985 | N.D. | N.D. | 0.5 | N.D. | N.D. | 6.2 | N.D. | N.D. | 2.5 |
| 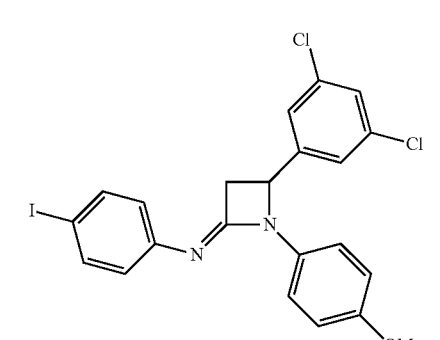 | N.D. | N.D. | 0.5 | N.D. | N.D. | 8.5 | N.D. | N.D. | 2.9 |
| 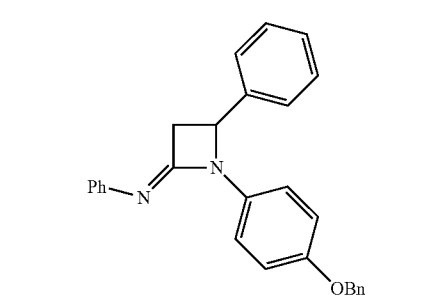 [SMILES: c1ccc(COc2ccc(N3/C(=N/c4ccccc4)CC3c3ccccc3)cc2)cc1] | N.D. | N.D. | 0.4 | 10 | 31 | N.D. | 10 | 86 | N.D. |

TABLE 6-continued
Biology tests results summary
| Structures | NDM-1 Enzyme | | | OXA-48 Enzyme | | | KPC Enzyme | | |
|---|---|---|---|---|---|---|---|---|---|
| | C (µM) | Inhibition % | IC$_{50}$ (µM) | C (µM) | Inhibition % | IC$_{50}$ (µM) | C (µM) | Inhibition % | IC$_{50}$ (µM) |
| 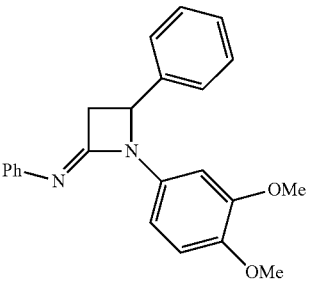 [SMILES: COc1ccc(N2/C(=N/c3ccccc3)CC2c2ccccc2)cc1OC] | N.D. | N.D. | 5-10 | 10 | 9 | N.D. | 10 | 17 | N.D. |
| 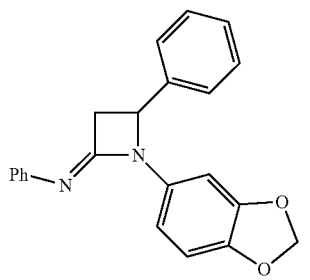 [SMILES: c1ccc(/N=C2\CC(c3ccccc3)N2c2ccc3c(c2)OCO3)cc1] | N.D. | N.D. | 5 | 10 | 20 | N.D. | 10 | 6 | N.D |
| 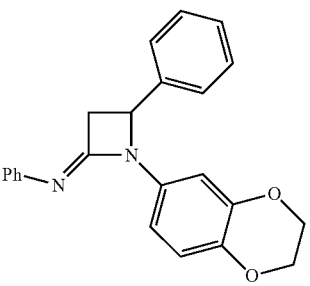 [SMILES: c1ccc(/N=C2\CC(c3ccccc3)N2c2ccc3c(c2)OCCO3)cc1] | N.D. | N.D. | 1.3 | N.D. | N.D. | >50 | N.D. | N.D. | 5-10 |
| 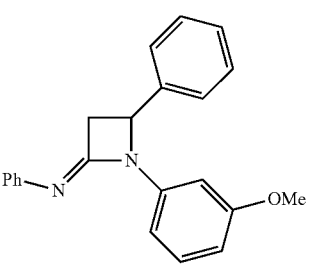 [SMILES: COc1cccc(N2/C(=N/c3ccccc3)CC2c2ccccc2)c1] | N.D. | N.D. | 1.3 | N.D | N.D. | >50 | N.D. | N.D. | 5-10 |
| 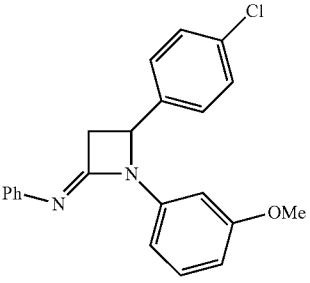 [SMILES: COc1cccc(N2/C(=N/c3ccccc3)CC2c2ccc(Cl)cc2)c1] | N.D. | N.D. | 0.4 | N.D. | N.D. | >50 | N.D. | N.D. | 2.5-5 |

TABLE 6-continued

Biology tests results summary

| Structures | NDM-1 Enzyme | | | OXA-48 Enzyme | | | KPC Enzyme | | |
|---|---|---|---|---|---|---|---|---|---|
| | C (μM) | Inhibition % | IC$_{50}$ (μM) | C (μM) | Inhibition % | IC$_{50}$ (μM) | C (μM) | Inhibition % | IC$_{50}$ (μM) |
| *[structure: 2-(4-chlorophenyl)-1-(2-methoxyphenyl)-azetidin-3-one N-phenylimine]* | N.D. | N.D. | 1.1 | N.D. | N.D. | >50 | N.D. | N.D. | 5-10 |
| *[structure: methyl 4-(1-phenyl-azetidinyl)benzoate N-phenylimine]* | N.D. | N.D. | 4.8 | 10 | 3.5 | N.D. | 10 | 6 | N.D. |
| *[structure: 2,N-diphenyl-azetidin-3-one N-phenylimine]* | N.D. | N.D. | 1.2 | No measurable effect at 10 μM | | | N.D. | N.D. | 6 |
| *[structure: tert-butyl 4-(1-phenyl-azetidinyl)benzoate N-phenylimine]* | N.D. | N.D. | 1.8 | 10 | 32 | N.D. | 10 | 45 | N.D. |

TABLE 6-continued

Biology tests results summary

| Structures | NDM-1 Enzyme | | | OXA-48 Enzyme | | | KPC Enzyme | | |
|---|---|---|---|---|---|---|---|---|---|
| | C (μM) | Inhibition % | IC$_{50}$ (μM) | C (μM) | Inhibition % | IC$_{50}$ (μM) | C (μM) | Inhibition % | IC$_{50}$ (μM) |
| (structure: 4-Cl-phenyl azetidine with Ph-N= and phenyl-O-CH$_2$-C(=O)-O-tBu) | N.D. | N.D. | 2.6 | N.D | N.D | >50 | N.D. | N.D. | 1.3 |
| (structure: 4-carboxyphenyl azetidine with Ph-N= and N-phenyl) | N.D. | N.D. | 0.7 | N.D. | N.D. | >50 | N.D. | N.D. | >50 |
| (structure: 4-Cl-phenyl azetidine with Ph-N= and phenyl-O-CH$_2$-COOH) | N.D. | N.D. | 0.6 | N.D. | N.D | >50 | N.D. | N.D. | >50 |
| (structure: phenyl azetidine with Ph-N= and 4-hydroxyphenyl) | N.D. | N.D. | 0.8 | N.D. | N.D. | >10 | N.D. | N.D. | >50 |

TABLE 6-continued

Biology tests results summary

| Structures | NDM-1 Enzyme | | | OXA-48 Enzyme | | | KPC Enzyme | | |
|---|---|---|---|---|---|---|---|---|---|
| | C (μM) | Inhibition % | IC$_{50}$ (μM) | C (μM) | Inhibition % | IC$_{50}$ (μM) | C (μM) | Inhibition % | IC$_{50}$ (μM) |
| (4-Cl-phenyl, 4-OH-phenyl azetidinone structure) | N.D. | N.D. | 3.6 | N.D. | N.D. | >10 | N.D. | N.D. | 5-7 |
| (benzoate NHBoc ester azetidinone structure) | N.D. | N.D. | 2.9 | N.D. | N.D. | >50 | N.D. | N.D. | 10 |
| (4-CH$_2$Cl-phenyl azetidinone structure) | N.D. | N.D. | 2.5 | No measurable effect at 10 μM | | | N.D. | N.D. | 6 |
| (4-CH$_2$N$_3$-phenyl azetidinone structure) | 10 | 100 | N.D. | N.D. | N.D. | >50 | 10 | 89 | N.D. |

Example 5: Experimental Section

1. General Remarks

Melting points were measured in capillary tubes on a Büchi B-540 apparatus and are uncorrected. Infrared spectra were recorded on a Perkin Elmer Spectrum BX FT-IR spectrometer. Proton (1H) and carbon (13C) NMR spectra were recorded on Bruker spectrometers: Avance 300 MHz (QNP—13C, 31P, 19F—probe or Dual 13C probe) and Avance 500 MHz (BB0—ATM probe or BBI—ATM probe). Carbon NMR (13C) spectra were recorded at 125 or 75 MHz, using a broadband decoupled mode with the multiplicities obtained using a JMOD or DEPT sequence. NMR experiments were carried out in deuterochloroform (CDCl3), chemical shifts (δ) are reported in parts per million (ppm) with reference to CDCl3 (1H: 7.26; 13C: 77.00). The following abbreviations are used for the proton spectra multiplicities: s: singlet, bs: broad singlet, d: doublet, t: triplet, q: quartet, m: multiplet, br: broad. Coupling constants (J) are reported in Hertz (Hz). Mass spectra were obtained either with a LCT (Micromass) instrument using electrospray ionization (ES), or from a Time of Flight analyzer (ESI-MS) for the high resolution mass spectra (HRMS). Elemental analyses were performed on a Perkin Elmer CHN 2400 analyzer with detection by catharometry. Thin-layer chromatography was performed on silica gel 60 F254 on aluminium plates (Merck) and visualized under a UVP Mineralight UVLS-28 lamp (254 nm) and with ninhydrin and phosphomolybdic acid in ethanol. Flash chromatography was conducted on Merck silica gel 60 (40-63 μm) at medium pressure (300 mbar) or on CombiFlash apparatus (Serlabo Technologies), using standard settings. Chiral High Pressure Liquid Chromatography (HPLC) was performed on a Waters 2695 Separations Module equipped with a diode array UV detector (254 nm) and with a Daicel CHIRACEL IA column (4.6*250 nm, 5 mm). Data are reported as follows: column temperature, eluent, flow rate, retention time. Microwaves irradiation experiments were carried out in an Anton Paar Monowave 300 instrument with internal optic-fiber- or IR temperature control.

All reagents were obtained from commercial suppliers unless otherwise stated. Where necessary, organic solvents were routinely dried and/or distilled prior to use and stored over molecular sieves under nitrogen commercial DMF (anhydrous DMF was purchased from Sigma-Aldrich in Sure/Seak™ Bottles. Organic extracts were dried over magnesium sulfate ($MgSO_4$).

2. General Procedures

General Procedure A: Imine Formation

Aldehyde (1.0 equiv.), aniline (1.0 equiv.) and silica (1.0 equiv.) are successively added in a round bottom flask followed by the addition of ethanol (0.7M). The mixture is then placed in an ultrasound unit for 5-10 minutes (monitored by TLC) and filtered to remove silica. After concentration under reduced pressure, the crude imine is recrystallized in absolute ethanol.

General Procedure B: Azetidinimine Formation

Imine (1.0 equiv.), ynamide (2.0 equiv.), t-BuOLi (2.0 equiv.) and silica (1.0 equiv.) are successively added in a microwave sealed tube placed under argon before the addition of extra dry DMF (0.3M). The sealed tube is caped and placed in a microwave apparatus for 1 h at 100° C. After cooling, the crude material is transferred in a round bottom flask, concentrated under reduced pressure and purified by flash chromatography or preparative TLC on silica gel with appropriated solvents.

General Procedure C: Formation of Carboxylic Acids from Tert-Butyl Esters Under Acidic Hydrolysis Conditions A solution of the corresponding tert-butyl ester in DCM (1 mL/30 mg of tert-nutyl ester) is cooled to 0° C. then TFA (trifluoroacetic acid, 1 mL, excess) is added. After 1 h (thin layer chromatography (TLC) monitoring), the mixture is cooled to 0° C. then a saturated aqueous solution of $NaHCO_3$ is added dropwise until pH 7. The aqueous layer is extracted once with DCM (dichloromethane). The organic layers are washed with water and brine, dried over sodium sulfate, filtered then evaporated under reduced pressure. The resulting residue is purified by automated flash chromatography using a gradient of MeOH in DCM (MeOH 0%→40% over 20 min).

General Procedure D: Demethylation or the t-Butyl Ester Hydrolysis with $BBr_3$

An argon-flushed and stirred solution of azetidinimine in anhydrous dichloromethane (DCM) (at a concentration of around 0.1 M) is cooled to −78° C., then $BBr_3$ (1M solution in DCM, 4 equiv.) is added dropwise. The solution is further stirred at −78° C. for 2 h then allowed to warm to room temperature. Once the reaction completed (TLC monitoring), the reaction mixture is carefully quenched at −78° C. with a 1:1 mixture of MeOH/DCM (10 mL). After warming to room temperature, the solvents are evaporated then the crude residue is resolubilized in DCM, washed with saturated aqueous $NaHCO_3$ and water. The organic layer is dried on sodium sulfate, filtered then evaporated under reduced pressure. The resulting residue is subsequently purified by automated flash chromatography using a gradient of AcOEt in heptane (AcOEt 0%→60% over 30 min).

3. Analytical Data for some Azetidinimines Products According to the Present Invention E)-N-(1-(4-methoxyphenyl)-4-phenylazetidin-2-ylidene)aniline

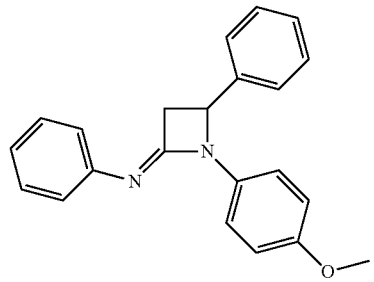 [SMILES: COc1ccc(N2/C(=N/c3ccccc3)CC2c2ccccc2)cc1]

$C_{22}H_{20}N_2O$—Exact Mass: 328,1576; $^1H$ NMR (300 MHz, $CDCl_3$): (ppm) 7.37-7.16 (m, 9H), 6.99-6.92 (m, 3H), 6.72 (d, J=9.1 Hz, 2H), 5.07 (dd, J=6.1, 2.9 Hz, 1H), 3.66 (s, 3H), 3.42 (dd, J=14.6, 6.1 Hz), 2.86 (dd, J=14.6, 2.9 Hz). $^{13}C$ NMR (75 MHz, $CDCl_3$): (ppm) 154.8 (C), 154.1 (C), 148.6 (C), 139.4 (C), 133.7 (C), 129.1 (2CH), 128.9 (2CH), 128.3 (CH), 125.9 (2CH), 122.8 (CH), 122.2 (2CH), 117.5 (2CH), 114.2 (2CH), 58.2 (CH), 55.5 ($CH_3$), 40.5 ($CH_2$). HRMS (ESI): calc. for $C_{22}H_{21}N_2O$ [M+H] m/z 328.1576, found m/z 329.1658. IR (neat): 2993, 2931, 2894, 1668, 1592, 1510, 1486, 1390, 1256, 1241, 1162, 1035 cm$^{-1}$.

(E)-N-(4-phenyl-1-(3,4,5-trimethoxyphenyl)azetidin-2-ylidene)aniline

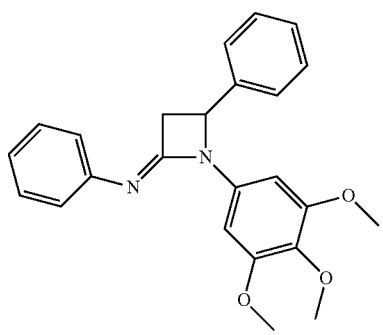 [SMILES: COc1cc(N2/C(=N/c3ccccc3)CC2c2ccccc2)cc(OC)c1OC]

$C_{24}H_{24}N_2O_3$—Exact Mass: 388,1787; $^1H$ NMR (300 MHz, $CDCl_3$): (ppm) 7.51-7.26 (m, 7H), 7.12-7.01 (m, 3H), 6.78 (s, 2H), 5.16 (dd, J=6.0, 2.9 Hz, 1H), 3.79 (s, 3H), 3.73 (s, 6H), 3.54 (dd, J=14.8, 6.0 Hz, 1H), 3.00 (dd, J=14.8, 2.9 Hz, 1H). $^{13}C$ NMR (75 MHz, $CDCl_3$): (ppm) 153.4 (2C), 148.0 (C), 136.2 (C), 132.8 (C), 129.1 (2CH), 129.0 (2CH), 128.5 (CH), 127.6 (C), 126.0 (2CH), 123.0 (CH), 122.2 (C), 122.1 (CH), 94.2 (2CH), 92.6 (C), 60.9 (CH), 58.6 (CH$_3$), 56.0 (2CH$_3$), 40.4 (CH$_2$). HRMS (ESI): calc. for C$_{24}$H$_{25}$N$_2$O$_3$ [M+H] m/z 389.1787, found m/z 389.1871

(E)-N-(4-(4-chlorophenyl)-1-(4-methoxyphenyl)azetidin-2-ylidene)aniline

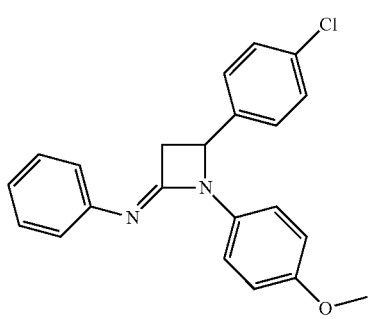 [SMILES: COc1ccc(N2/C(=N/c3ccccc3)CC2c2ccc(Cl)cc2)cc1]

C$_{22}$H$_{19}$ClNO$_2$—Exact Mass: 362,1186; $^1$H NMR (300 MHz, CDCl$_3$): (ppm) 7.34-7.25 (m, 6H), 7.24-7.16 (m, 2H), 6.73 (d, J=9.1 Hz, 2H), 5.04 (dd, J=6.0, 2.8 Hz, 1H), 3.67 (s, 3H), 3.42 (dd, J=14.6, 6.0 Hz, 1H), 2.81 (dd, J=14.6, 2.8 Hz, 1H). $^{13}$C NMR (75 MHz, CDCl$_3$): (ppm) 155.0 (C), 153.6 (C), 148.4 (C), 138.0 (C), 134.1 (C), 133.4 (C), 129.3 (2CH), 129.0 (2CH), 127.3 (2CH), 123.0 (CH), 122.2 (2CH), 117.5 (2CH), 114.3 (2CH), 57.5 (CH), 55.5 (CH$_3$), 40.5 (CH$_2$). HRMS (ESI): calc. for C$_{22}$H$_{20}$$^{35}$ClNO$_2$ [M+H] m/z 363.1186, found m/z 363.1246; calc. for C$_{22}$H$_{20}$$^{37}$ClNO$_2$ [M+H] m/z 365.1156, found m/z 365.1251

(E)-N-(4-(4-methoxyphenyl)-1-phenylazetidin-2-ylidene)aniline

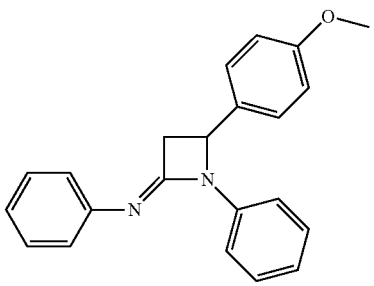 [SMILES: COc1ccc(C2C/C(=N\c3ccccc3)N2c2ccccc2)cc1]

C$_{22}$H$_{20}$N$_2$O—Exact Mass: 328,1576; $^1$H NMR (300 MHz, CDCl$_3$): (ppm) 7.38 (d, J=8.3 Hz, 2H), 7.32-7.11 (m, 6H), 7.01-6.93 (m, 3H), 6.92-6.80 (m, 3H), 5.06 (dd, J=6.0, 2.8 Hz, 1H), 3.73 (s, 3H), 3.41 (dd, J=14.8, 6.0 Hz, 1H), 2.84 (dd, J=14.8, 2.8 Hz, 1H). $^{13}$C NMR (75 MHz, CDCl$_3$): (ppm) 159.6 (C), 154.5 (C), 149.3 (C), 139.9 (C), 131.3 (C), 128.9 (2CH), 128.8 (2CH), 127.2 (2CH), 123.0 (CH), 122.2 (2CH), 122.1 (CH), 116.4 (2CH), 114.5 (2CH), 57.8 (CH), 55.3 (CH$_3$), 40.5 (CH$_2$). HRMS (ESI): calc. for C$_{22}$H$_{21}$N$_2$O [M+H] m/z 329.1576, found m/z 329.1638.

(E)-N-(1,4-bis(4-methoxyphenyl)azetidin-2-ylidene)aniline

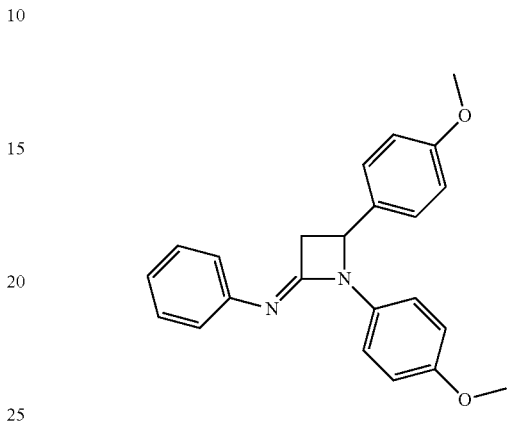

C$_{23}$H$_{22}$N$_2$O$_2$—Exact Mass: 358,1681; $^1$H NMR (300 MHz, CDCl$_3$): (ppm) 7.42-7.25 (m, 6H), 7.05-6.96 (m, 3H), 6.88 (d, J=8.6 Hz, 2H), 6.78 (d, J=8.9 Hz, 2H), 5.08 (dd, J=5.6, 3.0 Hz, 1H), 3.78 (s, 3H), 3.72 (s, 3H), 3.45 (dd, J=14.7, 5.6 Hz, 1H), 2.90 (dd, J=14.7, 3.0 Hz, 1H). $^{13}$C NMR (75 MHz, CDCl$_3$): (ppm) 159.3 (C), 154.5 (C), 148.1 (C), 133.2 (C), 131.0 (C), 129.1 (CH), 127.4 (CH), 126.9 (C), 123.0 (CH), 122.5 (CH), 117.8 (CH), 114.7 (CH), 114.4 (CH), 58.1 (CH), 55.7 (CH$_3$), 55.5 (CH$_3$), 40.8 (CH$_2$). HRMS (ESI): calc. for C$_{23}$H$_{23}$N$_2$O$_2$ [M+H] m/z 359.1681, found m/z 359.1752.

(E)-4-(4-chlorophenyl)-N-(4-iodophenyl)-1-(4-methoxyphenyl)azetidin-2-imine

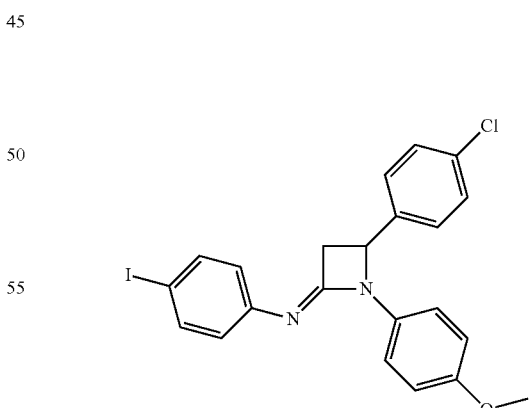

$^1$H NMR (300 MHz, CDCl$_3$): δ 7.57 (d, J=8.4 Hz, 2H), 7.36-7.33 (m, 6H), 6.82 (d, J=9.3 Hz, 2H), 6.78 (d, J=8.7 Hz, 2H), 5.14 (dd, J=6.0, 3.0 Hz, 1H), 3.76 (s, 3H), 3.49 (dd, J=14.7, 6.0 Hz, 1H), 2.87 (dd, J=14.7, 3.0 Hz, 1H). HRMS: [M+H]$^+$ m/z 489.0230, found 489.0240.

(E)-N-(4-iodophenyl)-1-(4-methoxyphenyl)azetidin-2-imine

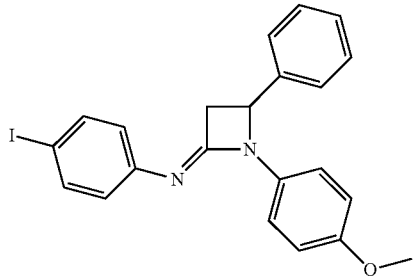 [SMILES: COc1ccc(N2/C(=N/c3ccc(I)cc3)CC2c2ccccc2)cc1]

¹H NMR (300 MHz, CDCl₃): δ 7.58 (d, J=8.4 Hz, 2H), 7.41-7.36 (m, 7H), 6.81 (d, J=4.5 Hz, 2H), 6.79 (d, J=4.2 Hz, 2H), 5.15 (dd, J=5.6, 3.0 Hz, 1H), 3.75 (s, 3H), 3.48 (dd, J=14.7, 6.0 Hz, 1H), 2.93 (dd, J=14.7, 3.0 Hz, 1H). HRMS: [M+H]⁺ m/z 455.0542, found 455.0624.

(E)-4-(4-chlorophenyl)-N-(4-chlorophenyl)-1-(4-methoxyphenyl)azetidin-2-imine

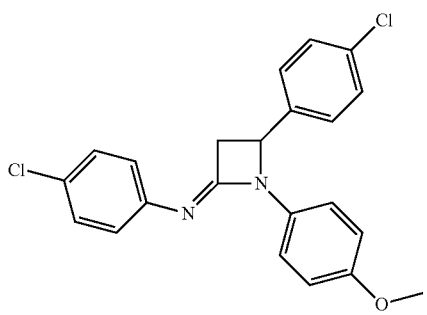 [SMILES: COc1ccc(N2/C(=N/c3ccc(Cl)cc3)CC2c2ccc(Cl)cc2)cc1]

¹H NMR (300 MHz, CDCl₃): δ 7.37-7.23 (m, 8H), 6.94 (d, J=8.7 Hz, 2H), 6.81 (d, J=9.0 Hz, 2H), 5.15 (dd, J=6.0, 3.0 Hz, 1H), 3.76 (s, 3H), 3.50 (dd, J=14.7, 6.0 Hz, 1H), 2.89 (dd, J=14.7, 6.0 Hz, 1H). HRMS: [M+H]⁺ m/z 398.0874, found 398.0898.

(E)-4-N-(4-chlorophenyl)-1-(4-methoxyphenyl)azetidin-2-imine

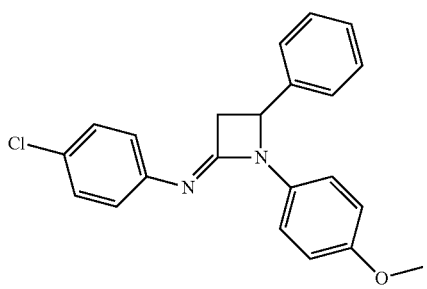 [SMILES: COc1ccc(N2/C(=N/c3ccc(Cl)cc3)CC2c2ccccc2)cc1]

¹H NMR (300 MHz, CDCl₃): δ 7.41-7.23 (m, 9H), 6.97 (d, J=8.4 Hz, 2H), 6.82 (d, J=8.7 Hz, 2H), 5.16 (dd, J=5.9, 2.7 Hz, 1H), 3.75 (s, 3H), 3.49 (dd, J=14.7, 5.9 Hz, 1H), 2.92 (dd, J=14.7, 2.7 Hz, 1H). HRMS: [M+H]⁺ m/z 363.1264, found 363.1268.

(E)-4-(4-chlorophenyl)-N-(4-trifluoromethylphenyl)-1-(4-methoxyphenyl)azetidin-2-imine

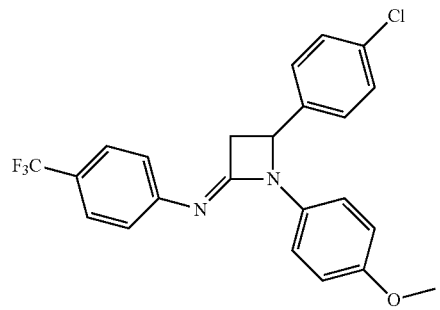 [SMILES: COc1ccc(N2/C(=N/c3ccc(C(F)(F)F)cc3)CC2c2ccc(Cl)cc2)cc1]

¹H NMR (300 MHz, CDCl₃): δ 7.42-7.27 (m, 8H), 7.18 (d, J=7.8 Hz, 2H), 6.82 (d, J=9.0 Hz, 2H), 5.17 (dd, J=6.0, 2.7 Hz, 1H), 3.77 (s, 3H), 3.53 (dd, J=14.7, 6.0 Hz, 1H), 2.91 (dd, J=14.7, 2.7 Hz, 1H). HRMS: [M+H]⁺ m/z 431.1138, found 431.1131.

(E)-1-(4-ethoxyphenyl)-N-(4-methoxyphenyl)-4-(naphthalen-2-yl)azetidin-2-imine

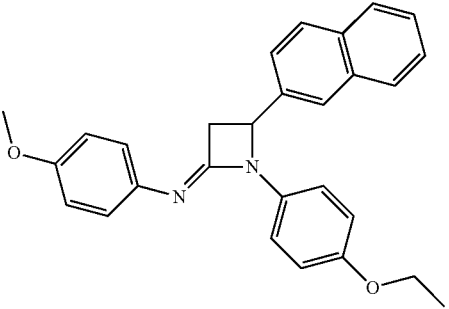 [SMILES: CCOc1ccc(N2/C(=N/c3ccc(OC)cc3)CC2c2ccc3ccccc3c2)cc1]

¹H NMR (300 MHz, CDCl₃): δ 7.89-7.83 (m, 2H), 7.56-7.43 (m, 7H), 7.02 (d, J=9.0 Hz, 2H), 6.88 (d, J=9.0 Hz, 2H), 6.79 (d, J=9.0 Hz, 2H), 5.30 (dd, J=6.0, 3.0 Hz, 1H), 3.95 (q, J=13.8, 6.9 Hz, 2H), 3.80 (s, 3H), 3.57 (dd, J=14.7, 6.0 Hz, 1H), 2.99 (dd, J=14.7, 3.0 Hz, 1H), 1.37 (t, J=13.8, 6.9 Hz, 2H). HRMS: [M+H]⁺ m/z 423.1993, found 423.1987.

(E)-1-(4-ethoxyphenyl)-N-(4-iodophenyl)-4-(naphthalen-2-yl)azetidin-2-imine

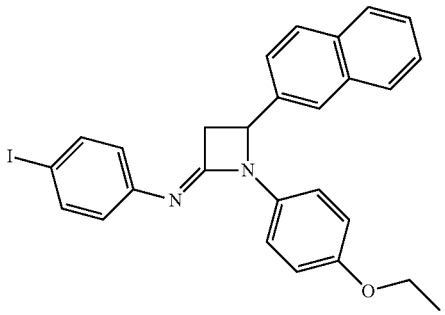 [SMILES: CCOc1ccc(N2/C(=N/c3ccc(I)cc3)CC2c2ccc3ccccc3c2)cc1]

¹H NMR (300 MHz, CDCl₃): δ 7.89-7.40 (m, 7H), 6.82 (d, J=8.4 Hz, 2H), 6.79 (d, J=9.0 Hz, 2H), 5.32 (dd, J=5.7, 2.7 Hz, 1H), 3.95 (q, J=5.7, 2.7 Hz, 2H), 3.54 (dd, J=14.4, 6.0 Hz, 1H), 2.99 (dd, J=14.4, 2.7 Hz, 1H), 1.36 (t, J=6.0, 2.7 Hz, 2H). HRMS: [M+H]⁺ m/z 519.0944, found 519.0941.

(E)-4-(3,5-dichlorophenyl)-N-(4-iodophenyl)-1-(4-methoxyphenyl)azetidin-2-imine

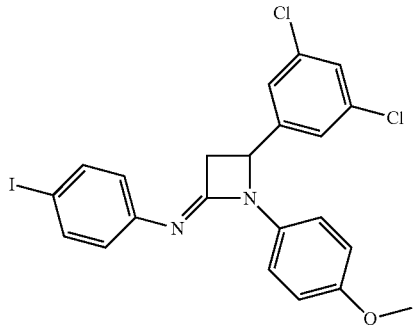 [SMILES: COc1ccc(N2/C(=N/c3ccc(I)cc3)CC2c2cc(Cl)cc(Cl)c2)cc1]

¹H NMR (300 MHz, CDCl₃): δ 7.56 (d, J=8.7 Hz, 2H), 7.45 (d, J=1.8 Hz, 2H), 7.37-7.21 (m, 3H), 6.86 (d, J=9.3 Hz, 2H), 6.75 (d, J=8.4 Hz, 2H), 5.49 (dd, J=6.3, 3.0 Hz, 1H), 3.78 (s, 3H), 3.60 (dd, J=14.7, 6.3 Hz, 1H), 2.93 (dd, J=14.7, 3.0 Hz, 1H). HRMS: [M+H]⁺ m/z 538.9968, found 538.9920.

(E)-1-(4-(benzyloxy)phenyl)-N-4-diphenylazetidin-2-imine

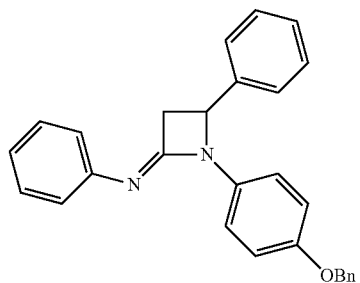 [SMILES: c1ccc(COc2ccc(N3/C(=N/c4ccccc4)CC3c3ccccc3)cc2)cc1]

¹H NMR (300 MHz, CDCl₃): δ 7.49-7.20 (m, 14H), 7.11-6.98 (m, 3H), 6.93-6.81 (m, 2H), 5.15 (dd, J=6.0, 2.9 Hz, 1H), 5.00 (s, 2H), 3.5 (dd, J=14.6, 6.0 Hz, 1H), 2.94 (dd, J=14.6, 2.9 Hz, 1H). HRMS-EI (m/z) calcd for C₂₈H₂₅N₂O [(M+H)⁺] 405.1967, found 405.1952.

(E)-1-(3,4-dimethoxyphenyl)-N-4-diphenylazetidin-2-imine

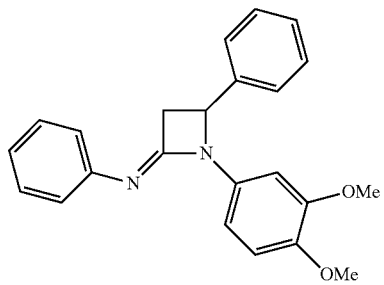 [SMILES: COc1ccc(N2/C(=N/c3ccccc3)CC2c2ccccc2)cc1OC]

¹H NMR (300 MHz, CDCl₃): δ 7.52 (d, J=2.3 Hz, 1H), 7.48-7.22 (m, 7H), 7.06-6.99 (m, 3H), 6.72 (d, J=8.6 Hz, 1H), 6.64 (dd, J=8.6, 2.3 Hz, 1H), 5.15 (dd, J=6.1, 2.9 Hz, 1H), 3.8 (2 overlaps s, 6H), 3.52 (dd, J=14.6, 6.1 Hz, 1H), 2.97 (dd, J=14.7, 2.9 Hz, 1H). HRMS-EI (m/z) calcd for C₂₃H₂₃N₂O₂ [(M+H)⁺] 359.1760, found 359.1763.

(E)-1-(benzo[d][1,3]dioxol-5-yl)-N,4-diphenylazetidin-2-imine

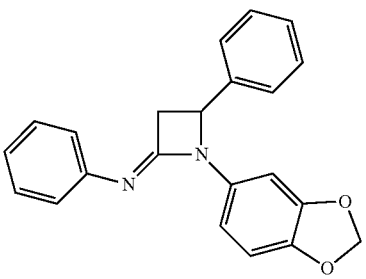 [SMILES: c1ccc(/N=C2\CC(c3ccccc3)N2c2ccc3c(c2)OCO3)cc1]

¹H NMR (300 MHz, CDCl₃): δ 7.46-7.22 (m, 8H), 7.12-6.97 (m, 3H), 6.77 (dd, J=8.4, 2.1 Hz, 1H), 6.67 (d, J=8.4 Hz, 1H), 5.88 (dd, J=2.7, 1.4 Hz, 2H), 5.12 (dd, J=6.1, 2.9 Hz, 1H), 3.50 (dd, J=14.7, 6.1 Hz, 1H), 2.93 (dd, J=14.7, 2.9 Hz, 1H). HRMS-EI (m/z) calcd for C₂₂H₁₉N₂O₂ [(M+H)⁺] 343.1448, found 343.1453.

(E)-1-(2,3-dihydrobenzo[b][1,4]dioxin-6-yl)-N-4-diphenylazetidin-2-imine

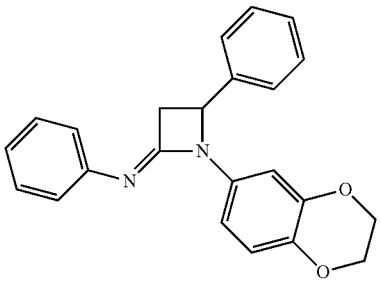 [SMILES: c1ccc(/N=C2\CC(c3ccccc3)N2c2ccc3c(c2)OCCO3)cc1]

¹H NMR (300 MHz, CDCl₃): δ 7.49-7.22 (m, 7H), 7.08-6.98 (m, 4H), 6.95 (dd, J=8.7, 2.5, 1H), 6.74 (d, J=8.7 Hz, 1H), 5.11 (dd, J=6.1, 2.9 Hz, 1H), 4.27-4.13 (m, 4H), 3.48 (dd, J=14.7, 6.1 Hz, 1H), 2.92 (dd, J=14.7, 2.9 Hz, 1H). HRMS-EI (m/z) calcd for C₂₃H₂₁N₂O₂ [(M+H)⁺] 357.103, found 357.1588.

(E)-1-(3-methoxyphenyl)-N,4-diphenylazetidin-2-imine

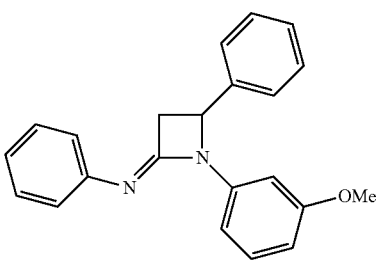 [SMILES: COc1cccc(N2/C(=N/c3ccccc3)CC2c2ccccc2)c1]

¹H NMR (300 MHz, CDCl₃): δ 7.45-7.21 (m, 8H), 7.14 (t, J=8.1 Hz, 1H), 7.09-7.00 (m, 3H), 6.96-6.89 (m, 1H), 6.53 (ddd, J=8.1, 2.5, 0.8 Hz, 1H), 5.17 (dd, J=6.2, 3.0 Hz, 1H), 3.75 (s, 3H), 3.51 (dd, J=14.8, 6.2 Hz, 1H), 2.95 (dd, J=14.8, 3.0 Hz, 1H). HRMS-EI (m/z) calcd for $C_{22}H_{20}N_2O$ [(M+H)⁺] 329.1654, found 329.1658.

(E)-4-(4-chlorophenyl)-1-(3-methoxyphenyl)-N-phenylazetidin-2-imine

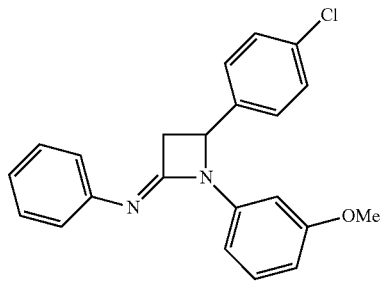 [SMILES: COc1cccc(N2/C(=N/c3ccccc3)CC2c2ccc(Cl)cc2)c1]

¹H NMR (300 MHz, CDCl₃): δ 7.38-7.23 (m, 6H), 7.23-6.97 (m, 5H), 6.88 (dd, J=8.0, 1.0 Hz, 1H), 6.54 (ddd, J=8.0, 2.5, 1.0 Hz, 1H), 5.14 (dd, J=6.2, 3.0 Hz, 1H), 3.76 (s, 3H), 3.52 (dd, J=14.8, 6.2 Hz, 1H), 2.90 (dd, J=14.8, 3.0 Hz, 1H). HRMS-EI (m/z) calcd for $C_{22}H_{20}ClN_2O$ [(M+H)⁺] 363.1264, found 363.1250.

(E)-4-(4-chlorophenyl)-1-(2-methoxyphenyl)-N-phenylazetidin-2-imine

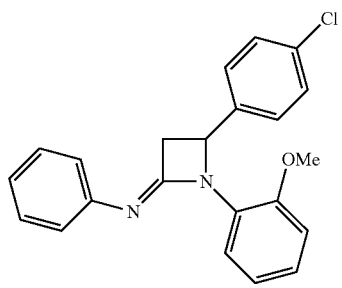 [SMILES: COc1ccccc1N1/C(=N/c2ccccc2)CC1c1ccc(Cl)cc1]

¹H NMR (300 MHz, CDCl₃): δ 8.31-8.23 (m, 1H), 7.28-7.14 (m, 6H), 7.00-6.86 (m, 5H), 6.69-6.64 (m, 1H), 5.52 (dd, J=6.0, 2.8 Hz, 1H), 3.48 (s, 3H), 3.44 (dd, J=14.7, 6.0 Hz, 1H), 2.80 (dd, J=14.7, 2.8 Hz, 1H). HRMS-EI (m/z) calcd for $C_{22}H_{20}ClN_2O$ [(M+H)⁺] 363.1264, found 363.1273.

Methyl (E)-4-(1-phenyl-4-(phenylimino)azetidin-2-yl)benzoate

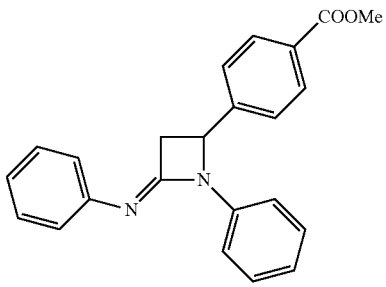 [SMILES: COC(=O)c1ccc(C2C/C(=N\c3ccccc3)N2c2ccccc2)cc1]

¹H NMR (300 MHz, CDCl₃): δ 8.06 (d, J=8.7 Hz, 2H), 7.5 (d, J=8.7 Hz, 2H), 7.42 (d, J=8.7 Hz, 2H), 7.33-7.22 (m, 4H), 7.08-6.95 (m, 4H), 5.24 (dd, J=6.3 Hz, 3.0 Hz, 1H), 3.92 (s, 3H), 3.55 (dd, J=14.8, 6.3 Hz, 1H), 2.93 (dd, J=14.8, 3.0 Hz, 1H). HRMS-ESI (m/z) calcd for $C_{23}H_{21}N_2O_2$ [(M+H)⁺] 357.1603, found 357.1589.

(E)-N-(1,4-diphenylazetidin-2-ylidene)aniline

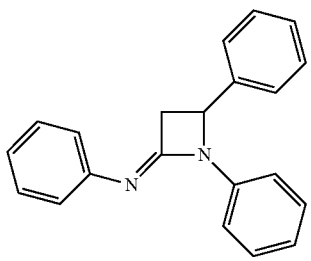 [SMILES: c1ccc(/N=C2\CC(c3ccccc3)N2c2ccccc2)cc1]

¹H NMR (300 MHz, CDCl₃): δ 7.48-7.23 (m, 12H), 7.08-6.95 (m, 3H), 5.19 (dd, J=6.4, 2.8 Hz, 1H), 3.52 (dd, J=14.8, 6.4 Hz, 1H), 2.96 (dd, J=14.8, 2.8 Hz, 1H). HRMS-ESI (m/z) calcd for $C_{21}H_{19}N_2$ [(M+H)⁺] 299.1548, found: 299.1563.

(E)-tert-butyl 4-(1-(4-methoxyphenyl)-4-(phenylimino)azetidin-2-yl)benzoate (MBG132 MBG135)

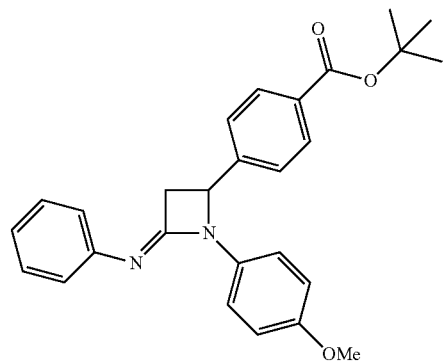 [SMILES: COc1ccc(N2/C(=N/c3ccccc3)CC2c2ccc(C(=O)OC(C)(C)C)cc2)cc1]

¹H NMR (300 MHz, CDCl₃): δ 8.03 (d, J=8.0 Hz, 2H), 7.49 (d, J=8.0 Hz, 2H), 7.40-7.29 (m, 5H), 7.06 (m, 3H), 6.82 (d, J=8.0 Hz, 1H), 5.21 (dd, J=15.0, 6.0 Hz, 1H), 3.77 (s, 3H), 3.55 (dd, J=15.0, 6.0 Hz, 1H), 2.94 (dd, J=15.0, 3.0, 1H), 1.61 (s, 9H). HRMS-ESI (m/z) calcd for $C_{27}H_{29}N_2O_3$ [(M+H)⁺] 429.2178, found: 429.2187.

tert-butyl (E)-4-(1-phenyl-4-(phenylimino)azetidin-2-yl)benzoate

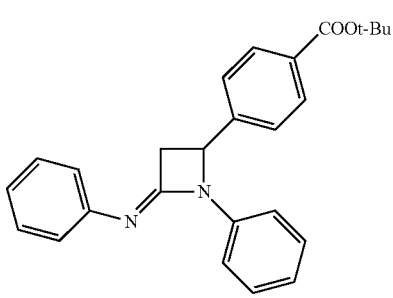

¹H NMR (300 MHz, CDCl₃): δ 8.00 (d, J=8.3 Hz, 2H), 7.47 (d, J=8.3 Hz, 2H), 7.44-7.20 (m, 6H), 7.08-6.93 (m, 4H), 5.23 (dd, J=6.2, 3.0 Hz, 1H), 3.54 (dd, J=14.7, 6.2 Hz, 1H), 2.92 (dd, J=14.7, 3.0 Hz, 1H), 1.58 (s, 9H); HRMS-ESI (m/z) calcd for $C_{26}H_{27}N_2O_2$ [(M+H)⁺] 399.2073, found 399.2111.

(E)-2-(2-(4-(2-phenyl-4-(phenylimino)azetidin-1-yl)phenoxy)ethoxy)ethan-1-ol

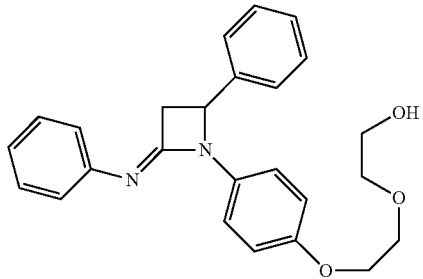 [SMILES: OCCOCCOc1ccc(N2/C(=N/c3ccccc3)CC2c2ccccc2)cc1]

¹H NMR (300 MHz, CDCl₃): δ 7.47-7.22 (m, 9H), 7.09-6.96 (m, 3H), 6.89-6.65 (m, 3H), 5.15 (dd, J=6.1, 2.9 Hz, 1H), 4.37-4.19 (m, 2H), 4.15-4.01 (m, 2H), 3.92-3.70 (m, 4H), 3.50 (dd, J=14.7, 6.1 Hz, 1H), 2.93 (dd, J=14.7, 2.9 Hz, 1H); HRMS-ESI (m/z) calcd for $C_{25}H_{27}N_2O_3$ [(M+H)⁺] 403.2022, found 403.2008.

(E)-tert-butyl 2-(4-(2-(4-chlorophenyl)-4-(phenylimino)azetidin-1-yl)phenoxy)acetate

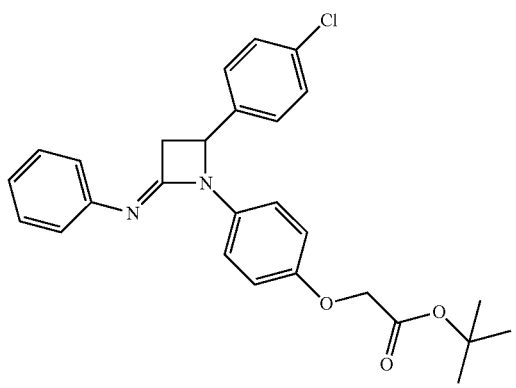 [SMILES: CC(C)(C)OC(=O)COc1ccc(N2/C(=N/c3ccccc3)CC2c2ccc(Cl)cc2)cc1]

To a stirred solution of azetidinimine 1 (30 mg, 0.086 mmol, see below for structure), and potassium carbonate (13 mg, 0.095 mmol, 1.1 equiv.) in dimethylformamide (DMF) (500 μL) is added t-butyl bromoacetate (18.5 mg, 14 μL, 0.095 mmol, 1.1 equiv.). The reaction mixture is stirred at 60° C. overnight (thin layer chromatography (TLC) monitoring) then purified by automated flash column chromatography using a gradient of AcOEt in heptane (AcOEt 0%→20% over 20 min). Orange wax. (31 mg, 78%).

¹H NMR (300 MHz, CDCl₃): δ 7.37-7.26 (m, 8H), 7.06 (m, 3H), 6.83-6.79 (m, 2H), 5.12 (dd, J=6.2, 2.8 Hz, 1H), 4.44 (s, 2H), 3.50 (dd, J=14.5, 6.2 Hz, 1H), 2.90 (dd, J=14.5, 2.8 Hz, 1H), 1.47 (s, 9H). HRMS-ESI (m/z) calcd for $C_{27}H_{28}ClN_2O_3$ [(M+H)⁺] 463.1788, found: 463.1793.

(E)-tert-butyl 2-(4-(2-phenyl-4-(phenylimino)azetidin-1-yl)phenoxy)acetate

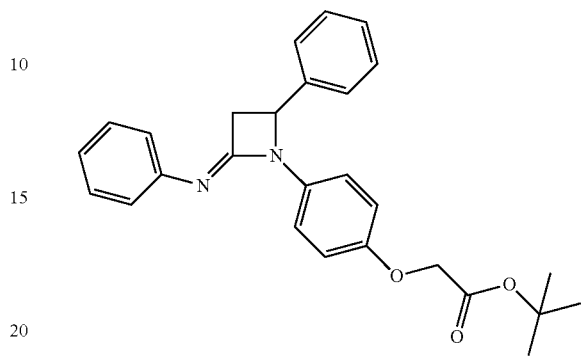

To a stirred solution of azetidinimine 2 (36 mg, 0.115 mmol), and potassium carbonate (32 mg, 0.095 mmol, 2 equiv.) in DMF (400 μL) is added t-butyl bromoacetate (34 mg, 25 μL, 0.095 mmol, 1.5 equiv.). The reaction mixture is stirred at 100° C. overnight (TLC monitoring) then purified by automated flash column chromatography using a gradient of AcOEt in heptane (AcOEt 0%→20% over 20 min). Orange wax. (30.7 mg, 62%).

¹H NMR (300 MHz, CDCl₃): δ ¹H NMR (300 MHz, CDCl₃): δ 7.43-7.26 (m, 10H), 7.02 (d, J=8.4 Hz, 2H), 6.80 (d, J=8.4 Hz, 2H), 5.14 (dd, J=6.0, 3.0 Hz, 1H), 4.44 (s, 2H), 3.50 (dd, J=15.0, 6.0 Hz, 1H), 2.93 (dd, J=6.0, 3.0 Hz, 1H), 1.47 (s, 9H). HRMS-ESI (m/z) calcd for $C_{27}H_{29}N_2O_3$ [(M+H)⁺] 429.2178, found: 429.2182.

(E)-4-(1-phenyl-4-(phenylimino)azetidin-2-yl)benzoic acid 4

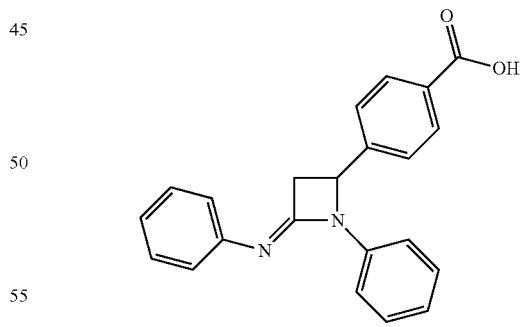

This compound was obtained using general procedure C as a white foam in 96%.

¹H NMR (300 MHz, MeOD): δ 8.03 (d, J=8.2 Hz, 2H), 7.52 (d, J=8.2 Hz, 2H), 7.38 (d, J=8.2 Hz, 2H), 7.31-7.21 (m, 4H), 7.06-6.94 (m, 4H), 5.36 (dd, J=6.0, 3.0 Hz, 1H), 3.59 (dd, J=15.0, 6.0 Hz, 1H), 2.89 (dd, J=15.0, 3.0 Hz, 1H). One proton missing due to chemical exchange with CD₃OD. HRMS-ESI (m/z) calcd for $C_{22}H_{19}N_2O_2$ [(M+H)⁺] 343.1447, found 343.1430.

(E)-2-(4-(2-(4-chlorophenyl)-4-(phenylimino)azetidin-1-yl)phenoxy)acetic acid

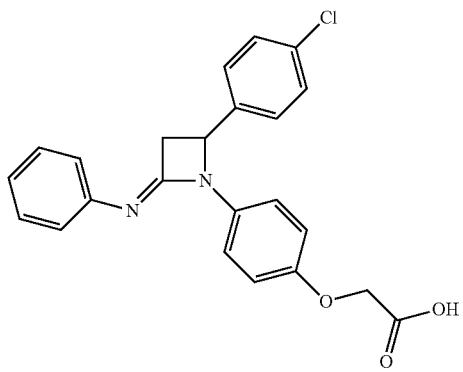 [SMILES: O=C(O)COc1ccc(N2/C(=N/c3ccccc3)CC2c2ccc(Cl)cc2)cc1]

This compound was obtained using general procedure C as a white foam in 69%.

$^1$H NMR (300 MHz, MeOD): δ 7.44-7.27 (m, 8H), 7.08-7.05 (m, 3H), 6.87 (d, J=9.3 Hz, 2H), 5.31 (dd, J=5.7, 2.9 Hz, 1H), 4.46 (s, 2H), 3.58 (dd, J=14.7, 5.7 Hz, 1H), 2.95 (dd, J=14.7, 2.9 Hz, 1H). HRMS-ESI (m/z) calcd for $C_{23}H_{19}ClN_2O_3$ [(M+H)$^+$] 407.1162, found 407.1159.

(E)-2-(4-(2-phenyl-4-(phenylimino)azetidin-1-yl)phenoxy)acetic acid

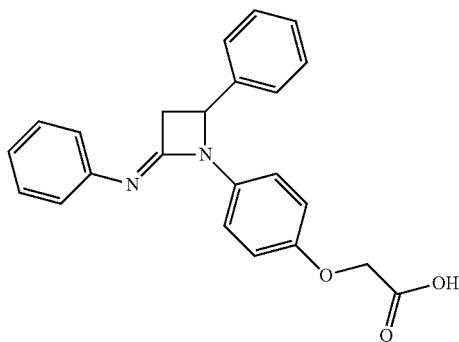 [SMILES: O=C(O)COc1ccc(N2/C(=N/c3ccccc3)CC2c2ccccc2)cc1]

This compound was obtained using general procedure C as a white foam in 65%.

$^1$H NMR (300 MHz, MeOD): δ 7.43-7.25 (m, 10H), 7.04-6.99 (m, 3H), 6.84 (d, J=9.4 Hz, 2H), 5.23 (dd, J=6.0, 2.8 Hz, 1H), 4.34 (s, 2H), 3.53 (dd, J=14.6, 6.0 Hz, 1H), 2.85 (dd, J=14.6, 2.8 Hz, 1H). HRMS-ESI (m/z) calcd for $C_{23}H_{21}N_2O_3$ [(M+H)$^+$] 373.1552, found 373.1545.

(E)-4-(2-phenyl-4-(phenylimino)azetidin-1-yl)phenol 2

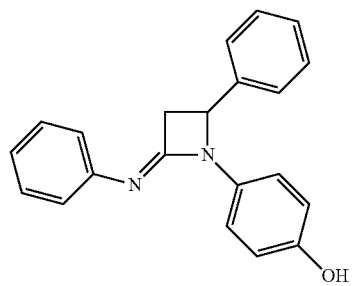 [SMILES: Oc1ccc(N2/C(=N/c3ccccc3)CC2c2ccccc2)cc1]

This compound was obtained using general procedure D as a yellow oil in 38%.

$^1$H NMR (300 MHz, CDCl$_3$): δ 7.41-7.23 (m, 10H), 7.07-7.03 (m, 3H), 6.68 (d, J=8.9 Hz, 2H), 5.16 (dd, J=6.0, 2.9 Hz, 1H), 3.50 (dd, J=14.7, 6.0 Hz, 1H), 2.92 (dd, J=14.7, 2.9 Hz, 1H), OH signal missing. HRMS-ESI (m/z) calcd for $C_{21}H_{19}N_2O$ [(M+H)$^+$] 315.1497, found 315.1503.

(E)-4-(2-(4-chlorophenyl)-4-(phenylimino)azetidin-1-yl)phenol 1

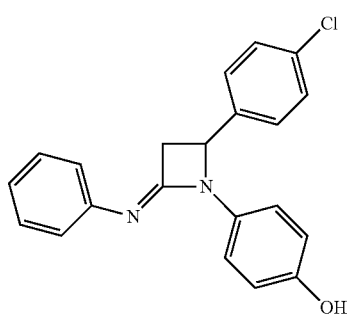 [SMILES: Oc1ccc(N2/C(=N/c3ccccc3)CC2c2ccc(Cl)cc2)cc1]

This compound was obtained using general procedure D as a yellow foam in 60%.

$^1$H NMR (300 MHz, CDCl$_3$): δ 7.34-7.26 (m, 8H), 7.07-7.00 (m, 3H), 6.71 (d, J=9.0 Hz, 1H), 5.13 (dd, J=6.0, 3.0 Hz, 1H), 3.50 (dd, J=14.8, 6.2 Hz, 1H), 2.90 (dd, J=14.8, 3.0 Hz, 1H), OH signal missing. HRMS-ESI (m/z) calcd for $C_{21}H_{18}ClN_2O$ [(M+H)$^+$] 349.1108, found 349.1092.

(E)-4-(1-(4-methoxyphenyl)-4-(phenylimino)azetidin-2-yl)benzoic acid 3

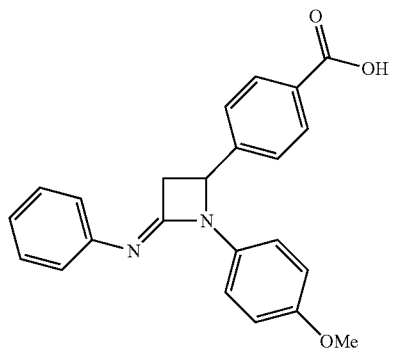 [SMILES: COc1ccc(N2/C(=N/c3ccccc3)CC2c2ccc(C(=O)O)cc2)cc1]

This compound was obtained using general procedure D as a yellow foam in 29%.

$^1$H NMR (300 MHz, CDCl$_3$): δ 8.04 (d, J=8.0 Hz, 2H), 7.47 (d, J=8.0 Hz, 2H), 7.31-7.23 (m, 5H), 7.07-7.02 (m, 3H), 6.72 (d, J=8.0 Hz, 2H), 5.22 (dd, J=15.0, 3.0 Hz, 1H), 3.91 (s, 3H), 3.54 (dd, J=15.0, 6.0 Hz, 1H), 2.92 (dd, J=15.0, 3.0 Hz, 1H), carboxylic proton missing. HRMS-ESI (m/z) calcd for $C_{23}H_{21}N_2O_3$ [(M+H)$^+$] 373.1552, found: 373.1546.

(E)-2-((tert-butoxycarbonyl)amino)ethyl 4-(1-phenyl-4-(phenylimino)azetidin-2-yl)benzoate 5

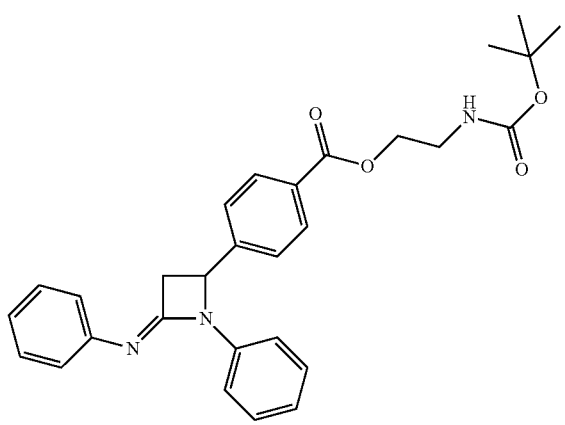 [SMILES: CC(C)(C)OC(=O)NCCOC(=O)c1ccc(C2C/C(=N\c3ccccc3)N2c2ccccc2)cc1]

To an argon-flushed and stirred solution of compound 4 in DCM (0.5 mL) is added triethylamine (1.2 mg, 2 µL, 0.07 mmol, 1 equiv.), CDI (11.7 mg, 0.07 mmol, 1 equiv.) and tert-butyl (2-hydroxyethyl)carbamate (11.7 mg, 0.07 mmol, 1 equiv.). The reaction mixture is stirred 16 h at rt then purified by automated flash column chromatography using a gradient of AcOEt in heptane (AcOEt 0%→50% over 30 min) to afford a white foam. (14 mg, 38%).

$^1$H NMR (300 MHz, CDCl$_3$): δ 8.06 (d, J=9.0 Hz, 2H), 7.51 (d, J=9.0 Hz, 2H), 7.41 (d, J=9.0 Hz, 2H), 7.33-7.23 (m, 4H), 7.08-6.96 (m, 4H), 5.25 (dd, J=6.0, 3.0 Hz, 1H), 4.82 (m, 1H), 4.38 (t, J=5.0, 2H), 3.60-3.52 (m, 3H), 2.93 (dd, J=15.4, 3.0 Hz, 1H), 1.43 (s, 9H). HRMS-ESI (m/z) calcd for C$_{29}$H$_{32}$N$_3$O$_4$ [(M+H)$^+$] 486.2393, found 486.2375.

(E)-2-((4-(1-phenyl-4-(phenylimino)azetidin-2-yl)benzoyl)oxy)ethanaminium 2,2,2-trifluoroacetate

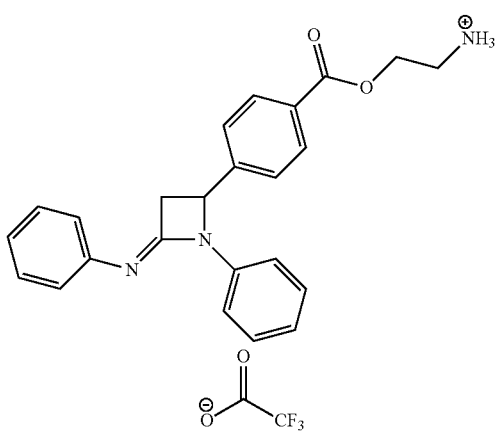

To a solution of azetidinimine 5 (19 mg, 0.038 mmol) in DCM (100 µL) is added TFA (trifluoroacetic acid, 100 µL, excess). The reaction mixture is stirred at room temperature for 16 h then at 40° C. for 24 h. Subsequent evaporation of solvents furnished the title compound in the form of a TFA salt (19 mg, quant.).

$^1$H NMR (300 MHz, MeOD): δ 8.03 (d, J=8.3 Hz, 2H), 7.55-7.47 (m, 4H), 7.42-7.40 (m, 1H), 7.34-7.30 (m, 2H), 7.03-6.97 (m, 2H), 6.58-6.53 (m, 3H), 4.94 (dd, J=8.0, 6.0 Hz, 1H), 4.54-4.50 (m, 2H), 3.35 (t, J=5.7 Hz, 2H), 2.90 (dd, J=15.2, 8.0 Hz, 1H), 2.79 (dd, J=15.2, 6 Hz, 1H). Three protons missing due to chemical exchange with MeOD. $^{19}$F NMR (282 MHz, MeOD): δ -76.87 (s, 3F). HRMS-ESI (m/z) calcd for C$_{24}$H$_{24}$N$_3$O$_2$ [(M+H)$^+$] 386.1869, found: 386.1862.

(E)-(4-(1-phenyl-4-(phenylimino)azetidin-2-yl)phenyl)methanol 6

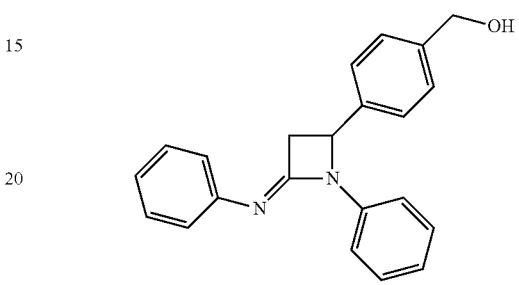

A solution of azetidinimine 4 (40 mg, 0.2 mmol) under argon in anhydrous THF (terahydrofuran, 0.6 mL) is cooled to 0° C. then LiAlH$_4$ (23 mg, 0.6 mmol, 3 equiv.) is added. The reaction mixture is stirred 3 h at room temperature (TLC monitoring) then AcOEt and a saturated aqueous solution of Na$_2$SO$_4$ are carefully added to quench the reaction. The resulting slurry is filtrated through a pad of celite and washed with additional AcOEt. The organic layer is dried over sodium sulfate, filtered then evaporated. Automated flash column chromatography using a gradient of AcOEt in heptane (AcOEt 0%→30% over 20 min) furnished the title compound as a white foam (51.2 mg, 79%).

$^1$H NMR (300 MHz, CDCl$_3$): δ 7.48-7.38 (m, 6H), 7.34-7.23 (m, 4H), 7.09-6.95 (m, 4H), 5.20 (dd, J=6.0, 3.0 Hz, 1H), 4.70 (s, 2H), 3.52 (dd, J=14.7, 6.0 Hz, 1H), 2.93 (dd, J=14.7, 3.0 Hz, 1H), OH proton missing. HRMS-ESI (m/z) calcd for C$_{22}$H$_{21}$N$_2$O [(M+)$^+$] 329.1654, found: 329.1643.

(E)-N-(4-(4-(chloromethyl)phenyl)-1-phenylazetidin-2-ylidene)aniline

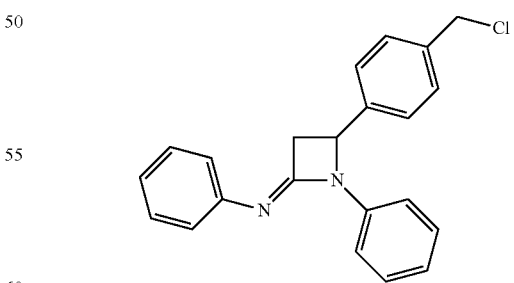

A solution of azetidimine 6 (22 mg, 0.068 mmol) and triethylamine (14 mg, 19 µL, 0.135 mmol, 2 equiv.) in DCM and under argon is cooled to 0° C. then MsCl (mesyl chloride, 8.5 mg, 6 µL, 0.074 mmol, 1.1 equiv.) is added. The reaction mixture is stirred at rt overnight. Afterwards, additional DCM (10 mL) is added then the reaction mixture is washed twice with water, dried over sodium sulfate and evaporated. Automated flash column chromatography using a gradient of AcOEt in heptane (AcOEt 0%→20% over 25 min) furnished the title compound as a colorless oil (19.2 mg, 70%).

$^1$H NMR (300 MHz, CDCl$_3$): δ 7.45-7.39 (m, 6H), 7.32-7.23 (m, 4H), 7.08-6.95 (m, 4H), 5.19 (dd, J=6.0, 3.0 Hz, 1H), 4.59 (s, 2H), 3.51 (dd, J=14.6, 6.0 Hz, 1H), 2.92 (dd, J=14.6, 3.0 Hz, 1H). HRMS-ESI (m/z) calcd for C$_{22}$H$_{20}$ClN$_2$ [(M+H)$^+$] 347.1315, found: 347.1310.

(E)-N-(4-(4-(azidomethyl)phenyl)-1-phenylazetidin-2-ylidene)aniline

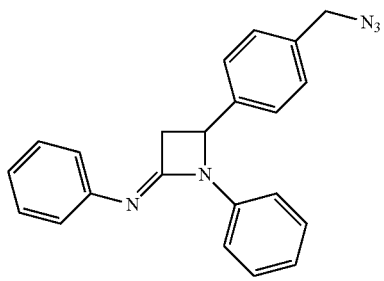 [SMILES: [N-]=[N+]=NCc1ccc(C2C/C(=N\c3ccccc3)N2c2ccccc2)cc1]

Step 1: A solution of 6 (148 mg, 0.45 mmol) and triethylamine (50 mg, 70 µL, 0.5 mmol, 2 equiv.) in DCM and under argon is cooled to 0° C. then MsCl (mesyl chloride, 57 mg, 39 µL, 0.5 mmol, 1.1 equiv.) is added. The reaction mixture is stirred at rt overnight. Afterwards, additional DCM (10 mL) is added and the reaction mixture is washed twice with water. The aqueous layer is extracted with DCM then the organic layer is dried over sodium sulfate and evaporated to afford the crude benzylic chloride intermediate. Step 2: To the previous crude residue is added DMF (0.5 mL), NaN$_3$ (33 mg, 0.5 mmol, 1.1 equiv.) and KI (8 mg, 0.045 mmol, 10 mol %). The reaction mixture is stirred overnight at 50° C. under air. Automated flash column chromatography using a gradient of AcOEt in heptane (AcOEt 0%→20% over 25 min) furnished the title compound as a colorless oil (98 mg, 62%).

$^1$H NMR (300 MHz, CDCl$_3$): δ 7.49-7.47 (m, 4H), 7.37-7.26 (m, 6H), 7.10-6.98 (m, 4H), 5.21 (dd, J=6.0, 3.0 Hz, 1H), 4.37 (s, 2H), 3.53 (dd, J=15.0, 6.0 Hz, 1H), 2.95 (dd, J=15.0, 3.0, 1H). HRMS-ESI (m/z) calcd for C$_{22}$H$_{20}$N$_5$ [(M+H)$^+$] 354.1719, found: 354.1727.

(E)-N-(1-phenyl-4-(4-((prop-2-yn-1-yloxy)methyl)phenyl)azetidin-2-ylidene)aniline

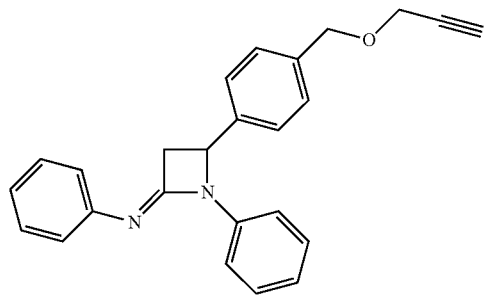 [SMILES: C#CCOCc1ccc(C2C/C(=N\c3ccccc3)N2c2ccccc2)cc1]

To a stirred solution of 6 (100 mg, 0.3 mmol) in anhydrous DMF and under argon is added NaH (13 mg, 0.33 mmol, 1.1 equiv.). After 10 min, a 70% wt. propargyl chloride solution in toluene (35 mg, 37 µL, 0.33 mmol, 1.1 equiv.) is added. The reaction mixture is stirred overnight. Automated flash column chromatography using a gradient of AcOEt in heptane (AcOEt 0%→20% over 25 min) furnished the title compound as a colorless oil (26 mg, 24%).

$^1$H NMR (300 MHz, CDCl$_3$): δ 7.46-7.37 (m, 6H), 7.33-7.22 (m, 4H), 7.08-6.95 (m, 4H), 5.19 (dd, J=6.0, 3.0 Hz, 1H), 4.61 (s, 2H), 4.20 (d, J=2.0 Hz, 2H), 3.51 (dd, J=15.0, 6.0 Hz, 1H), 2.92 (dd, J=15.0, 3.0 Hz, 1H), 2.48 (t, J=2.0, 1H). HRMS-ESI (m/z) calcd for C$_{25}$H$_{23}$N$_2$O [(M+H)$^+$] 367.1810, found: 367.1799.

The invention claimed is:
1. Compound of formula (I):

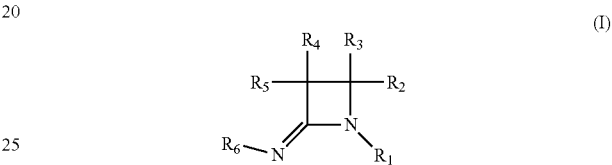

wherein:
R$_1$ represents a chemical moiety chosen in the group consisting of hydrogen, cyano, C$_3$-C$_{10}$ cycloalkyl, C$_1$-C$_{10}$ alkoxy, C$_1$-C$_{10}$ haloalkoxy, (C$_1$-C$_6$)-alkoxy-(C$_1$-C$_6$)-alkyl, (C$_1$-C$_6$)-haloalkoxy-(C$_1$-C$_6$)-alkyl, C$_1$-C$_{10}$ thioalkyl, (C$_1$-C$_6$)-alkylthio-(C$_1$-C$_6$)-alkyl, C$_1$-C$_{10}$ alkylsulfinyl, C$_1$-C$_{10}$ haloalkylsulfinyl, C$_1$-C$_{10}$ haloalkylsulfonyl, C$_3$-C$_{10}$ trialkylsilyl, C$_1$-C$_{10}$ alkylsulfonyl, C$_5$-C$_{12}$ arylsulfonyl, formyl, C$_2$-C$_{10}$ alkylcarbonyl, C$_2$-C$_{10}$ alkenyl, C$_2$-C$_{10}$ alkynyl, C$_2$-C$_{10}$ alkenyloxy, C$_2$-C$_{10}$ alkynyloxy, C$_2$-C$_{10}$ alkenylthio, C$_2$-C$_{10}$ alkynylthio, C$_1$-C$_{10}$ haloalkyl, C$_2$-C$_{10}$ haloalkenyl, C$_2$-C$_{10}$ haloalkynyl, C$_2$-C$_{10}$ haloalkylcarbonyl, C$_1$-C$_{10}$ haloalkylthio, C$_2$-C$_{10}$ haloalkenyloxy, C$_2$-C$_{10}$ haloalkynyloxy, C$_2$-C$_{10}$ haloalkenylthio, C$_2$-C$_{10}$ haloalkynylthio, (C$_5$-C$_{12}$)-aryl-(C$_1$-C$_6$)-alkyl, (C$_5$-C$_{12}$)-aryl-(C$_1$-C$_6$)-alkyl ester or a mono or polycyclic C$_5$-C$_{12}$ aryl or mono or polycyclic C$_3$-C$_{12}$ heteroaryl fragments,
wherein the aryl or heteroaryl fragments are optionally substituted by
one or several halogen atoms, hydroxyl (OH), nitro, cyano, formyl, C$_1$-C$_6$ alkyl, C$_3$-C$_7$ cycloalkyl, amino-C$_1$-C$_{10}$ alkoxy, (carboxylic acid)-C$_1$-C$_{10}$ alkoxy, (carboxylic (C$_1$-C$_6$)alkyl ester)-C$_1$-C$_{10}$ alkoxy, (1,2 diol)-C$_2$-C$_{10}$ alkoxy, —O—(C$_1$-C$_6$)alkyl-O—(C$_1$-C$_6$)alkyl-OH, (C$_1$-C$_6$)-alkoxy-(C$_1$-C$_6$)-alkyl, C$_2$-C$_6$ alkylcarbonyl, C$_1$-C$_6$ alkylthio, C$_1$-C$_6$ thioalkyl, (C$_1$-C$_6$)-alkylthio-(C$_1$-C$_6$)-alkyl, C$_1$-C$_6$ alkylsulfinyl, C$_1$-C$_6$ alkylsulfonyl, C$_1$-C$_6$ haloalkyl, C$_1$-C$_6$ haloalkoxy, C$_1$-C$_6$ haloalkoxy alkyl, C$_2$-C$_6$ haloalkylcarbonyl, C$_1$-C$_6$ haloalkylthio, C$_1$-C$_6$ haloalkylsulfinyl, C$_1$-C$_6$ haloalkylsulfonyl, C$_3$-C$_6$ trialkylsilyl, C$_2$-C$_6$ alkenyl, C$_2$-C$_6$ alkynyl, C$_2$-C$_6$ haloalkynyl, C$_2$-C$_6$ haloalkenyl, C$_2$-C$_6$ haloalkenyloxy, C$_2$-C$_6$ haloalkynyloxy, C$_2$-C$_6$ alkenyloxy, C$_2$-C$_6$ alkynyloxy, C$_2$-C$_6$ alkenylthio, C$_2$-C$_6$ alkynylthio, C$_2$-C$_6$ haloalkenylthio, C$_2$-C$_6$ haloalkynylthio and/or a C$_1$-C$_6$ alkoxy optionally substituted by a mono or polycyclic C$_5$-C$_{12}$ aryl group, and/or a bridging group of formula —O—CH$_2$—O— or —O—CH$_2$CH$_2$—O—;

R$_2$, R$_3$, R$_4$ and R$_5$, independently one from each other, represent a chemical moiety chosen in the group consisting of hydrogen, halogen, nitro, cyano, C$_1$-C$_{10}$ alkyl, C$_3$-C$_{10}$ cycloalkyl, C$_1$-C$_{10}$ alkoxy, C$_1$-C$_{10}$ haloalkoxy, (C$_1$-C$_6$)-alkoxy-(C$_1$-C$_6$)-alkyl, (C$_1$-C$_6$)-haloalkoxy-(C$_1$-C$_6$)-alkyl, C$_1$-C$_{10}$ thioalkyl, (C$_5$-C$_{12}$)-aryl-(C$_1$-C$_6$)-alkyl ester, (C$_1$-C$_6$)-alkylthio-(C$_1$-C$_6$)-alkyl, C$_1$-C$_{10}$ alkylsulfinyl, C$_1$-C$_{10}$ haloalkylsulfinyl, C$_1$-C$_{10}$ haloalkylsulfonyl, C$_3$-C$_{10}$ trialkylsilyl, C$_1$-C$_{10}$ alkylsulfonyl, C$_5$-C$_{12}$ arylsulfonyl, formyl, C$_2$-C$_{10}$ alkylcarbonyl, C$_2$-C$_{10}$ alkenyl, C$_2$-C$_{10}$ alkynyl, C$_2$-C$_{10}$ alkenyloxy, C$_2$-C$_{10}$ alkynyloxy, C$_2$-C$_{10}$ alkenylthio, C$_2$-C$_{10}$ alkynylthio, C$_1$-C$_{10}$ haloalkyl, C$_2$-C$_{10}$ haloalkenyl, C$_2$-C$_{10}$ haloalkynyl, C$_2$-C$_{10}$ haloalkylcarbonyl, C$_1$-C$_{10}$ haloalkylthio, C$_2$-C$_{10}$ haloalkenyloxy, C$_2$-C$_{10}$ haloalkynyloxy, C$_2$-C$_{10}$ haloalkenylthio, C$_2$-C$_{10}$ haloalkynylthio, (C$_5$-C$_{12}$)-aryl-(C$_1$-C$_6$)-alkyl or a mono or polycyclic C$_5$-C$_{12}$ aryl or mono or polycyclic C$_3$-C$_{12}$ heteroaryl fragments, wherein the aryl or heteroaryl fragments are optionally substituted by one or several halogen atoms, nitro, cyano, formyl, COOH, —COO(C$_1$-C$_6$ alkyl), C$_1$-C$_6$ alkyl, C$_3$-C$_7$ cycloalkyl, C$_1$-C$_6$ N$_3$-substituted alkyl, C$_1$-C$_6$ NH$_2$-substituted alkyl, C$_1$-C$_6$ alcohol, C$_1$-C$_6$ alkoxy, (C$_1$-C$_6$)-alkoxy-(C$_1$-C$_6$)-alkyl, C$_2$-C$_6$ alkylcarbonyl, C$_1$-C$_6$ alkylthio, C$_1$-C$_6$ thioalkyl, (C$_1$-C$_6$)-alkylthio-(C$_1$-C$_6$)-alkyl, C$_1$-C$_6$ alkylsulfinyl, C$_1$-C$_6$ alkylsulfonyl, C$_1$-C$_6$ haloalkyl, C$_1$-C$_6$ haloalkoxy, C$_1$-C$_6$ haloalkoxy alkyl, C$_2$-C$_6$ haloalkylcarbonyl, C$_1$-C$_6$ haloalkylthio, C$_1$-C$_6$ haloalkylsulfinyl, C$_1$-C$_6$ haloalkylsulfonyl, C$_3$-C$_6$ trialkylsilyl, C$_2$-C$_6$ alkenyl, C$_2$-C$_6$ alkynyl, C$_2$-C$_6$ haloalkynyl, C$_2$-C$_6$ haloalkenyl, C$_2$-C$_6$ haloalkenyloxy, C$_2$-C$_6$ haloalkynyloxy, C$_2$-C$_6$ alkenyloxy, C$_2$-C$_6$ alkynyloxy, C$_2$-C$_6$ alkenylthio, C$_2$-C$_6$ alkynylthio, C$_2$-C$_6$ haloalkenylthio, C$_2$-C$_6$ haloalkynylthio, a monocyclic C$_5$-C$_6$ aryl group optionally substituted by a C$_1$-C$_6$ alkyloxy group and/or a COO(C$_1$-C$_6$ alkyl) group wherein the alkyl is substituted by NH$_2$ or NHCOO(C$_1$-C$_6$)alkyl or NHCOO(C$_1$-C$_6$)alkyl(mono or polycyclic C$_5$-C$_{12}$)aryl;

R$_6$ represents a mono or polycyclic C$_5$-C$_{12}$ aryl fragment, wherein the aryl fragment is optionally substituted by one or several halogen atoms, cyano, formyl, nitro, C$_1$-C$_6$ alkyl, C$_3$-C$_7$ cycloalkyl, C$_1$-C$_6$ alkoxy, (C$_1$-C$_6$)-alkoxy-(C$_1$-C$_6$)-alkyl, C$_2$-C$_6$ alkylcarbonyl, C$_1$-C$_6$ alkylthio, C$_1$-C$_6$ thioalkyl, (C$_1$-C$_6$)-alkylthio-(C$_1$-C$_6$)-alkyl, C$_1$-C$_6$alkylsulfinyl, C$_1$-C$_6$ alkylsulfonyl, C$_1$-C$_6$ haloalkyl, C$_1$-C$_6$ haloalkoxy, C$_1$-C$_6$ haloalkoxy alkyl, C$_2$-C$_6$ haloalkylcarbonyl, C$_1$-C$_6$ haloalkylthio, C$_1$-C$_6$ haloalkylsulfinyl, C$_1$-C$_6$ haloalkylsulfonyl, C$_3$-C$_6$ trialkylsilyl, C$_2$-C$_6$ alkenyl, C$_2$-C$_6$ alkynyl, C$_2$-C$_6$ haloalkynyl, C$_2$-C$_6$ haloalkenyl, C$_2$-C$_6$ haloalkenyloxy, C$_2$-C$_6$ haloalkynyloxy, C$_2$-C$_6$ alkenyloxy, C$_2$-C$_6$ alkynyloxy, C$_2$-C$_6$ alkenylthio, C$_2$-C$_6$ alkynylthio, C$_2$-C$_6$ haloalkenylthio, C$_2$-C$_6$ haloalkynylthio fragments, and/or a monocyclic C$_5$-C$_6$ aryl group optionally substituted by a C$_1$-C$_6$ alkyloxy group;

or a solvate or a salt thereof;

provided that at least two of R$_3$, R$_4$ and R$_5$ represent a hydrogen atom and R$_2$ or R$_3$ is different from hydrogen.

2. The compound according to claim 1 characterized in that R$_6$ represents a R$_6$ represents a mono or polycyclic C$_5$-C$_{12}$ aryl fragment, optionally substituted by one or several halogen atoms, C$_1$-C$_6$ haloalkyl or C$_1$-C$_6$ alkoxy.

3. Compound according to claim 1 or 2, characterized in that R$_1$ represents a monocyclic aryl fragment optionally substituted by one or several OH, C$_1$-C$_6$ thioalkyl, halogen, amino-(C$_1$-C$_{10}$ alkoxy), (carboxylic acid)-(C$_1$-C$_{10}$ alkoxy), (carboxylic (C$_1$-C$_6$)alkylester)-C$_1$-C$_{10}$ alkoxy, (1,2 diol)-C$_2$-C$_{10}$ alkoxy, —O—(C$_1$-C$_6$)alkyl-O—(C$_1$-C$_6$)alkyl-OH, (C$_5$-C$_{12}$)-aryl-(C$_1$-C$_6$)-alkyl ester, nitro and/or a C$_1$-C$_6$ alkoxy group optionally substituted by a mono or polycyclic C$_5$-C$_{12}$ aryl group, and/or a bridging group of formula —O—CH$_2$—O— or —O—CH$_2$CH$_2$—O—.

4. The compound according to claim 1, wherein R$_2$ and/or R$_3$ represent a monocyclic aryl, monocyclic heteroaryl or polycyclic aryl fragment optionally substituted by one or several halogen atoms, COOH, —COO(C$_1$-C$_6$ alkyl), C$_1$-C$_6$ N$_3$-substituted alkyl, C$_1$-C$_6$ haloalkyl, C$_1$-C$_6$ alcohol, C$_1$-C$_6$ alkoxy, C$_1$-C$_6$ thioalkyl, C$_1$-C$_6$ acyl, nitro, cyano and/or a COO(C$_1$-C$_6$ alkyl) group wherein the alkyl is substituted by NH$_2$ or NHCOO(C$_1$-C$_6$)alkyl or NHCOO(C$_1$-C$_6$)alkyl (mono or polycyclic C$_5$-C$_{12}$)aryl fragment.

5. The compound according to claim 1, wherein R$_3$, R$_4$ and R$_5$ represent hydrogen atoms.

6. A compound selected from the group consisting of:

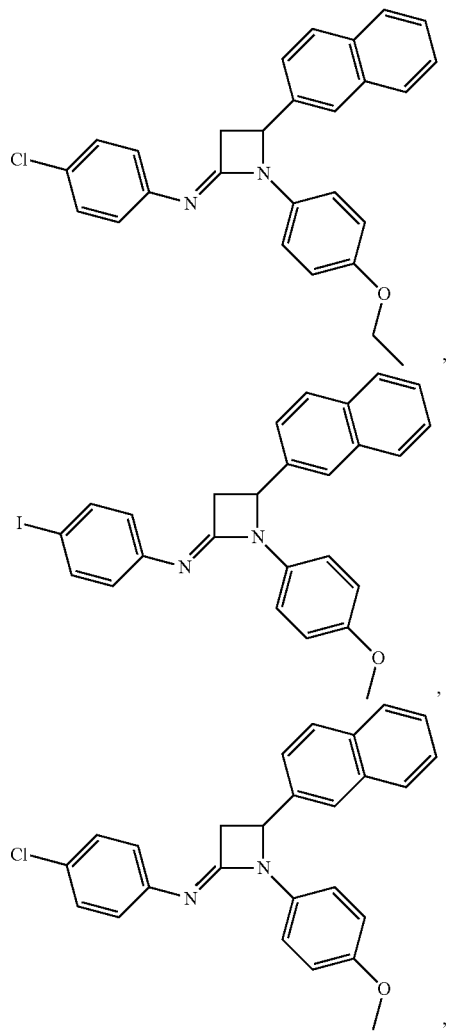

113
-continued
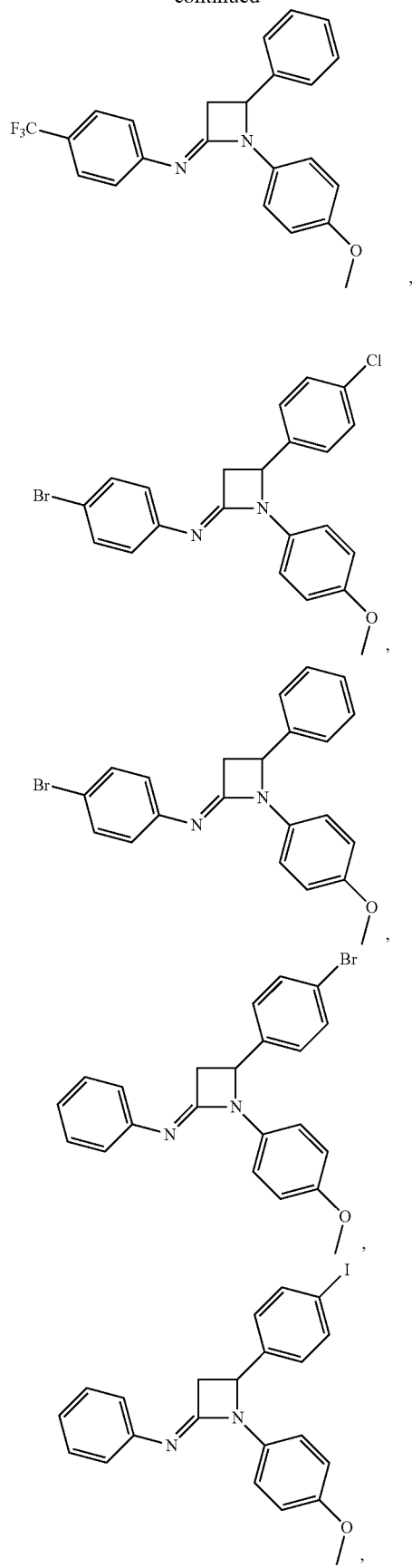
114
-continued
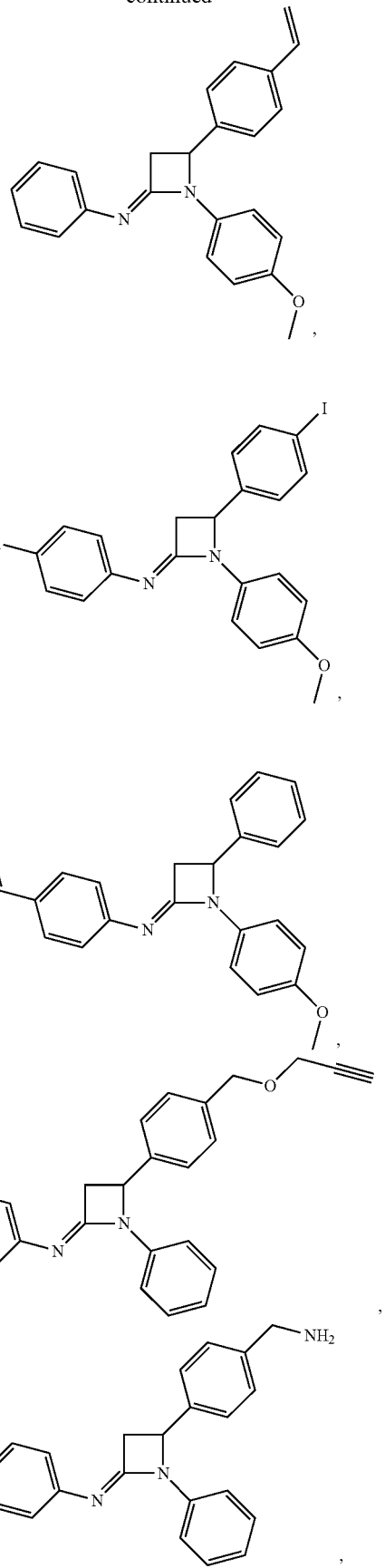

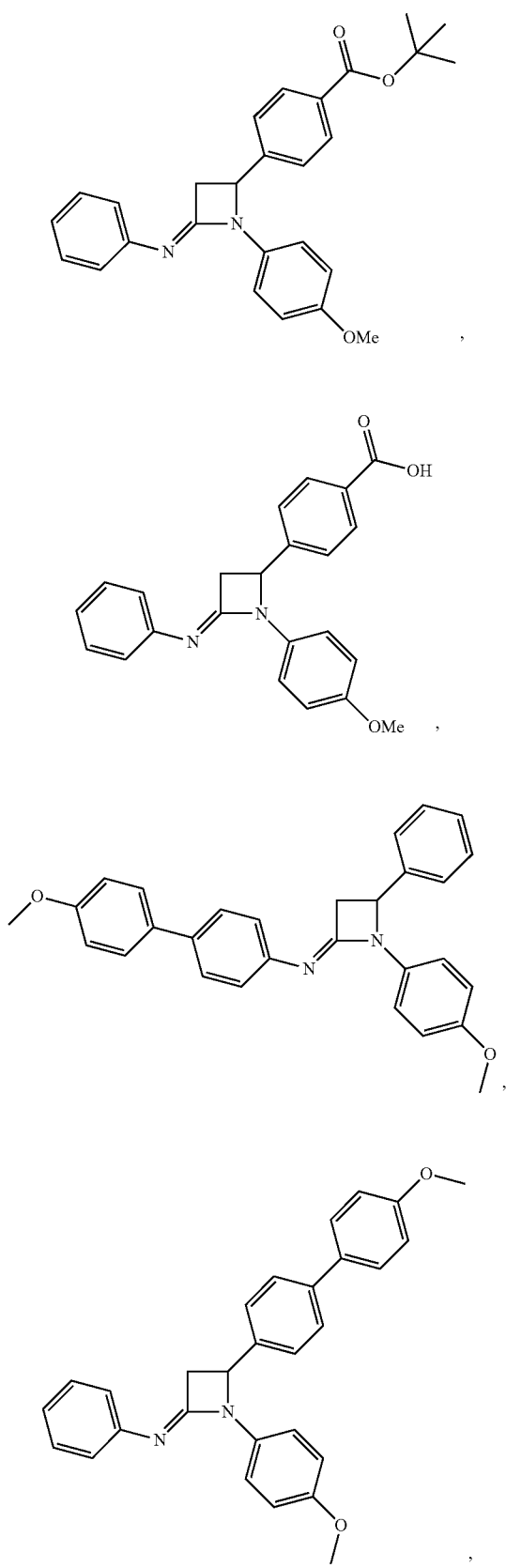
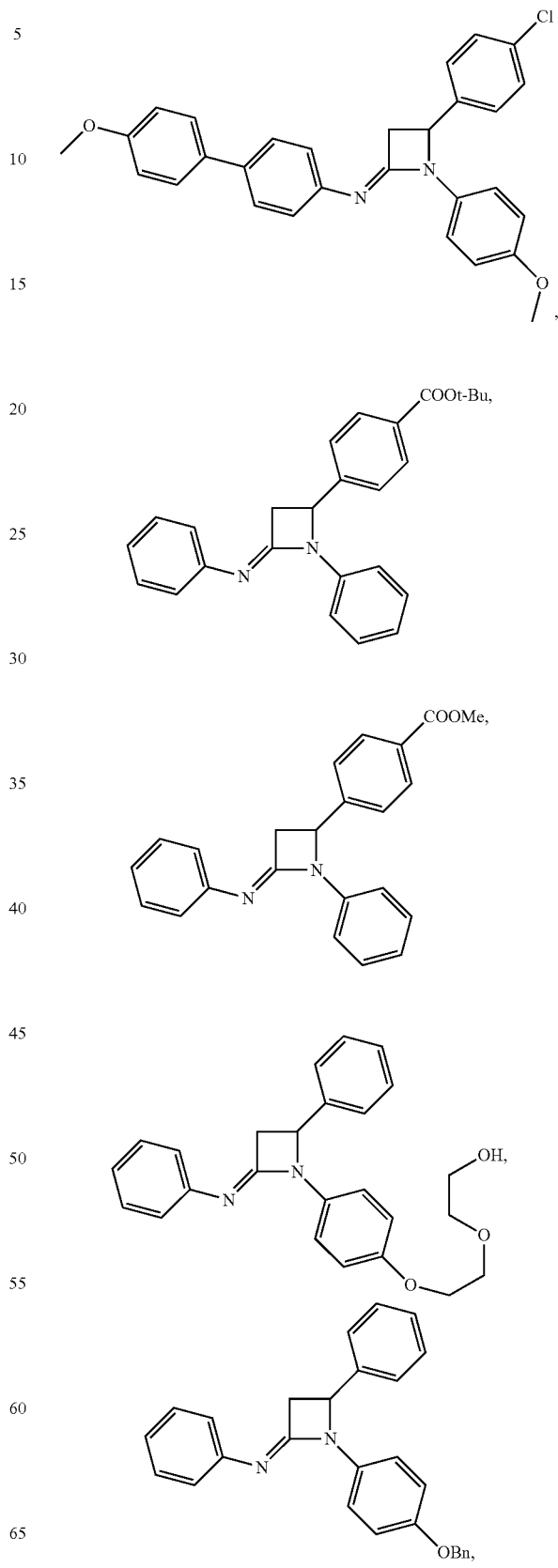

117
-continued
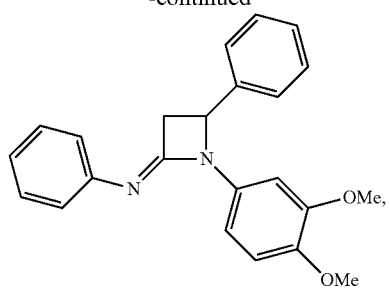
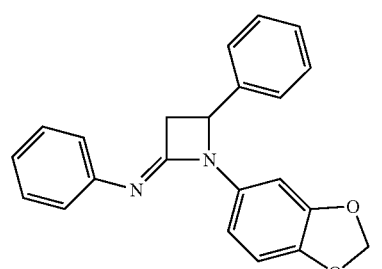
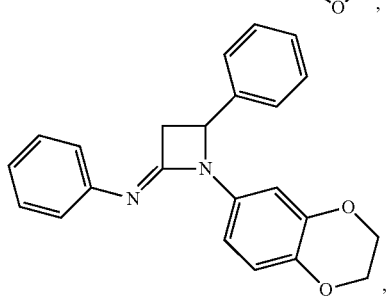
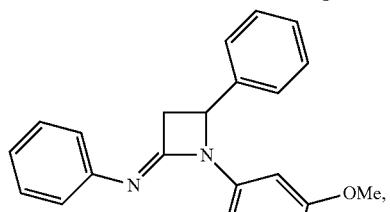
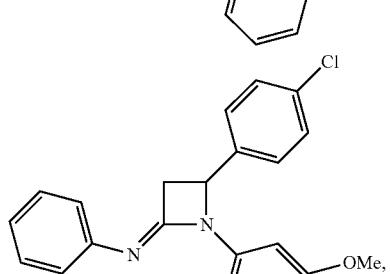
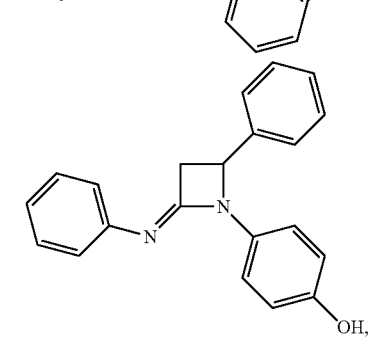
118
-continued
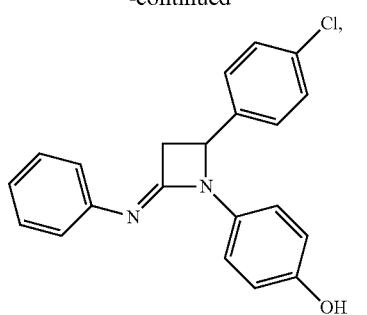
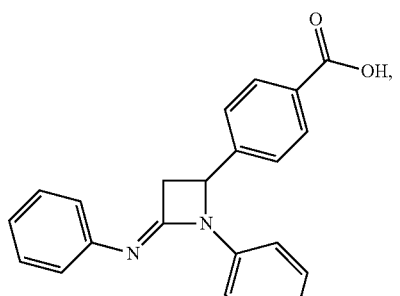
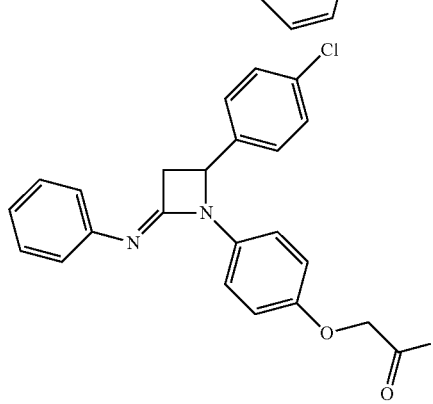
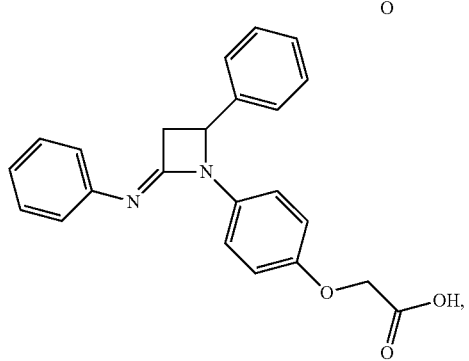
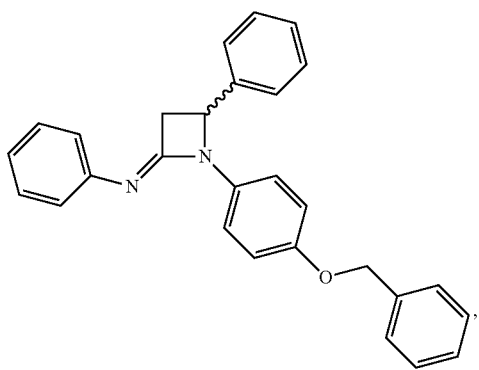

119
-continued
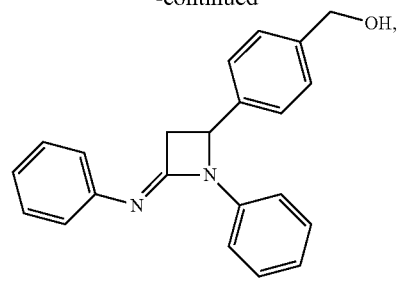
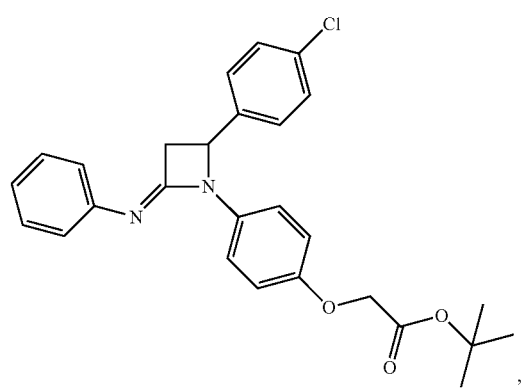
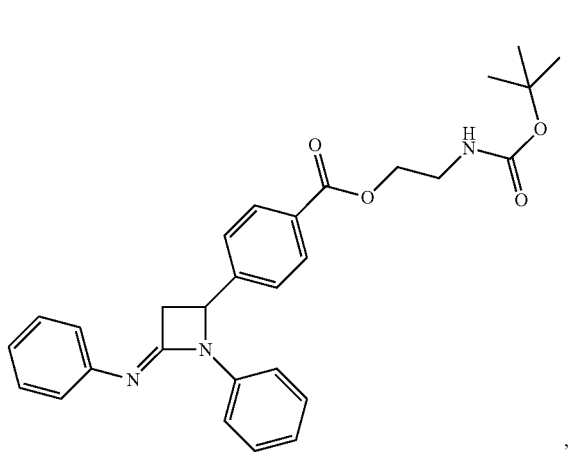
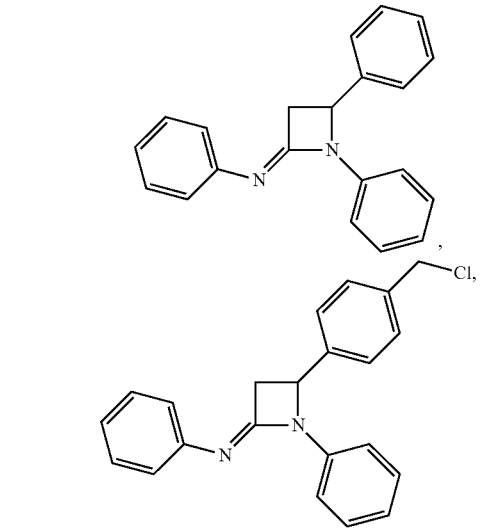
120
-continued
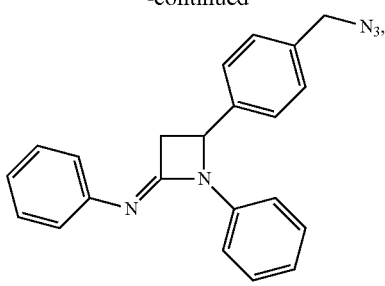
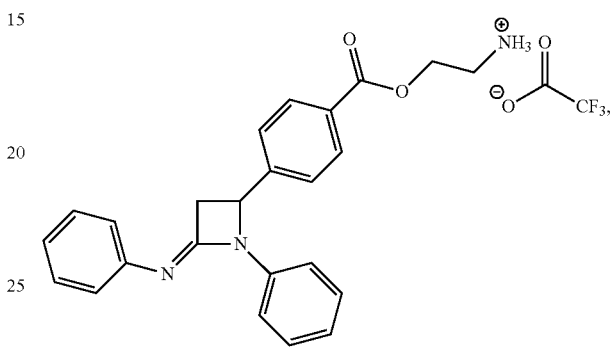
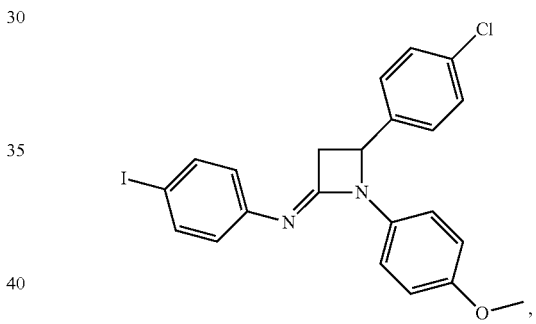
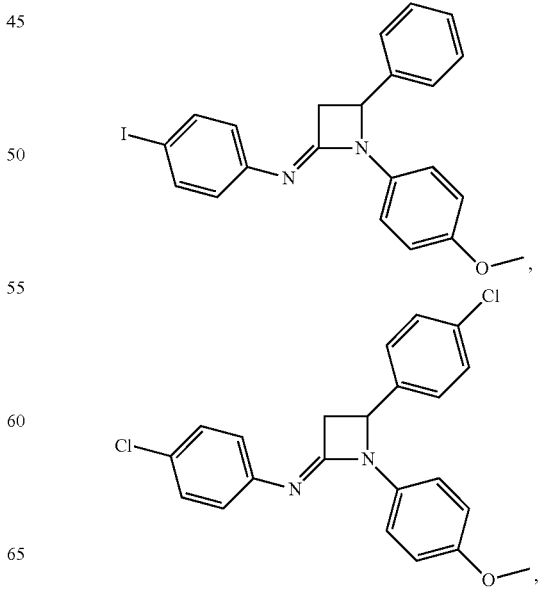

121
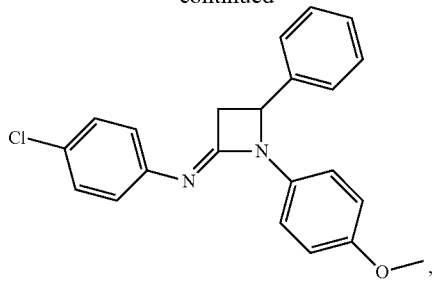
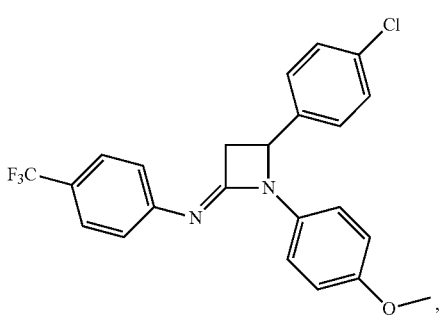
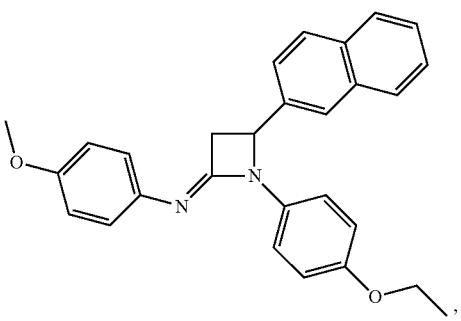
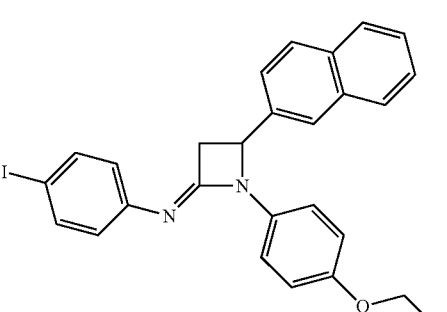
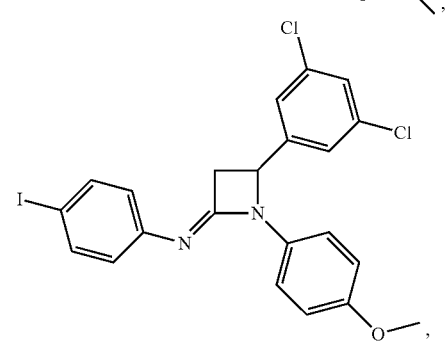
122
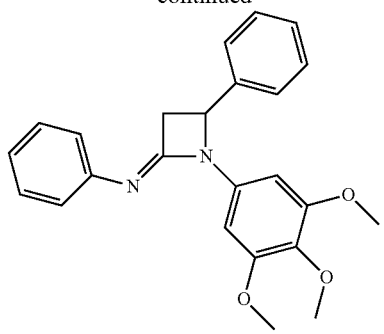
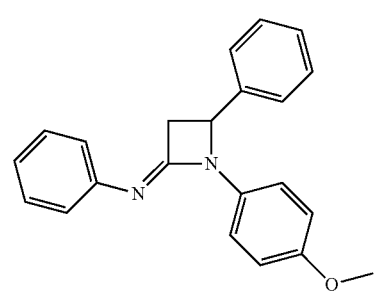
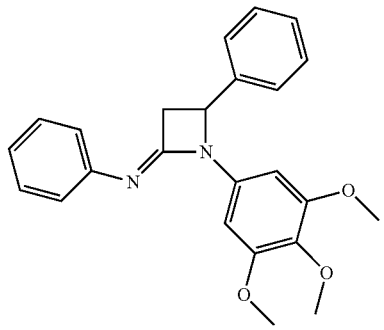
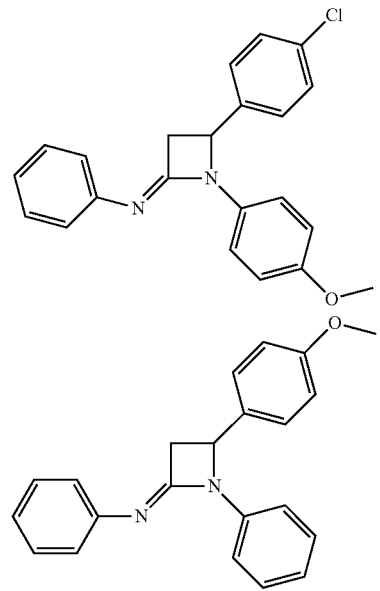

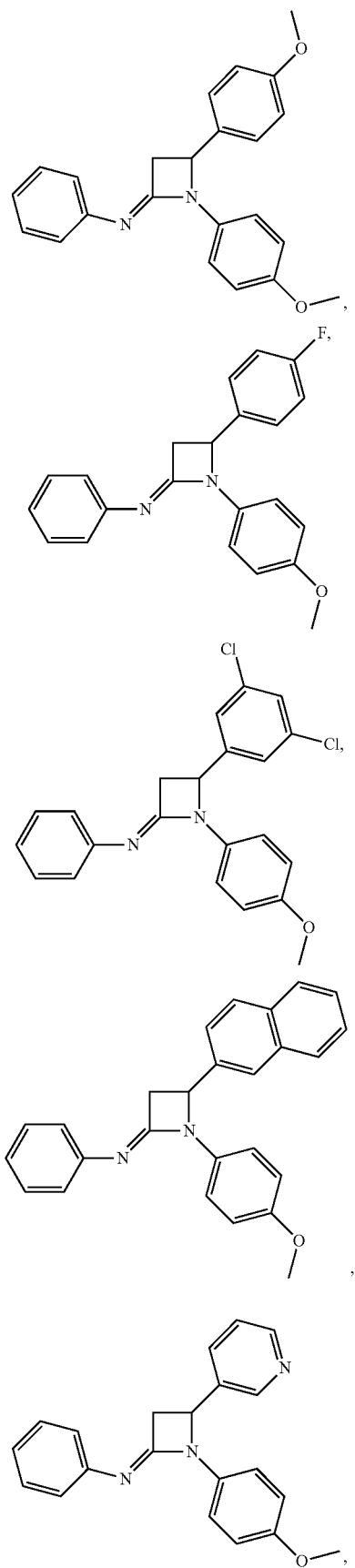
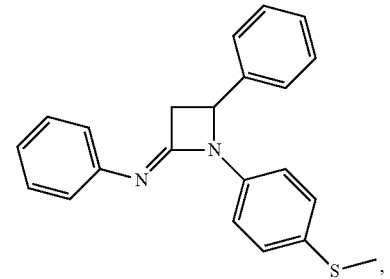
and/or

-continued

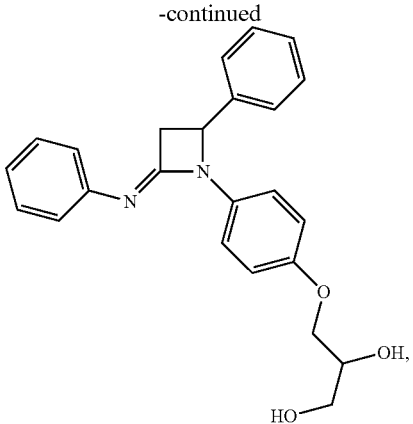

a solvate or a salt thereof.

7. The compound according to claim 1, wherein $R_1$ represents a monocyclic aryl fragment optionally substituted by one or several $C_1$-$C_6$ alkoxy, $C_1$-$C_6$ thioalkyl, halogen, amino-($C_1$-$C_{10}$ alkoxy), (carboxylic acid)-($C_1$-$C_{10}$ alkoxy), (1,2 diol)-($C_2$-$C_{10}$ alkoxy), ($C_5$-$C_{12}$)-aryl-($C_1$-$C_6$)-alkyl ester and/or nitro fragments.

8. The compound according to claim 1 wherein R1 represents a phenyl fragment, a 4-hydroxyphenyl, a 4-methoxyphenyl, a 2-methoxyphenyl, a 3-methoxyphenyl, a 3,4-dimethoxyphenyl, a 3,4,5-trimethoxyphenyl, a 4-methylthio-phenyl, a 4-ethoxy-phenyl, a 4-benzyloxy-phenyl, a 1,3-benzodioxole, a 1,4-benzodioxane, a 4-[(2,3 diol)-propoxy]-phenyl, a 4-phenoxyacetic acid, a tert-butyl 4-(phenoxy)acetate, a 4-(bis(2-hydroxyethyl)ether)phenyl or a 4-iodo-phenyl.

9. The compound according to claim 1 wherein R1 represents a 4-hydroxyphenyl.

10. The compound according to claim 1 wherein R2 and/or R3 represent a fragment chosen from the group consisting of phenyl, 4- methoxy phenyl, 4-formylphenyl, 4-nitro phenyl, 4-fluorophenyl, 4-chlorophenyl, 2,4-dichlorophenyl, naphthyl, indolyl, furanyl, pyridyl, and thiophenyl.

11. The compound according to claim 1 wherein R2 represents a 2,4-dichlorophenyl.

12. The compound according to claim 1 wherein R6 represents a phenyl group, optionally substituted by 1 to 3 halogen atoms, $C_1$-$C_6$ haloalkyl or $C_1$-$C_6$ alkoxy.

13. The compound according to claim 1 wherein R6 represents a phenyl group, optionally substituted by 1 to 3 iodine atoms.

14. The compound according to claim 1 wherein R1 represents a 4-hydroxyphenyl, R2 represents a 2,4- dichlorophenyl, R6 represents a phenyl group, optionally substituted by 1 to 3 iodine atoms, and R3, R4 and R5 represent hydrogen atoms.

15. A composition comprising a combination of a compound of formula (I) as defined in claim 1 and an antibiotic.

16. The composition according to claim 15 wherein said antibiotic is effective on bacteria chosen from gram-negative bacteria.

17. The composition according to claim 16, wherein said gram-negative bacteria is selected from the group consisting of Enterobacteriaceae, Pseudomonas aeruginosa, Acinetobacter baumannii.

18. A pharmaceutical composition comprising at least one compound of formula (I) as defined in claim 1, and a pharmaceutically acceptable carrier.

19. The pharmaceutical composition of claim 18, wherein it comprises a second active substance.

20. The pharmaceutical composition according to claim 19, wherein said second active substance is an antibiotic.

21. A method for inhibiting a carbapenemase enzyme wherein a compound of formula (I) as defined in claim 1 is used as a carbapenemase enzyme inhibitor.

22. The method according to claim 21, wherein the carbapenemase enzyme, is a NDM-1 type, OXA-48 type or a KPC-type enzyme.

23. A method of therapeutical treatment comprising the administration of a compound of formula (I) as defined in claim 1 as a drug.

24. The method of claim 23, wherein the drug is an antibiotic.

25. A kit comprising:
at least one first container containing a first therapeutically active compound of formula (I) as defined in claim 1 and mixtures thereof, and
at least one second container containing a second therapeutically active substance which is an antibiotic, as a combination product for simultaneous, sequential and separate use.

26. The kit according to claim 25, as a combination product for simultaneous, sequential and separate use in antibiotherapy.

27. A method to prepare a compound of formula (I):
a. to a compound of formula (II):

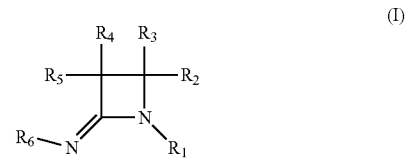

wherein:
$R_1$ represents a chemical moiety chosen in the group consisting of hydrogen, cyano, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$) -haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_3$-$C_{10}$ trialkylsilyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester or a mono or polycyclic $C_5$-$C_{12}$ aryl or mono or polycyclic $C_3$-$C_{12}$ heteroaryl fragments,
wherein the aryl or heteroaryl fragments are optionally substituted by
one or several halogen atoms, hydroxyl (OH), nitro, cyano, formyl, $C_1$-$C_6$ alkyl, $C_3$-$C_7$ cycloalkyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl,$C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy,$C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, and/or a bridging group of formula —O—$CH_2$—O— or —O—$CH_2CH_2$—O—;

$R_2$, $R_3$, $R_4$ and $R_5$, independently one from each other, represent a chemical moiety chosen in the group consisting of hydrogen, halogen, nitro, cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_3$-$C_{10}$ trialkylsilyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, COOH, —COO($C_1$-$C_6$ alkyl), $C_1$-$C_6$ alkyl, $C_3$-$C_7$ cycloalkyl, $C_1$-$C_6$ $N_3$-substituted alkyl, $C_1$-$C_6$ $NH_2$-substituted alkyl, $C_1$-$C_6$ alcohol, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio, a monocyclic $C_5$-$C_6$ aryl group optionally substituted by a $C_1$-$C_6$ alkyloxy group and/or a COO($C_1$-$C_6$ alkyl) group wherein the alkyl is substituted by $NH_2$ or NHCOO($C_1$-$C_6$)alkyl or NHCOO($C_1$-$C_6$)alkyl(mono or polycyclic $C_5$-$C_{12}$)aryl;

$R_6$ represents a mono or polycyclic $C_5$-$C_{12}$ aryl fragment, wherein the aryl fragment is optionally substituted by one or several halogen atoms, cyano, formyl, nitro, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio fragments, and/or a monocyclic $C_5$-$C_6$ aryl group optionally substituted by a $C_1$-$C_6$ alkyloxy group, provided that at least two of $R_3$, $R_4$ and $R_5$ represent a hydrogen atom and $R_2$ or $R_3$ is different from hydrogen;

said method comprising the following steps:
a. to a compound of formula (II):

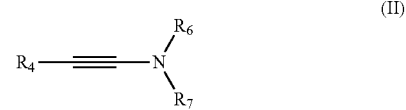

(II)

wherein $R_4$ and $R_6$ are as defined in said compound of formula (I) and $R_7$ represents a leaving group, optionally, $R_6$—N—$R_7$ may form at least one ring wherein $R_6$ and $R_7$ directly linked one to each other and wherein said ring comprises from 3 to 12 atoms chosen from C, N, O, S, B and P, substituted by at least one hydrogen, oxygen, nitrogen, hydroxyl, thiol, amine, cyano, $C_1$-$C_6$ alkyl, $C_3$-$C_6$ cycloalkyl, $C_1$-$C_6$ alkoxy, $C_1$-$C_6$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ haloalkylsulfinyl, $C_1$-$C_6$ haloalkylsulfonyl, $C_3$-$C_6$ trialkylsilyl, $C_1$-$C_6$ alkylsulfonyl, $C_5$-$C_{12}$ arylsulfonyl, formyl, $C_2$-$C_6$ alkylcarbonyl, $C_2$-$C_6$ alkenyl, $C_2$-$C_6$ alkynyl, $C_2$-$C_6$ alkenyloxy, $C_2$-$C_6$ alkynyloxy, $C_2$-$C_6$ alkenylthio, $C_2$-$C_6$ alkynylthio, $C_1$-$C_6$ haloalkyl, $C_2$-$C_6$ haloalkenyl, $C_2$-$C_6$ haloalkynyl, $C_2$-$C_6$ haloalkylcarbonyl, $C_1$-$C_6$ haloalkylthio, $C_2$-$C_6$ haloalkenyloxy, $C_2$-$C_6$ haloalkynyloxy, $C_2$-$C_6$ haloalkenylthio, $C_2$-$C_6$ haloalkynylthio, ($C_5$-$C_{12}$)-aryl-($C_1$-$C_6$)-alkyl or a mono or polycyclic $C_5$-$C_{12}$ aryl or mono or polycyclic $C_3$-$C_{12}$ heteroaryl fragments, wherein the aryl or heteroaryl fragments are optionally substituted by one or several halogen atoms, nitro, cyano, formyl, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or nitro fragments;

is added a compound of formula (III):

(III)

wherein $R_1$, $R_2$ and $R_3$ are as defined in said compound of formula (I) in the presence of a base;

b. an optional addition step of $R_5$ as defined in claim 1 through a nucleophilic addition to the compound obtained in step a., and, c. retrieving the compound of formula (I) as defined in claim 1.

28. The method according to claim 27, wherein $R_1$ is an electro-donating group and/or $R_2$ and/or $R_3$ are electron-withdrawing groups.

29. The method according to claim 27, wherein $R_7$ represents a leaving group selected from the group consisting of amides, sulfonyl, and_oxy-carbonyls.

30. The method according to claim 27, wherein the nucleophilic addition to the compound obtained in step a. is performed with R5-X, wherein X is a halogen atom in the presence of a base.

31. The method according to claim 27, wherein step (a) is carried out under microwaves.

32. The method according to claim 27, wherein step (a) is carried out under pressure and/or at a temperature above 50° C.

33. The method according to claim 27, wherein step (a) is carried out without the presence of a metal compound, whether it is in its metallic or one of its oxidized or reduced forms.

* * * * *